United States Patent
Sakamoto et al.

(10) Patent No.: US 6,376,428 B1
(45) Date of Patent: Apr. 23, 2002

(54) DIHALOPROPENE COMPOUNDS, INSECTICIDAL/ACARICIDAL AGENTS CONTAINING SAME, AND INTERMEDIATES FOR THEIR PRODUCTION

(75) Inventors: Noriyasu Sakamoto; Sanshiro Matsuo, both of Toyonaka; Masaya Suzuki, Takarazuka; Taro Hirose, Osaka; Kazunori Tsushima, Sanda; Kimitoshi Umeda, Funabashi, all of (JP)

(73) Assignee: Sumitomo Chemical Company, Limited, Osaka-fu (JP)

( * ) Notice: Subject to any disclaimer, the term of this patent is extended or adjusted under 35 U.S.C. 154(b) by 0 days.

(21) Appl. No.: 09/864,227

(22) Filed: May 25, 2001

Related U.S. Application Data

(62) Division of application No. 09/521,119, filed on Mar. 7, 2000, now Pat. No. 6,268,313, which is a division of application No. 09/203,362, filed on Dec. 2, 1998, now Pat. No. 6,071,861, which is a division of application No. 08/809,865, filed as application No. PCT/JP95/02080 on Oct. 12, 1995, now Pat. No. 5,922,880.

(30) Foreign Application Priority Data

Oct. 14, 1994 (JP) .............................................. 6-249296
Apr. 17, 1995 (JP) .............................................. 7-091187

(51) Int. Cl.$^7$ ........................ A01N 43/60; A01N 43/72; C07D 257/08; C07D 237/28; C07D 241/04
(52) U.S. Cl. ..................... 504/235; 504/222; 504/223; 504/227; 504/228; 504/236; 504/239; 504/240; 504/242; 544/179; 544/180; 544/233; 544/235; 544/242; 544/298; 544/322; 544/336; 544/349; 544/358; 544/383; 544/384
(58) Field of Search .................................. 504/222, 223, 504/227, 228, 235, 236, 239, 240, 242; 544/179, 180, 233, 235, 238, 242, 298, 322, 336, 349, 358, 383, 386

(56) References Cited

U.S. PATENT DOCUMENTS

| 4,048,235 | A | | 9/1977 | Karrer |
| 4,123,556 | A | | 10/1978 | Karrer |
| 5,872,137 | A | | 2/1999 | Sakamoto |
| 5,922,880 | A | * | 7/1999 | Sakamoto |
| 5,952,386 | A | | 9/1999 | Matsuo |
| 6,028,100 | A | | 2/2000 | Matsuo |
| 6,071,861 | A | * | 6/2000 | Sakamoto |
| 6,268,313 | B1 | * | 7/2001 | Sakamoto |

FOREIGN PATENT DOCUMENTS

| EP | 0203798 | | 12/1986 |
| EP | 0218543 A | | 4/1987 |
| EP | 0123456 A2 | | 1/2000 |
| JP | 60237056 | | 11/1985 |
| JP | 04342568 | | 11/1992 |
| WO | 96/11909 | * | 4/1996 |

OTHER PUBLICATIONS

J. Org. Chem., vol. 31, pp. 3666–3671 (1966).

* cited by examiner

Primary Examiner—D. Margaret Seaman
(74) Attorney, Agent, or Firm—Birch, Stewart, Kolasch & Birch, LLP

(57) ABSTRACT

The dihalopropene compounds of the general formula [I] have excellent insecticidal/acaricidal activity, so that they are satisfactorily effective for the control of noxious insects, mites and ticks.

18 Claims, No Drawings

DIHALOPROPENE COMPOUNDS, INSECTICIDAL/ACARICIDAL AGENTS CONTAINING SAME, AND INTERMEDIATES FOR THEIR PRODUCTION

This application is a DIV of application Ser. No. 09/521,119 filed Mar. 7, 2000 (now U.S. Pat. No. 6,268,313), which is a DIV of application Ser. No. 09/203,362 filed Dec. 2, 1998 (now U.S. Pat. No. 6,071,861), which is a DIV of application Ser. No. 08/809,865 filed May 20, 1997 (now U.S. Pat. No. 5,922,880) which is a 371 of PCT/JP95/02080 filed Oct. 12, 1995. The entire contents of each of the above-identified application are hereby incorporated by reference. This application also claims priority of Application No. 6-249296 and 7-091187 filed in Japan on Oct. 14, 1994 and Apr. 17, 1995, respectively under 35 U.S.C. 119.

TECHNICAL FIELD

The present invention relates to dihalopropene compounds, insecticidal/acaricidal agents containing these compounds as active ingredients, and intermediates for their production.

BACKGROUND ART

As disclosed in JP-A 48-8683511973 and JP-A 49-1526/1974, for example, it is well known that some kinds of propene compounds can be used as an active ingredient of insecticides.

In view of their insecticidal/acaricidal activity, it cannot always be said that these compounds are satisfactorily effective for the control of noxious insects, mites and ticks.

DISCLOSURE OF INVENTION

The present inventors have intensively studied to find a compound having excellent insecticidal/acaricidal activity. As a result, they have found that particular dihalopropene compounds have satisfactory insecticidal/acaricidal activity for the control of noxious insects, mites and ticks, thereby completing the present invention.

That is, the present invention provides a dihalopropene compound (herein-after referred to as the present compound) of the general formula:

[I]

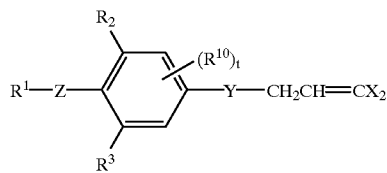

wherein Z is oxygen, sulfur or $NR^4$ (wherein $R^4$ is hydrogen or $C_1$–$C_3$ alkyl); Y is oxygen, sulfur or NH; X's are independently chlorine or bromine; $R^2$, $R^3$ and $R^{10}$ are independently halogen, $C_1$–$C_3$ haloalkyl or $C_1$–$C_3$ alkyl; t is an integer of 0 to 2; and $R^1$ is $Q_1$, $Q_2$, $Q_3$, $Q_4$, $Q_5$, $Q_6$ or $Q_7$ of the general formula:

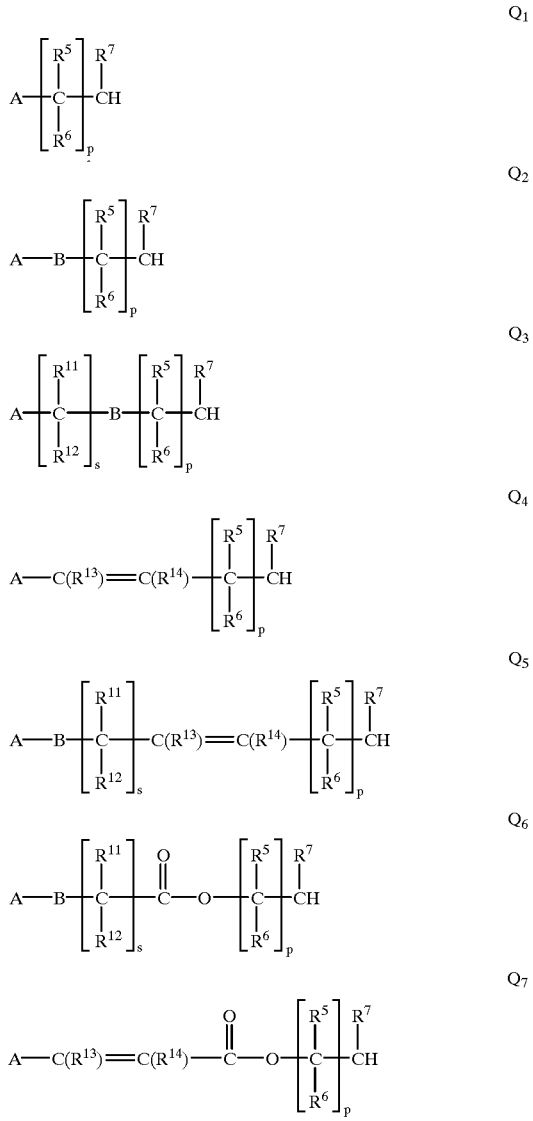

wherein A is an optionally substituted heterocyclic ring group, provided that when A is an optionally substituted heterocyclic ring group containing two oxygen atoms and a condensed benzene ring, A is optionally substituted 1,3-benzodioxolan-2-yl or optionally substituted 1,4-benzodioxan-2-yl; B is oxygen, $S(O)_q$, $NR^9$, $C(=G^1)G^2$ or $G^1C(G^2)$; q is an integer of 0 to 2; $R^9$ is hydrogen, acetyl or $C_1$–$C_3$ alkyl; $G^1$ and $G^2$ are independently oxygen or sulfur; $R^5$, $R^6$, $R^7$, $R^{11}$ and $R^{12}$ are independently hydrogen, $C_1$–$C_3$ alkyl or trifluoromethyl; $R^{13}$ and $R^{14}$ are independently hydrogen, $C_1$–$C_3$ alkyl, trifluoromethyl or halogen; p is an integer of 0 to 6; and s is an integer of 1 to 6.

The present invention further provides an insecticidal/acaricidal agent containing the above dihalopropene compound as an active ingredient.

The present invention further provides the following compounds which are useful as intermediates for producing some of the present compounds:

a phenol compound which is 3,5-dichloro-4-(2-(2-(4-chlorophenyl)-1,3-dioxolan-4-yl)ethoxy)phenol;
compounds of the general formula:

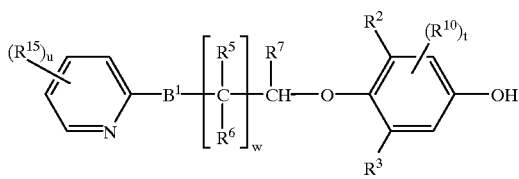

[II]

wherein $R^5$, $R^6$ and $R^7$ are independently hydrogen, $C_2$–$C_3$ alkyl or trifluoromethyl; $R^{15}$ is halogen, $C_1$–$C_3$ alkyl, $C_1$–$C_3$ haloalkyl, $C_1$–$C_3$ alkoxy or $C_1$–$C_3$ haloalkoxy; $R^2$, $R^3$ and $R^{10}$ are independently halogen, $C_1$–$C_3$ alkyl or $C_1$–$C_3$ haloalkyl; t is an integer of 0 to 2; u is an integer of 1 to 4; w is an integer of 1 to 4; and $B^1$ is oxygen, $S(O)_q$ or $NR^9$ wherein $R^9$ is hydrogen, acetyl or $C_1$–$C_3$ alkyl and q is an integer of 0 to 2;

compounds of the general formula [I] wherein $R^5$, $R^6$ and $R^7$ are all hydrogen; and $R^2$ and $R^3$ are independently halogen or $C_1$–$C_3$ alkyl; and 2-(3-methanesulfonyloxypropyloxy)-5-trifluoromethylpyridine.

DETAILED DESCRIPTION OF THE INVENTION

The variables in the above formulae for the present compounds and their intermediates can take the following specific examples.

Examples of the $C_1$–$C_3$ alkyl group represented by $R^2$, $R^3$, $R^4$, $R^5$, $R^6$, $R^7$, $R^9$, $R^{10}$, $R^{11}$, $R^{12}$, $R^{13}$ or $R^{14}$ are methyl, ethyl, n-propyl and isopropyl.

Examples of the halogen atom represented by $R^{13}$ or $R^{14}$ are fluorine, chlorine, bromine and iodine.

Examples of the heterocyclic ring in the optionally substituted heterocyclic ring group represented by A are isoxazole, isothiazole, thiazole, 1,3,4-thiadiazole, pyrrole, furan, thiophene, pyrazole, imidazole, 1,2,3-triazole, 1,2,4-triazole, 1,2,3,4-tetrazole, pyridine, pyridazine, pyrimidine, pyrazine, 1,2,4-triazine, 1,3,5-triazine, indole, benzofuran, thianaphthalene, indazole, benzimidazole, benzotriazole, benzisoxazole, benzoxazole, benzothiazole, quinoline, isoquinoline, quinoxaline, quinazole, piperidine, piperazine, tetrahydrofuran, tetrahydropyran, pyrazoline, phthalimide, dioxane, dioxolane and benzodioxolane.

Examples of the substituent on the optionally substituted heterocyclic ring group represented by A are those of the general formula: $(R^8)_r$ (wherein $R^8$ is halogen, nitro, cyano, $C_1$–$C^4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, $(C_1$–$C_2$ alkyl)aminocarbonyl or [di($C_1$–$C_2$ alkyl)amino]carbonyl, or $R^8$ is phenyl, benzyl, phenoxy, benzyloxy or pyridyloxy, each of which is optionally substituted with halogen, $C_1$–$C_4$ alkyl, $C_1$–$C3$ haloalkyl, $C_1$–$C_4$ alkoxy or $C_1$–$C_3$ haloalkoxy; and r is an integer of 0 to 7.

Examples of the halogen atom represented by $R^8$ or present in $R^8$ are fluorine, chlorine, bromine and iodine.

Examples of the $C_1$–$C_4$ alkyl group represented by $R^8$ or present in $R^8$ are methyl, ethyl, n-propyl, isopropyl, n-butyl, isobutyl, sec-butyl and tert-butyl.

Examples of the $C_1$–$C_3$ haloalkyl group represented by $R^8$ or present in $R^8$ are trifluoromethyl, difluoromethyl, bromodifluoromethyl, 2,2,2-trifluoroethyl, 2-fluoroethyl, 2-chloroethyl, 2-bromoethyl, 1-fluoroethyl, 1-chloroethyl, 1-bromoethyl, 2,2,3,3,3-pentafluoropropyl, 3,3,3-trifluoropropyl, 1-fluoropropyl, 2-chloropropyl and 3-bromopropyl.

Examples of the $C_1$–$C_4$ alkoxy group represented by $R^8$ or present in $R^8$ are methoxy, ethoxy, n-propoxy, isopropoxy, n-butoxy, sec-butoxy, isobutoxy and tert-butoxy.

Examples of the $C_1$–$C_3$ haloalkoxy group represented by $R^8$ or present in $R^8$ are trifluoromethoxy, difluoromethoxy, bromofluoromethoxy, 2-fluoroethoxy, 2,2,2-trifluoroethoxy, 2-chloroethoxy, 2-bromoethoxy, 2-chloro-1,1,2-trifluoroethoxy, 2-bromo-1,1,2-trifluoroethoxy, 1,1,2,2-tetrafluoroethoxy, 1,2,2,3,3,3-hexafluoropropoxy, 3-fluoropropoxy, 3-chloropropoxy, 3-bromopropoxy, 2,2,3,3,3-pentafluoropropoxy, 3,3,3-trifluoropropoxy and 1,1,2,2,2-pentafluoroethoxy.

Examples of the $C_1$–$C_3$ alkylthio group represented by $R^8$ are methylthio, ethylthio, n-propylthio and isopropylthio.

Examples of the $C_1$–$C_3$ haloalkylthio group represented by $R^8$ are trifluoromethylthio, difluoromethylthio, bromodifluoromethylthio, 2,2,2-trifluoroethylthio, 2-chloro-1,1,2-trifluoroethylthio, 2-bromo-1,1,2-trifluoroethylthio, 1,1,2,2-tetrafluoroethylthio, 2-chloroethylthio, 2-fluoroethylthio, 2-bromoethylthio, 3-fluoropropylthio, 3-chloropropylthio, (3-bromopropyl)thio, 2,2,3,3,3-pentafluoropropylthio and 3,3,3-trifluoropropylthio.

Examples of the $C_1$–$C_2$ alkylsulfinyl group represented by $R^8$ are methylsulfinyl and ethylsulfinyl.

Examples of the $C_1$–$C_2$ alkylsulfonyl group represented by $R^8$ are methylsulfonyl and ethylsulfonyl.

Examples of the $C_1$–$C_2$ haloalkylsulfinyl group represented by $R^8$ are trifluoromethylsulfinyl, 2,2,2-trifluoroethylsulfinyl and perfluoroethylsulfinyl.

Examples of the $C_1$–$C_2$ haloalkylsulfonyl group represented by $R^8$ are trifluoromethylsulfonyl, 2,2,2-trifluoroethylsulfonyl and perfluoroethylsulfonyl.

Examples of the $C_2$–$C_4$ alkenyl group represented by $R^8$ are vinyl, isopropenyl, 1-propenyl, 2-ethyl-1-propenyl, 1-methyl-1-propenyl, allyl, 2-methylpropenyl and 2-butenyl.

Examples of the $C_2$–$C_4$ haloalkenyl group represented by $R^8$ are 2,2-dichloroethenyl, 2,2-dibromoethenyl, 3,3-dichloroallyl, 3,3-dibromoallyl, 2,3-dichloroallyl, 2,3-dibromoallyl, 2-chloro-2-propenyl, 3-chloro-2-propenyl, 2-bromo-2-propenyl and 3-chloro-2-butenyl.

Examples of the $C_2$–$C_4$ alkynyl group represented by $R^8$ are ethynyl, 1-propynyl, 2-propynyl and 1-methyl-2-propynyl.

Examples of the $C_2$–$C_4$ haloalkynyl group represented by $R^8$ are chloroethynyl, bromoethynyl, iodoethynyl, 3-chloro-2-propynyl, 3-bromo-2-propynyl, 3-iodo-2-propynyl, 1-methyl-3-chloro-2-propynyl, 1-methyl-3-bromo-2-propynyl and 1-methyl-3-iodo-2-propynyl.

Examples of the haloacetyl group represented by $R^8$ are trifluoromethylacetyl and trichloroacetyl.

Examples of the $C_3$–$C_6$ cycloalkyl group represented by $R^8$ are cyclopropyl, cyclobutyl, cyclopentyl and cyclohexyl.

Examples of the $C_5$–$C_6$ cycloalkenyl are 1-cyclopentenyl, 2-cyclopentenyl, 3-cyclopentenyl, 1-cyclohexenyl, 2-cyclohexenyl and 3-cyclohexenyl.

Examples of the ($C_1$–$C_2$ alkyl)aminocarbonyl group represented by $R^8$ are methylaminocarbonyl and ethylaminocarbonyl.

Examples of the [di($C_1$–$C_2$ alkyl)amino]carbonyl group represented by $R^8$ are dimethylaminocarbonyl, N-methyl-N-ethylaminocarbonyl and diethylaminocarbonyl.

The following are preferred examples of the present compound:

dihalopropene compounds wherein A is a 5- or 6-membered heterocyclic ring group containing at least one oxygen, sulfur or nitrogen and optionally substituted by $(R^8)_r$ (wherein $R^8$ is halogen, nitro, cyano, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, ($C_1$–$C_2$ alkyl)aminocarbonyl or [di($C_1$–$C_2$ alkyl)amino]carbonyl, or $R^8$ is phenyl, benzyl, phenoxy, benzyloxy or pyridyloxy, each of which is optionally substituted with halogen, $C_1$–$C_4$ alkyl, $C_1$–$C_3$ haloalkyl, $C_1$–$C_4$ alkoxy or $C_1$–$C_3$ haloalkoxy; and r is an integer of 0 to 7);

dihalopropene compounds wherein A is 2-pyridyl, 3-pyridyl, 4-pyridyl, 2-thienyl, 3-thienyl, 2-furanyl, 3-furanyl, 5-(1,3-thiazolyl), N-(1,2-dihydro-2-oxo)pyridino, 1,3-dioxolanyl, 1,4-benzodioxanyl, 2-pyrazyl, 2-benzothiazolyl, 2-benzoxazolyl, 2-benzimidazolyl, 2-quinoxalynyl, N-benzimidazolyl, 2-quinolyl, 3-quinolyl or N-phthalimido, each of which is optionally substituted with $(R^8)_r$ (wherein $R^8$ and r are each as defined above);

dihalopropene compounds wherein $R^2$ and $R^3$ are independently halogen or $C_1$–$C_3$ alkyl, and t is 0;

dihalopropene compounds wherein $R^2$ and $R^3$ are independently chlorine, bromine, methyl, ethyl or isopropyl, and t is 0;

dihalopropene compounds wherein $R^2$ and $R^3$ are both chlorine, and t is 0;

dihalopropene compounds wherein $R^2$ is chlorine, $R^3$ is methyl, and t is 0;

dihalopropene compounds wherein $R^2$ is ethyl, $R^3$ is methyl, and t is 0;

dihalopropene compounds wherein $R^2$ and $R^3$ are both bromine, and t is 0;

dihalopropene compounds wherein $R^2$ and $R^3$ are both ethyl, and t is 0;

dihalopropene compounds wherein $R^2$ and $R^3$ are independently halogen or $C_1$–$C_3$ alkyl, t is 1 or 2, and $R^{10}$ is halogen or $C_1$–$C_3$ alkyl;

dihalopropene compounds wherein $R^2$ and $R^3$ are independently halogen or $C_1$–$C_3$ alkyl, t is 1 or 2, and $R^{10}$ is halogen;

dihalopropene compounds wherein Y and Z are both oxygen;

dihalopropene compounds wherein $R^1$ is $Q_1$ p is 1 to 6, and A is 2-pyridyl, 3-pyridyl, 4-pyridyl, 2-thienyl, 3-thienyl, 2-furanyl, 3-furanyl, 5-(1,3-thiazolyl), N-(1,2-dihydro-2-oxo)pyridino, 1,3-dioxolanyl or N-phthalimido, each of which is optionally substituted with $(R^8)_r$ (wherein $R^8$ and r are each as defined above);

dihalopropene compounds wherein $R^1$ is $Q_1$, p is 1 to 6, $R^5$, $R^6$ and $R^7$ are all hydrogen, and A is 1,3-dioxolanyl optionally substituted with $(R^8)_r$ (wherein $R^8$ and r are each as defined above);

dihalopropene compounds wherein $R^1$ is $Q_1$, p is 1 to 4, $R^5$, $R^6$ and R are all hydrogen, and A is 1,3-dioxolanyl optionally substituted with $(R^8)_r$ (wherein $R^8$ and r are each as defined above);

dihalopropene compounds wherein $R^1$ is $Q_1$, p is 0, and A is 2-pyridyl, 4-pyridyl, 2-thienyl, 3-thienyl, 2-furanyl, 3-furanyl, 5-(1,3-thiazolyl), 1,3-dioxolanyl or 1,4-benzodioxolanyl, each of which is optionally substituted with $(R^8)_r$ (wherein $R^8$ and r are each as defined above);

dihalopropene compounds wherein $R^1$ is $Q_2$;

dihalopropene compounds wherein $R^1$ is $Q_2$, and A is 2-pyridyl, 3-pyridyl, 4-pyridyl, 2-thienyl, 3-thienyl, 2-furanyl, 3-furanyl, 5-(1,3-thiazolyl), 2-pyradyl, 2-benzothiazolyl, 2-benzoxazolyl, 2-benzimidazolyl, 2-quinoxalynyl, N-benzimidazolyl, 2-quinolynyl or 3-quinolyl, each of which is optionally substituted with $(R^8)_r$ (wherein $R^8$ and r are each as defined above);

dihalopropene compounds wherein $R^1$ is $Q_2$, p is 1 to 4, and A is 2-pyridyl optionally substituted with $(R^8)_r$ (wherein $R^8$ and r are each as defined above);

dihalopropene compounds wherein $R^1$ is $Q_2$, p is 1 to 4, $R^5$, $R^6$ and $R^7$ are all hydrogen, and A is 2-pyridyl optionally substituted with $(R^8)_r$ (wherein $R^8$ and r are each as defined above);

dihalopropene compounds wherein $R^1$ is $Q_2$, p is 1 to 4, $R^5$, $R^6$ and $R^7$ are all hydrogen, A is 2-pyridyl optionally substituted with $(R^8)_r$ (wherein $R^8$ is halogen or $C_1$–$C_3$ haloalkyl and r is as defined above);

dihalopropene compounds wherein $R^1$ is $Q_2$, p is 2 or 3, $R^5$, $R^6$ and $R^7$ are all hydrogen, A is 2-pyridyl optionally substituted with $(R^8)_r$ (wherein $R^8$ is halogen or $C_1$–$C_3$ haloalkyl and r is as defined above);

dihalopropene compounds wherein $R^1$ is $Q_2$, p is 2 or 3, $R^5$, $R^6$ and $R^7$ are all hydrogen, A is 2-pyridyl optionally substituted with $(R^8)_r$ (wherein $R^8$ is halogen or trifluoromethyl and r is as defined above); and dihalopropene compounds wherein $R^1$ is $Q_2$, p is 2 or 3, $R^5$, $R^6$ and $R^7$ are all hydrogen, B is oxygen, A is 2-pyridyl optionally substituted with $(R^8)_r$ (wherein $R^8$ is halogen or trifluoromethyl and r is as defined above).

The following are particularly preferred examples of the present compound wherein numbers in parentheses are the corresponding compound numbers used below.

(36) 3,5-Dichloro-4-(3-(5-trifluoromethyl-2-pyridyloxy)propyloxy)-1-(3,3-dichloro-2-propenyloxy)benzene;

(47) 3-Ethyl-5-methyl-4-(3-(5-trifluoromethyl-2-pyridyloxy)propyloxy)-1-(3,3-dichloro-2-propenyloxy)benzene; and

(49) 3,5-Dichloro-4-(3-(5-trifluoromethyl-2-pyridyloxy)propyloxy)-1-(3,3-dichloro-2-propenyloxy)benzene.

The present compounds can be produced, for example by the following production processes A–H.

(Production Process A)
In this process, a compound of the general formula:

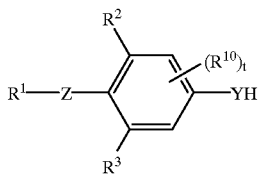
[III]

wherein $R^1$, $R^2$, $R^3$, $R^{10}$, t, Y and Z are each as defined above, is reacted with a halide compound of the general formula:

L—CH$_2$CH=CX$_2$ [IV]

wherein X is as defined above and L is halogen (e.g., chlorine, bromine, iodine), mesyloxy or tosyloxy.

The reaction is preferably effected in an inert solvent in the presence of a suitable base.

Examples of solvent that can be used are ketones such as acetone, methyl ethyl ketone and cyclohexanone; ethers such as 1,2-dimethoxyethane, tetrahydrofuran, dioxane and dialkyl (e.g., $C_1$–$C_4$) ether (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$), such as sodium methoxide, sodium ethoxide and potassium tert-butoxide; and organic bases such as triethylamine and pyridine. If necessary, catalysts such as ammonium salts (e.g., triethylbenzylammonium chloride) may be added to the reaction system at a ratio of 0.01 to 1 mole per mole of the compound of the general formula [III].

The reaction temperature is usually set within the range of –20° C. to 150° C. or the boiling point of a solvent used in the reaction, preferably –5° C. to 100° C. or the boiling point of a solvent used in the reaction.

The molar ratio of the starting materials and bases to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out, if necessary, by an ordinary technique such as chromatography, distillation or recrystallization.

(Production Process B for the Present Compounds wherein Y is Oxygen)

In this process, a compound of the general formula [III] is reacted with an alcohol compound of the general formula:

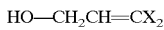
HO—CH$_2$CH=CX$_2$ [V]

wherein X is as defined above.

The reaction is preferably effected in an inert solvent, if necessary, in the presence of a suitable dehydrating agent.

Examples of the dehydrating agent which can be used are dicyclohexyl-carbodiimide, and dialkyl (e.g., $C_1$–$C_4$) azodicarboxylates (e.g., diethylazodicarboxylate, diisopropylazodicarboxylate)-trialkyl (e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of –20° C. to 200° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process C for the Present Compounds wherein Y is Oxygen)

In this process, an aldehyde compound of the general formula:

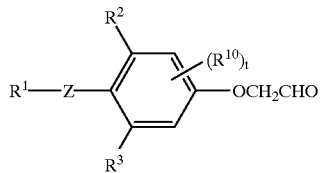
[VI]

wherein $R^1$, $R^2$, $R^3$, $R^{10}$, t and Z are each as defined above, is reacted with carbon tetrachloride or carbon tetrabromide.

The reaction is preferably effected in an inert solvent in the presence of a suitable trialkylphosphine or triarylphosphine, and if necessary, in the presence of metal zinc.

Examples of the solvent which can be used are hydrocarbons such as benzene, xylene and toluene; ethers such as diethyl ether, diisopropyl ether, tetrahydrofuran and dioxane; and halogenated hydrocarbons (exclusive of carbon tetrabromide and carbon tetrachloride) such as dichloromethane, 1,2-dichloroethane and chlorobenzene.

The reaction temperature is usually set within the range of –30° C. to 150° C. or the boiling point of a solvent used in the reaction.

Examples of the trialkyl (e.g., $C_1$–$C_{20}$) phosphine or triarylphosphine are triphenylphosphine and trioctylphosphine. The metal zinc which is used, if necessary, is preferably in dust form.

The molar ratio of the starting materials and reagents to be used in the reaction can be freely determined, but the ratio is preferably such that carbon tetrabromide or tetrachloride, trialkylphosphine or triarylphosphine, and zinc are 2 moles, 2 or 4 moles (2 moles when zinc is used), and 2 moles, respectively, per mole of the aldehyde compound of the general formula [VI], or it is favorable to effect the reaction at a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process D for the Present Compounds wherein Y and Z are both Oxygen)

In this process, a compound of the general formula:

[VII]

$$HO-\underset{R^3}{\underset{|}{\overset{R^2}{\overset{|}{\bigcirc}}}}(R^{10})_t - O-CH_2CH=CX_2$$

wherein $R^2$, $R^3$, $R^{30}$, t and X are each as defined above, is reacted with a compound of the general formula:

$R^1$—L    [VIII]

wherein $R^1$ and L are each as defined above.

The reaction is preferably effected in an inert solvent in the presence of a suitable base.

Examples of the solvent which can be used are ketones such as acetone, methyl ethyl ketone and cyclohexanone; ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine. If necessary, catalysts such as ammonium salts (e.g., triethylbenzylammonium chloride) may be added to the reaction system at a ratio of 0.01 to 1 mole per mole of the compound of the general formula [VII].

The reaction temperature is usually set within the range of −20° C. to 150° C. or the boiling point of a solvent used in the reaction, preferably −5° C. to 100° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process B for the Present Compounds wherein Y and Z are both Oxygen)

In this process, a compound of the general formula [VII] is reacted with an alcohol compound of the general formula:

$R^1$—OH    [IX]

wherein $R^1$ is as defined above.

The reaction is preferably effected in an inert solvent, if necessary, in the presence of a suitable dehydrating agent.

Examples of the dehydrating agent which can be used are dicyclohexyl-carbodiimide, and dialkyl (e.g., $C_1$–$C_4$) azodicarboxylates (e.g., diethylazodicarboxylate, diisopropylazodicarboxylate)-trialkyl (e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of −20° C. to 200° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process F for the Present Compounds wherein Y and Z are Both Oxygen, $R^1$ is $Q_2$ or $Q_3$, and B is $B^1$ (wherein $B^1$ is oxygen, sulfur or $NR^9$ [wherein $R^9$ is as defined above]))

In this process, a compound of the general formula:

[X]

$$HB^1\!\!\left[\begin{array}{c}R^5\\|\\C\\|\\R^6\end{array}\right]_p\!\!\begin{array}{c}R^7\\|\\CH\end{array}\!\!-O-\underset{R^3}{\underset{|}{\overset{R^2}{\overset{|}{\bigcirc}}}}(R^{10})_t-O-CH_2CH=CX_2$$

wherein $B^1$, $R^2$, $R^3$, $R^5$, $R^6$, $R^7$, $R^{10}$, p, t and X are each as defined above, is reacted with a compound of the general formula:

[XI]

$$A-L \text{ or } A\!\!-\!\!\left[\begin{array}{c}R^{11}\\|\\C\\|\\R^{12}\end{array}\right]_s\!\!-L$$

wherein A, $R^{11}$, $R^{12}$, L and s are each as defined above.

The reaction is preferably effected in an inert solvent in the presence of a suitable base.

Examples of the solvent which can be used are ketones such as acetone, methyl ethyl ketone and cyclohexanone;

ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine. If necessary, catalysts such as ammonium salts (e.g., triethylbenzylammonium chloride) may be added to the reaction system at a ratio of 0.01 to 1 mole per mole of the compound of the general formula [X].

The reaction temperature is usually set within the range of −20° C. to 150° C. or the boiling point of a solvent used in the reaction, preferably −5° C. to 100° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process G for the Present Compounds wherein Y, Z and B are all Oxygen and $R^1$ is $Q_2$, $Q_3$, $Q_6$ or $Q_7$)

In this process, an alcohol compound of the general formula:

[XII]

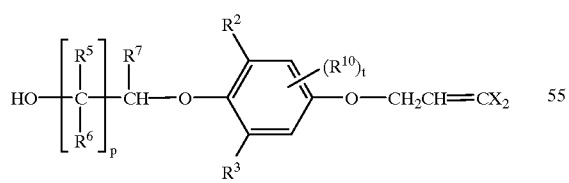

wherein $R^2$, $R^3$, $R^{10}$, $R^5$, $R^6$, $R^7$, p, t and X are each as defined above, is reacted with compound $Q_{21}$, $Q_{31}$, $Q_{61}$ or $Q_{71}$ of the general formula:

$Q_{21}$

A—OH, $Q_{31}$

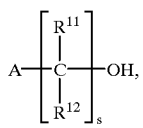

$Q_{61}$

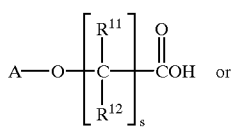

$Q_{71}$

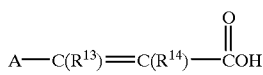

wherein $R^{11}$, $R^{12}$, $R^{13}$, $R^{14}$, A and s are each as defined above.

The reaction is preferably effected in an inert solvent, if necessary, in the presence of a suitable dehydrating agent.

Examples of the dehydrating agent which can be used are dicyclohexyl-carbodiimide, and dialkyl (e.g., $C_1$–$C_4$) azodicarboxylates (e.g., diethylazodicarboxylate, diisopropylazodicarboxylate)-trialkyl (e.g., $C_1$–$C_{20}$) phosphine or triarylphosphine (e.g., triphenylphosphine, trioctylphosphine, tributylphosphine).

Examples of the solvent which can be used are hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of −20° C. to 200° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

(Production Process H for the Present Compounds wherein Y and Z are Both Oxygen and $R^1$ is $Q_2$, $Q_3$, $Q_6$ or $Q_7$)

In this process, a compound of the general formula:

[XIII]

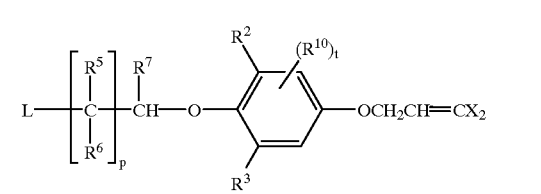

wherein $R^2$, $R^3$, $R^5$, $R^6$, $R^7$, $R^{10}$, X, L, p and t are each as defined above, is reacted with compound $Q_{22}$, $Q_{32}$, $Q_{62}$ or $Q_{72}$ of the general formula:

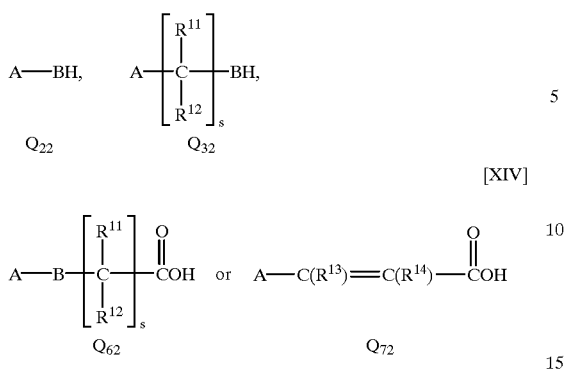

wherein $R^{11}$, $R^{12}$, $R^{13}$, $R^{14}$, A, B and s are each as defined above.

The reaction is preferably effected in an inert solvent in the presence of a suitable base.

Examples of the solvent which can be used are ketones such as acetone, methyl ethyl ketone and cyclohexanone; ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used are hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine. If necessary, catalysts such as ammonium salts (e.g., triethylbenzylammonium chloride) may be added to the reaction system at a ratio of 0.01 to 1 mole per mole of the compound of the general formula [XIV].

The reaction temperature is usually set within the range of −20° C. to 150° C. or the boiling point of a solvent used in the reaction, preferably −5° C. to 100° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Further, purification can be carried out by an ordinary technique such as chromatography, distillation or recrystallization.

When the present compound has an asymmetry carbon atom, it is to be construed to include its optically active isomers ((+)-form and (−)-form) having biological activity and their mixtures at any ratio. When the present compound exhibits geometrical isomerism, it is to be construed to include its geometrical isomers (cis-form and trans-form) and their mixtures at any ratio.

The following are typical examples of the present compound (wherein $R^1$ is as shown in Tables 1 to 46), which are not to be construed to limit the scope of the present invention.

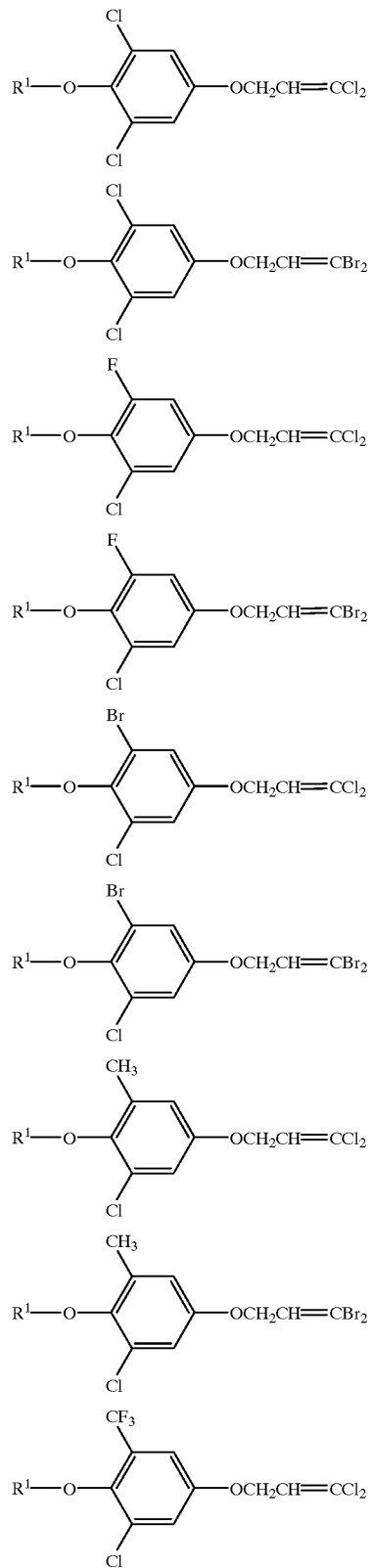

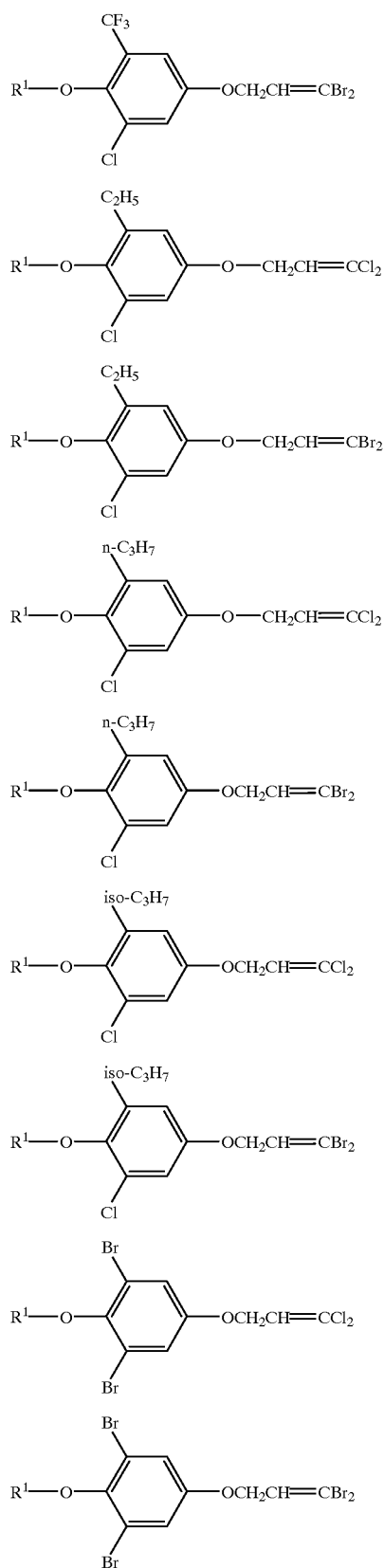
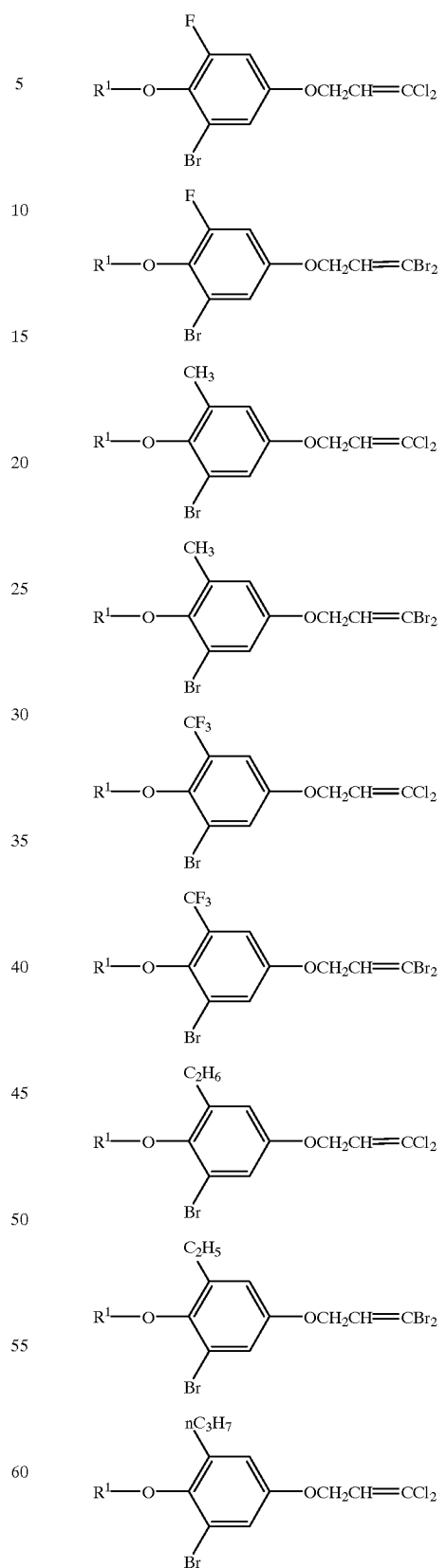

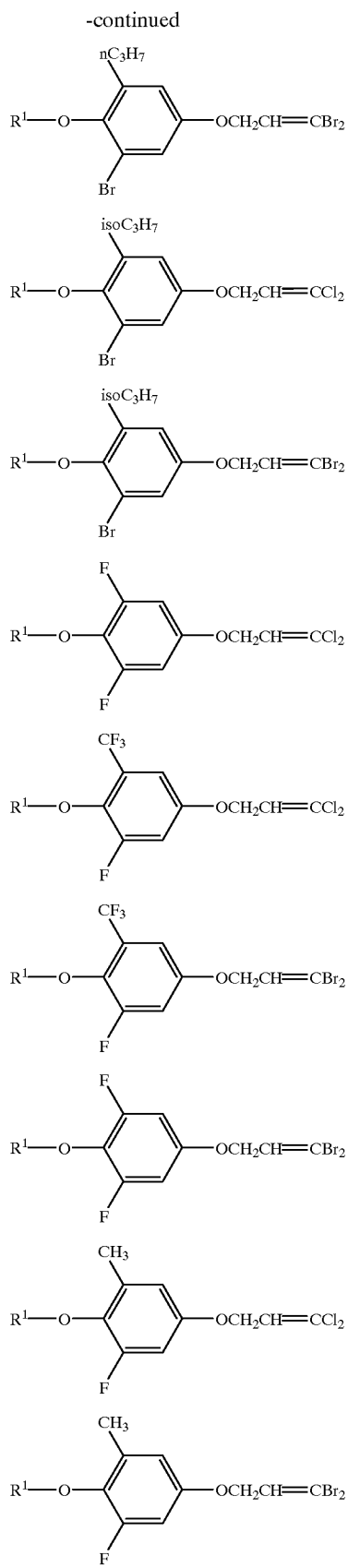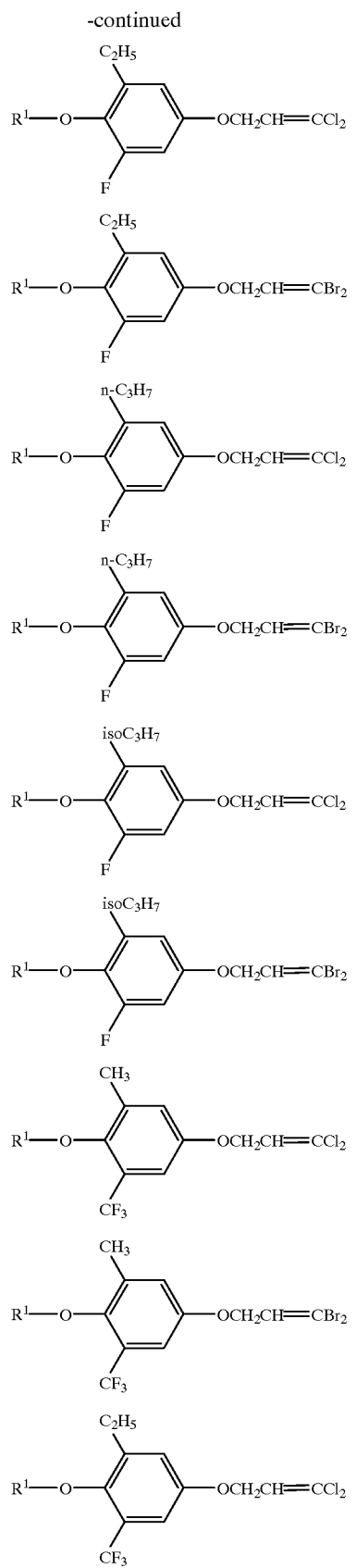

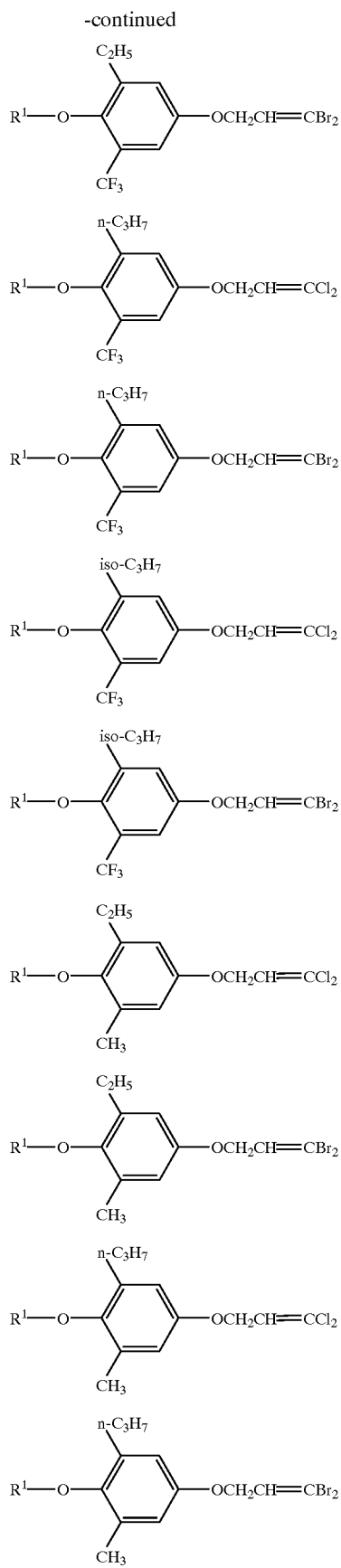
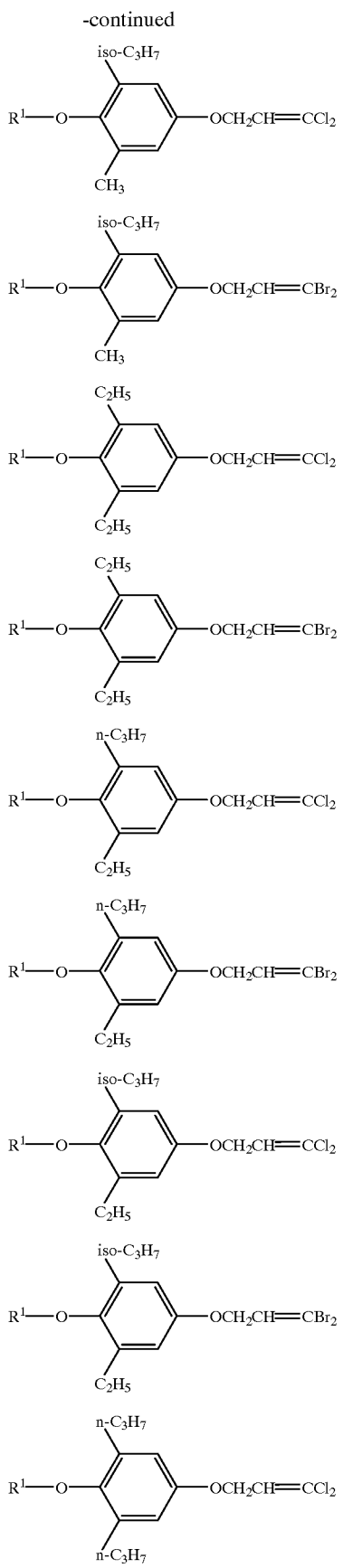

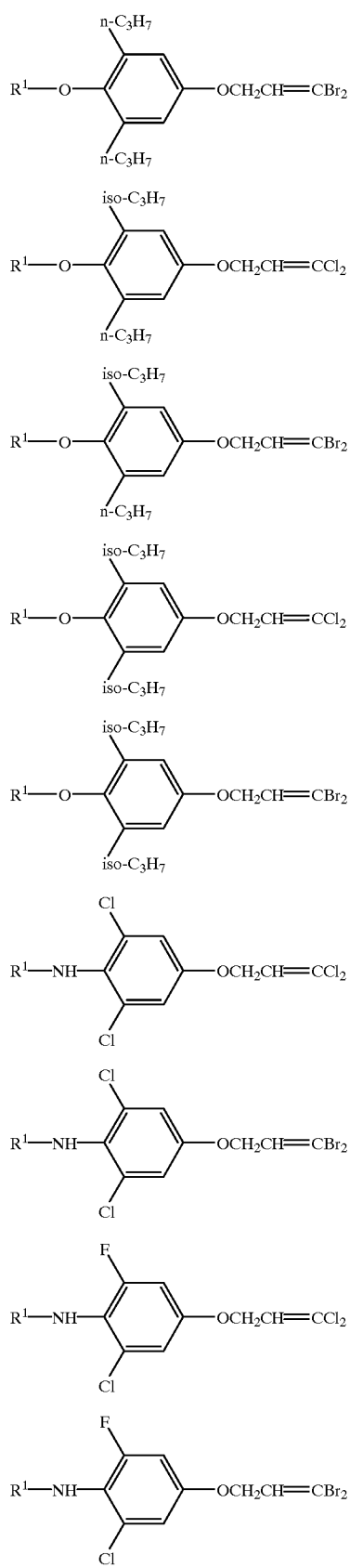
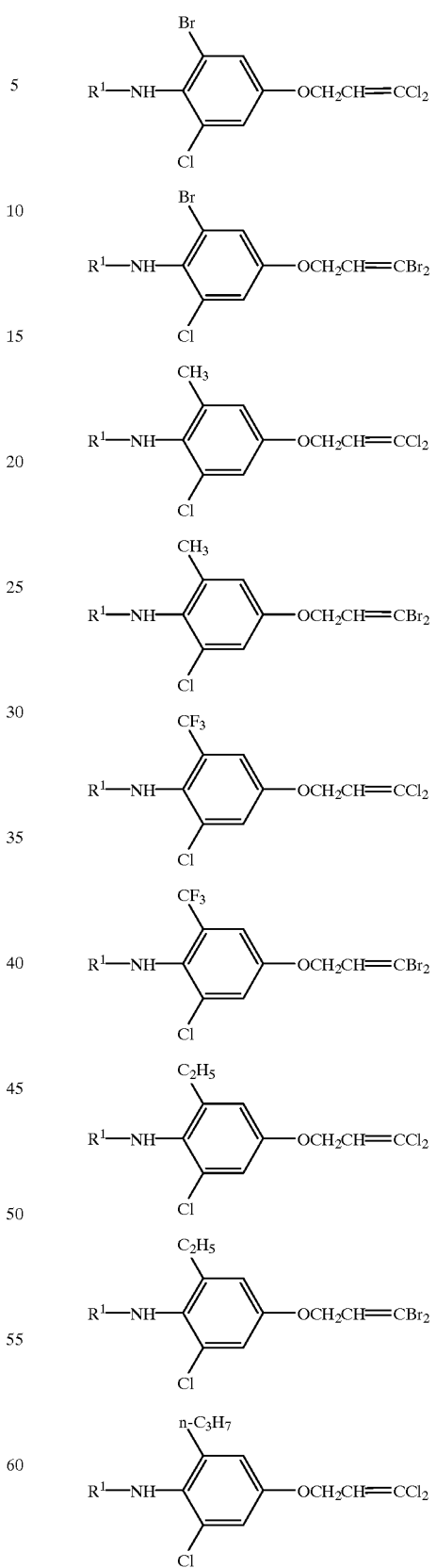

-continued
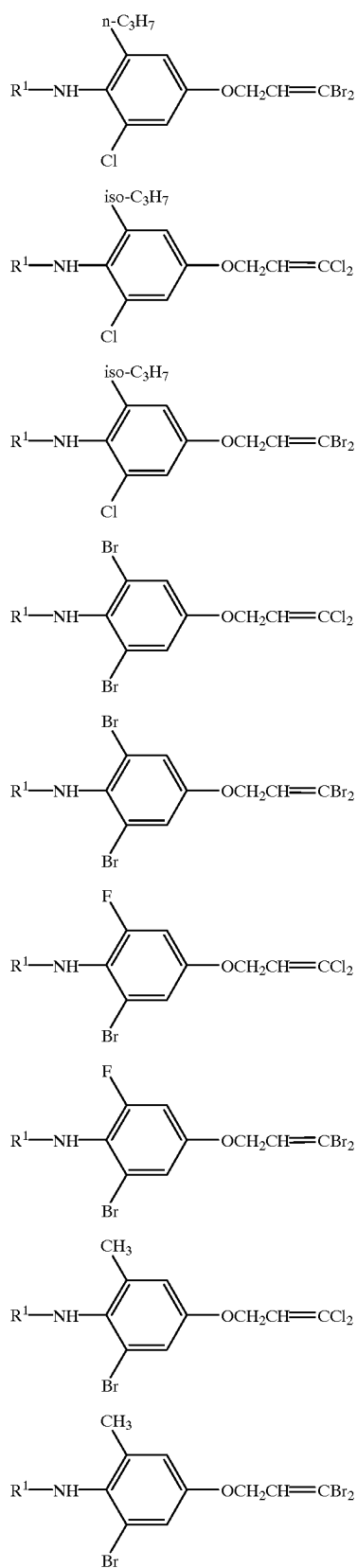
-continued
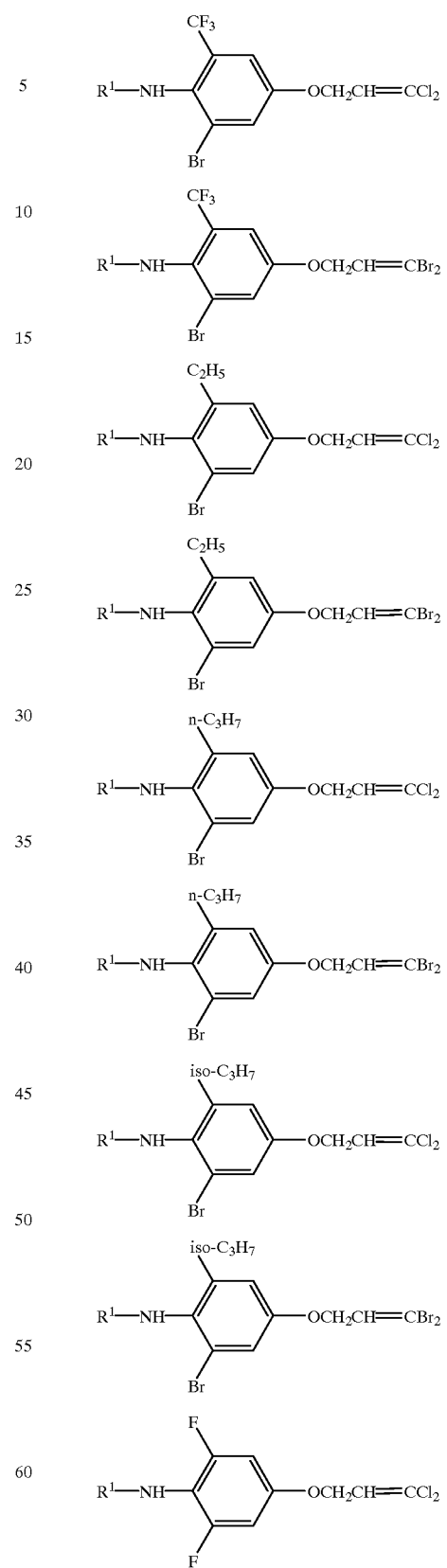

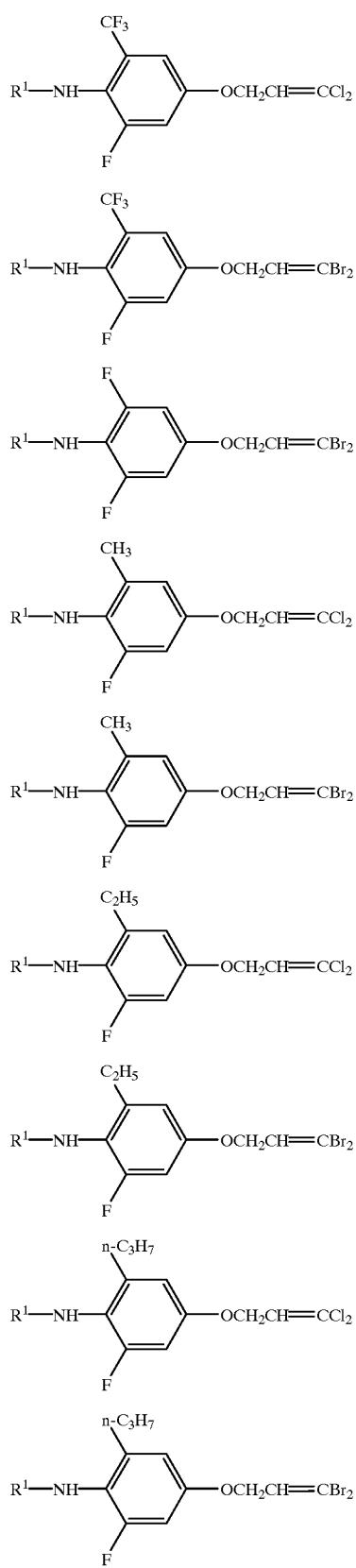
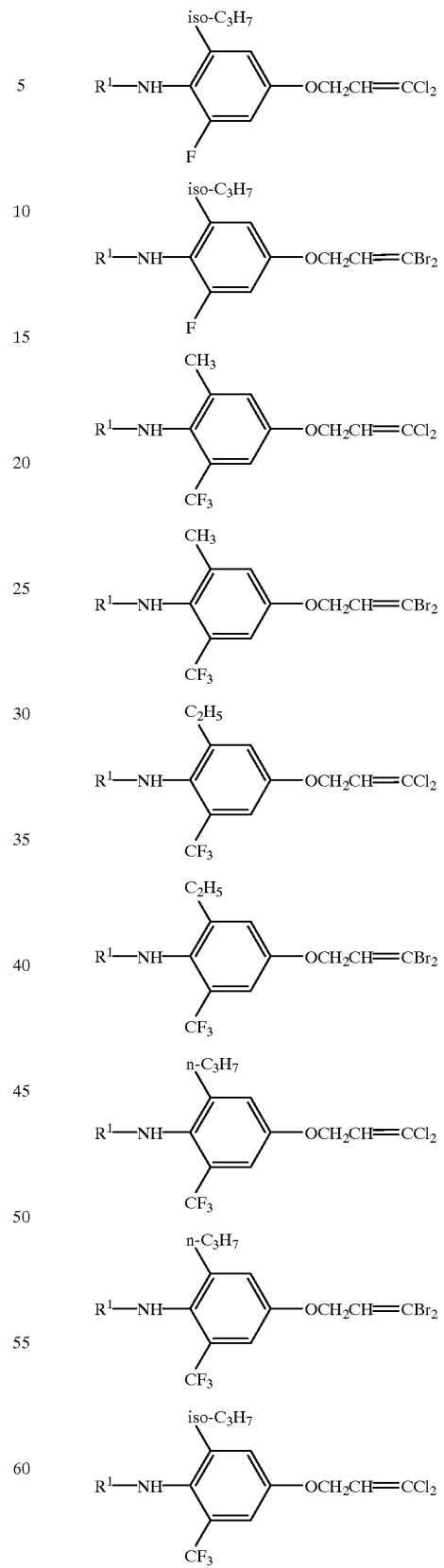

-continued
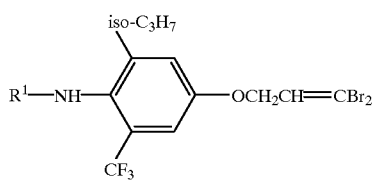
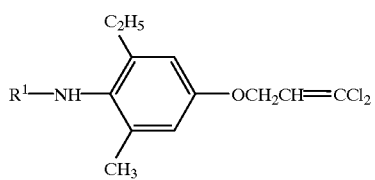
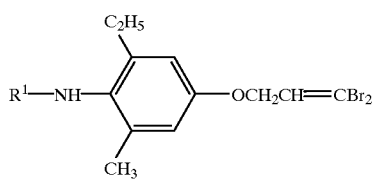
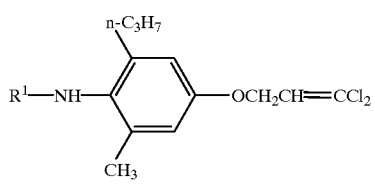
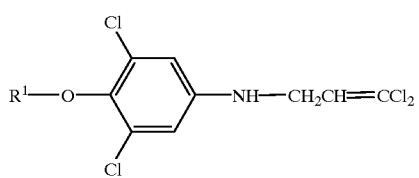
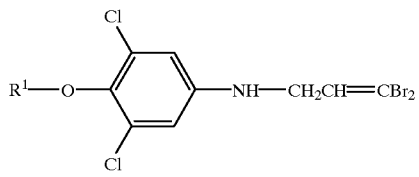
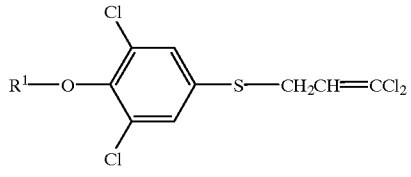
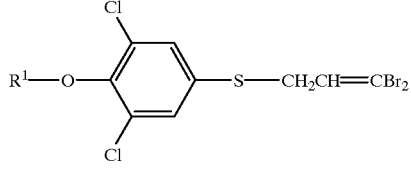
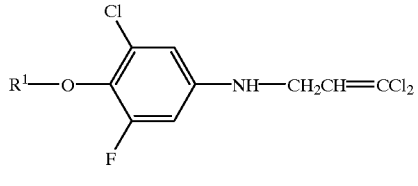
-continued
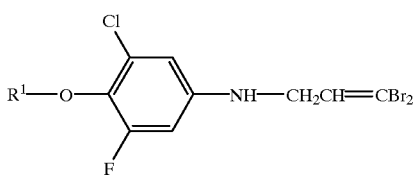
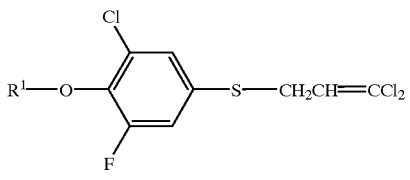
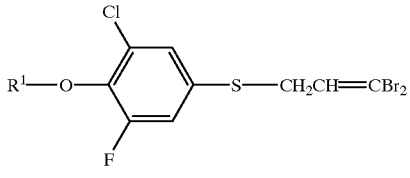
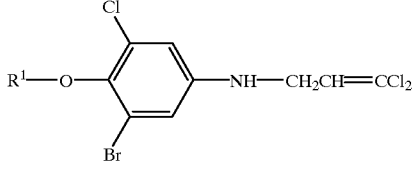
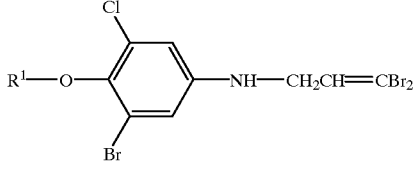
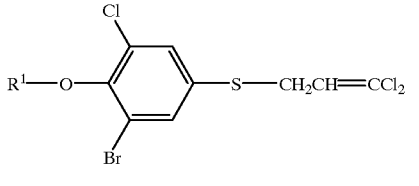
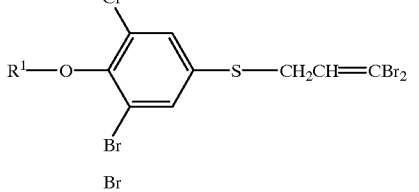
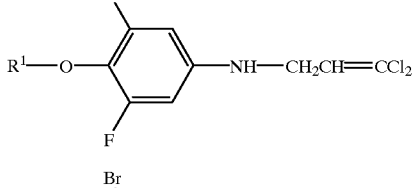
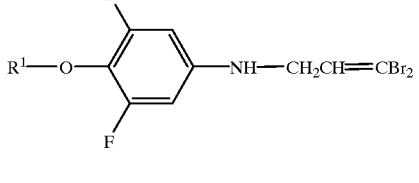

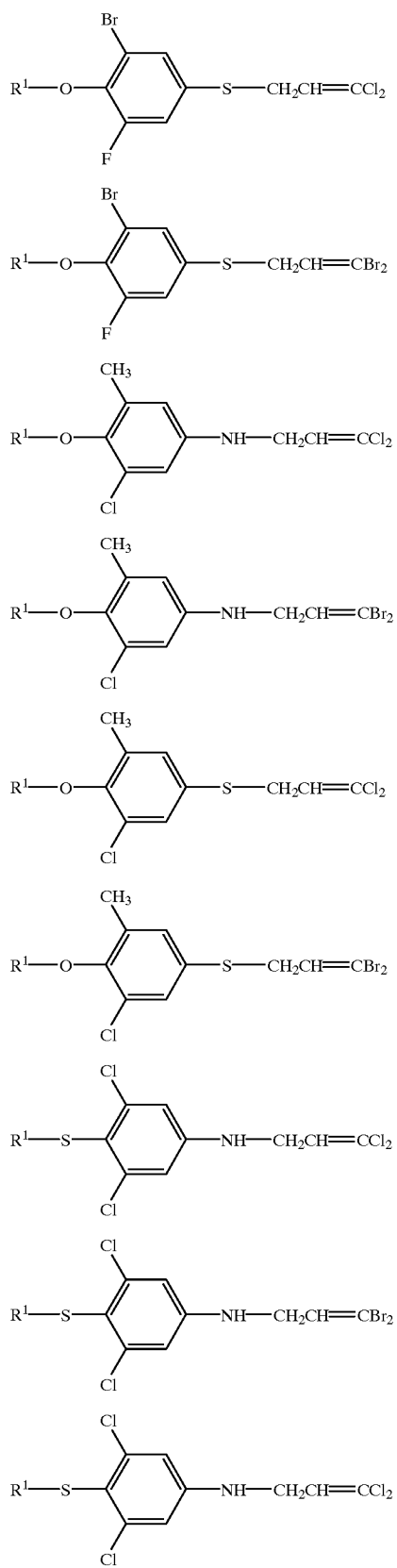
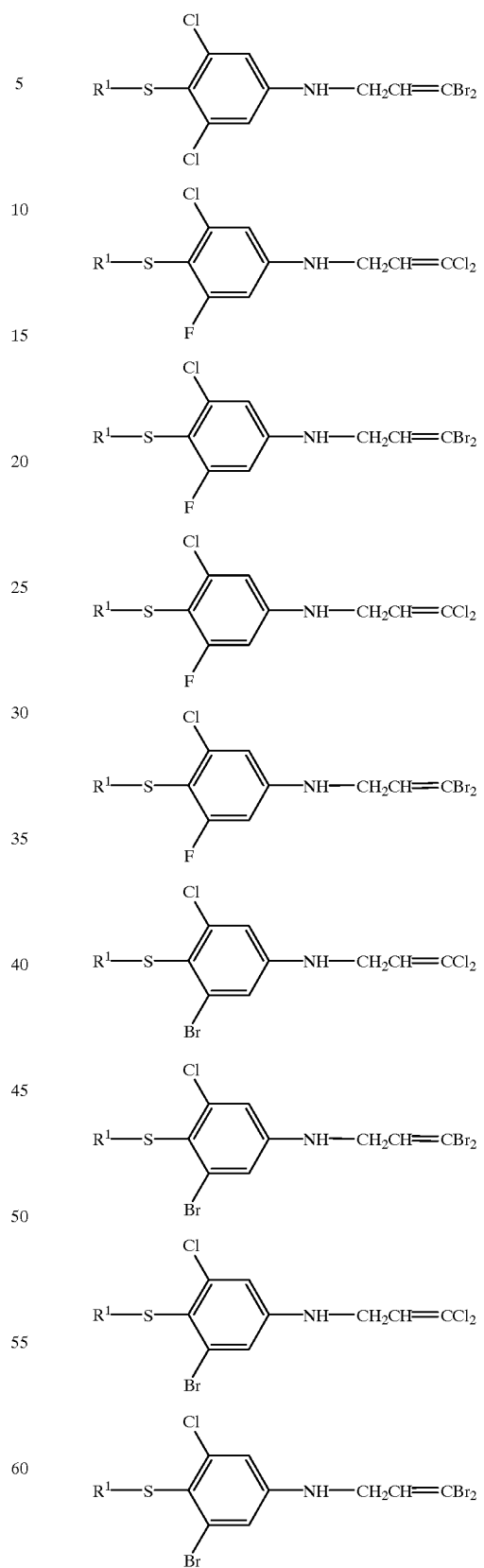

-continued
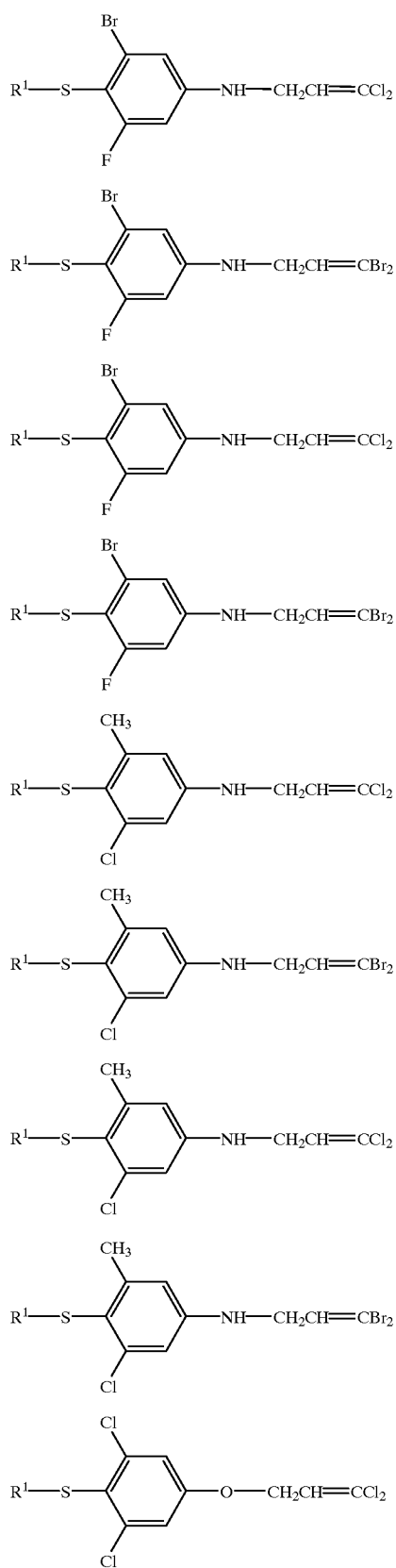
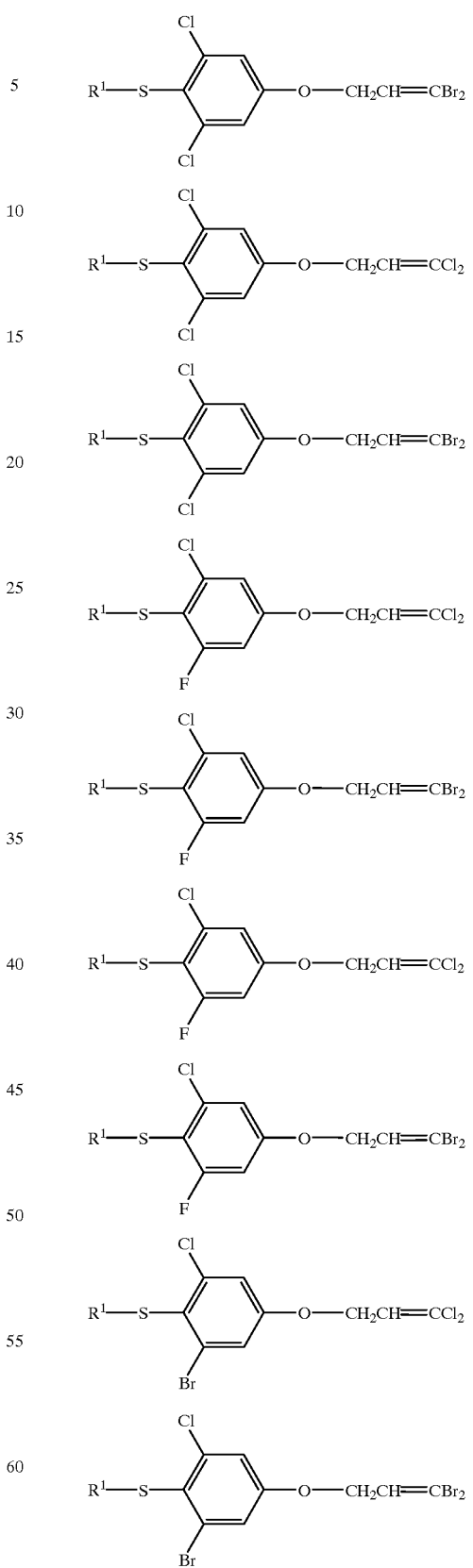

-continued
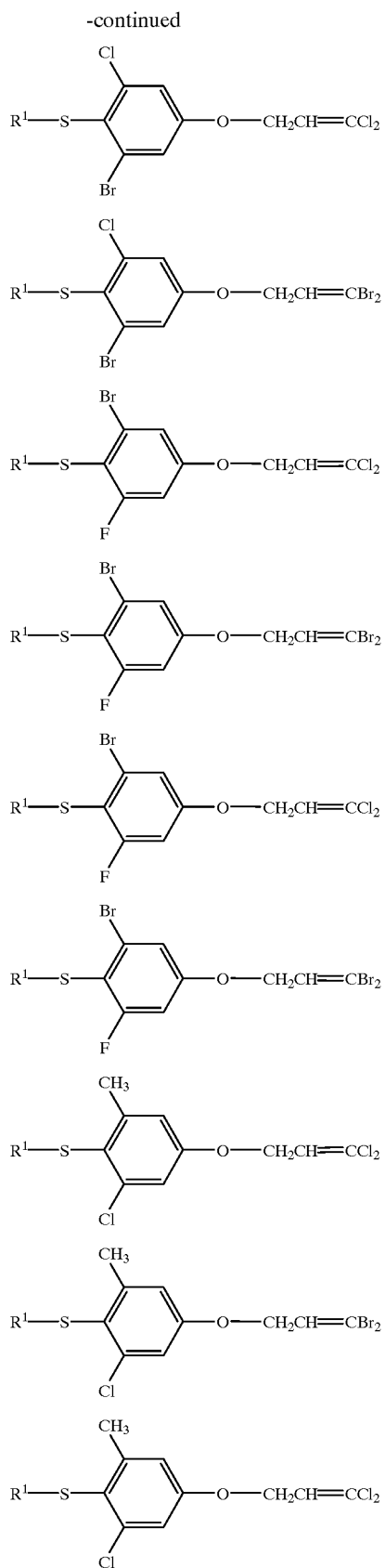
-continued
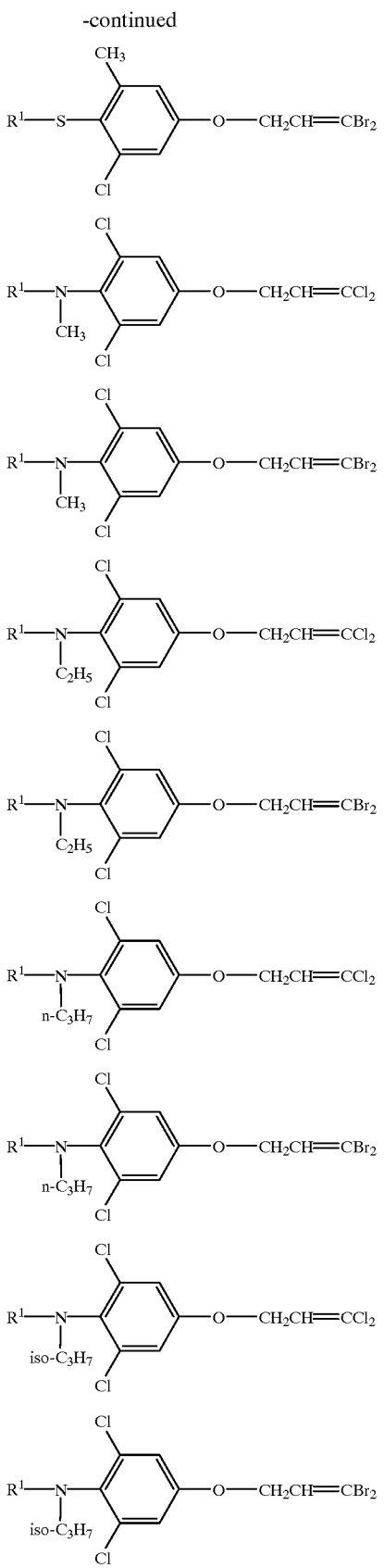

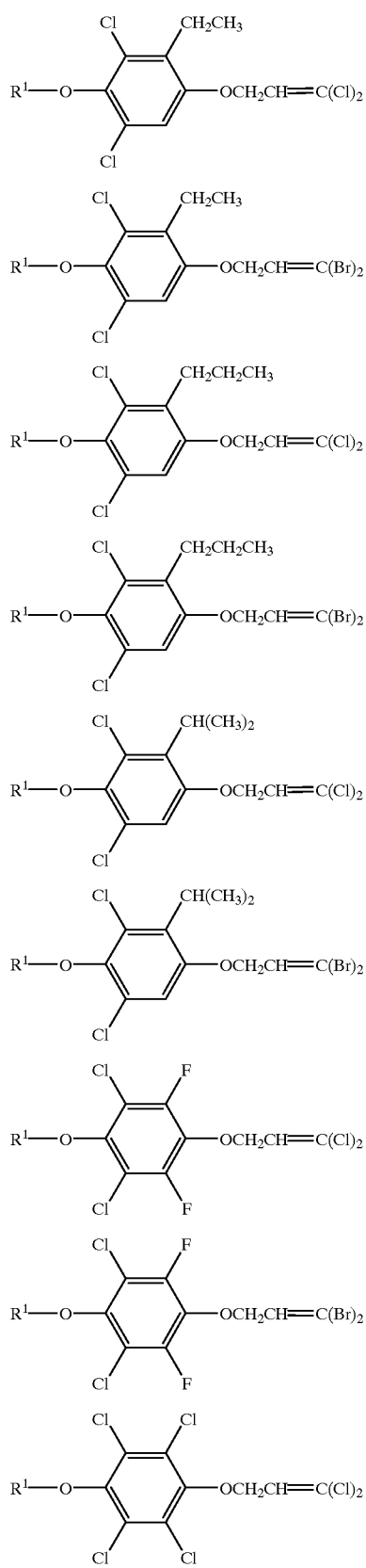
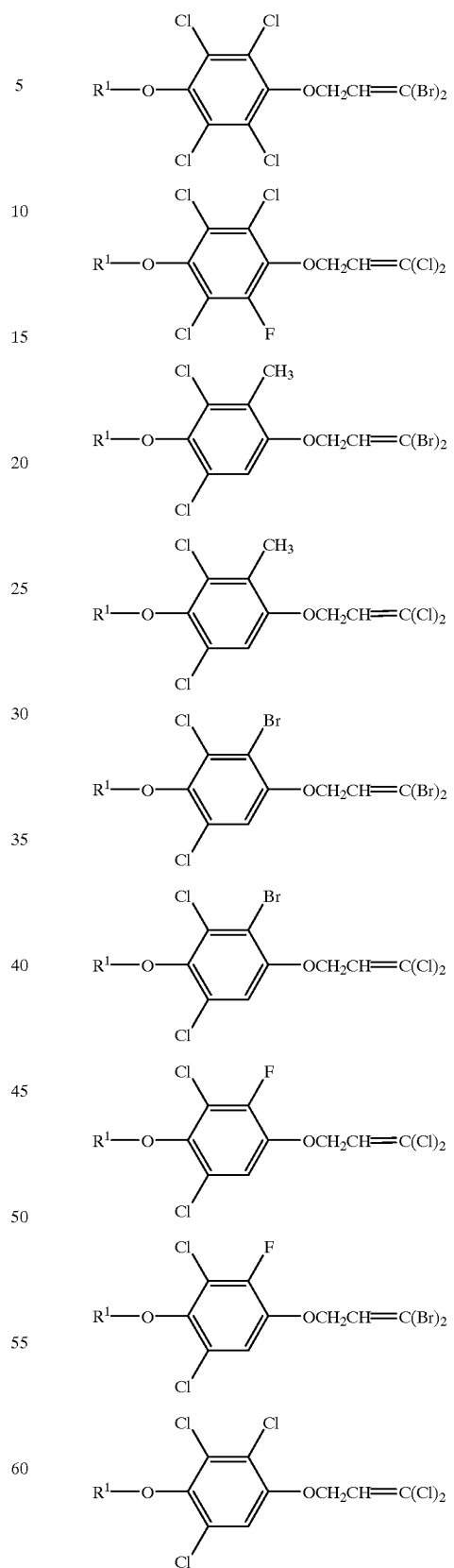

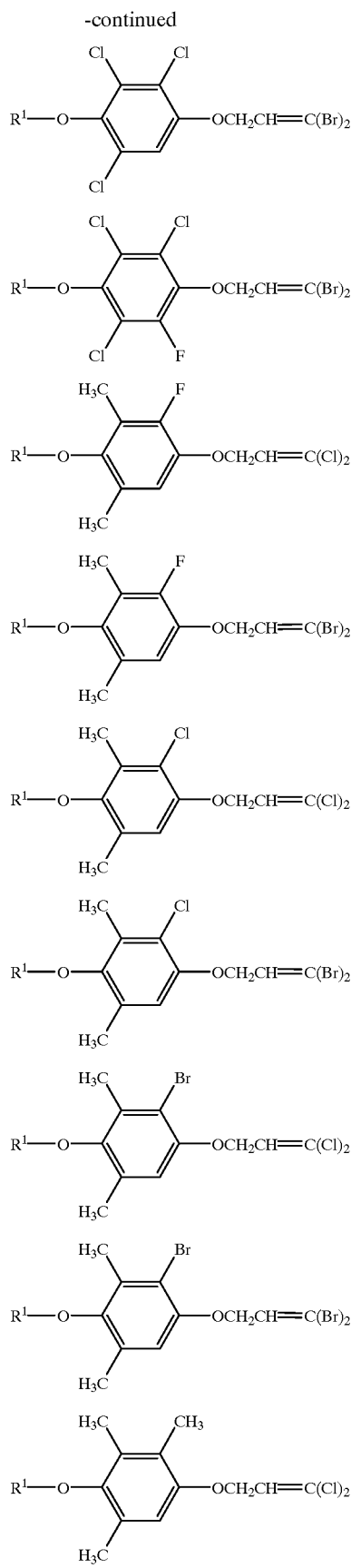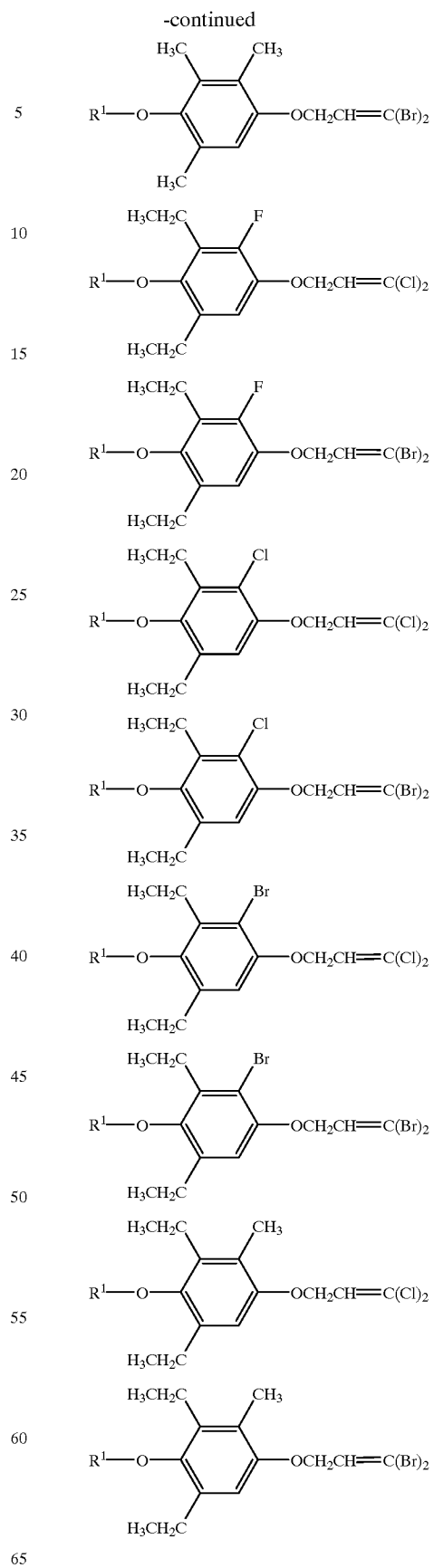

TABLE 1

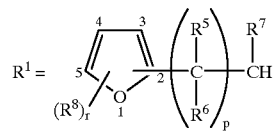

| Bonding position of heterocyclic ring | R⁵ | R⁶ | R⁷ | p | (R⁸)ᵣ |
|---|---|---|---|---|---|
| 2 | H | H | H | 0 | H |
| 2 | H | H | H | 1 | H |
| 2 | H | H | H | 2 | H |
| 2 | H | H | H | 3 | H |
| 2 | H | H | H | 4 | H |
| 2 | H | H | H | 5 | H |
| 2 | H | H | H | 6 | H |
| 2 | H | H | H | 0 | 5-CH₃ |
| 2 | H | H | H | 1 | 5-CH₃ |
| 2 | H | H | H | 2 | 5-CH₃ |
| 2 | H | H | H | 3 | 5-CH₃ |
| 2 | H | H | H | 4 | 5-CH₃ |
| 2 | H | H | H | 5 | 5-CH₃ |
| 2 | H | H | H | 6 | 5-CH₃ |
| 2 | H | H | H | 0 | 5-CH₂OCH₃ |
| 2 | H | H | H | 1 | 5-CH₂OCH₃ |
| 2 | H | H | H | 2 | 5-CH₂OCH₃ |
| 2 | H | H | H | 3 | 5-CH₂OCH₃ |
| 2 | H | H | H | 4 | 5-CH₂OCH₃ |
| 2 | H | H | H | 0 | 5-CH₂CH₃ |
| 2 | H | H | H | 1 | 5-CH₂CH₃ |
| 2 | H | H | H | 2 | 5-CH₂CH₃ |
| 2 | H | H | H | 3 | 5-CH₂CH₃ |
| 2 | H | H | H | 4 | 5-CH₂CH₃ |
| 2 | H | H | H | 5 | 5-CH₂CH₃ |
| 2 | H | H | H | 6 | 5-CH₂CH₃ |
| 2 | H | H | CH₃ | 0 | H |
| 2 | H | H | CH₃ | 0 | 5-CH₃ |
| 2 | H | H | H | 0 | 5-CHO |
| 2 | H | H | H | 1 | 5-CHO |
| 2 | H | H | H | 2 | 5-CHO |
| 2 | H | H | H | 3 | 5-CHO |
| 2 | H | H | H | 4 | 5-CHO |
| 2 | H | H | H | 5 | 5-CHO |
| 2 | H | H | H | 6 | 5-CHO |
| 2 | H | H | H | 0 | 5-NO₂ |
| 2 | H | H | H | 1 | 5-NO₂ |
| 2 | H | H | H | 2 | 5-NO₂ |
| 2 | H | H | H | 3 | 5-NO₂ |
| 2 | H | H | H | 4 | 5-NO₂ |
| 2 | H | H | H | 5 | 5-NO₂ |
| 2 | H | H | H | 6 | 5-NO₂ |
| 2 | H | H | H | 0 | 3-CO₂CH₃ |
| 3 | H | H | H | 0 | H |
| 3 | H | H | H | 1 | H |
| 3 | H | H | H | 2 | H |
| 3 | H | H | H | 3 | H |
| 3 | H | H | H | 4 | H |
| 3 | H | H | H | 5 | H |
| 3 | H | H | H | 6 | H |
| 3 | H | H | H | 0 | 2-CH₃ |
| 3 | H | H | H | 1 | 2-CH₃ |
| 3 | H | H | H | 2 | 2-CH₃ |
| 3 | H | H | H | 3 | 2-CH₃ |
| 3 | H | H | H | 4 | 2-CH₃ |
| 3 | H | H | H | 5 | 2-CH₃ |
| 3 | H | H | H | 6 | 2-CH₃ |
| 3 | H | H | H | 0 | 2,5-(CH₃)₂ |
| 3 | H | H | H | 1 | 2,5-(CH₃)₂ |
| 3 | H | H | H | 2 | 2,5-(CH₃)₂ |
| 3 | H | H | H | 3 | 2,5-(CH₃)₂ |
| 3 | H | H | H | 4 | 2,5-(CH₃)₂ |
| 3 | H | H | H | 5 | 2,5-(CH₃)₂ |
| 3 | H | H | H | 6 | 2,5-(CH₃)₂ |
| 3 | H | H | H | 0 | 2,4-(CH₃)₂ |
| 3 | H | H | H | 1 | 2,4-(CH₃)₂ |

TABLE 1-continued

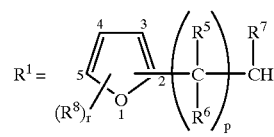

| Bonding position of heterocyclic ring | R⁵ | R⁶ | R⁷ | p | (R⁸)ᵣ |
|---|---|---|---|---|---|
| 3 | H | H | H | 2 | 2,4-(CH₃)₂ |
| 3 | H | H | H | 3 | 2,4-(CH₃)₂ |
| 3 | H | H | H | 4 | 2,4-(CH₃)₂ |
| 3 | H | H | H | 5 | 2,4-(CH₃)₂ |
| 3 | H | H | H | 6 | 2,4-(CH₃)₂ |

TABLE 2

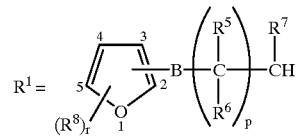

| Bonding position of heterocyclic ring | R⁵ | R⁶ | R⁷ | p | (R⁸)ᵣ | B |
|---|---|---|---|---|---|---|
| 2 | H | H | H | 1 | H | COO |
| 2 | H | H | H | 2 | H | COO |
| 2 | H | H | H | 3 | H | COO |
| 2 | H | H | H | 1 | 5-CH₃ | COO |
| 2 | H | H | H | 1 | 5-C₂H₅ | COO |
| 2 | H | H | H | 1 | 5-Br | COO |
| 2 | H | H | H | 2 | 5-CH₃ | COO |
| 2 | H | H | H | 2 | 5-C₂H₅ | COO |
| 2 | H | H | H | 2 | 5-Br | COO |
| 2 | H | H | H | 3 | 5-CH₃ | COO |
| 2 | H | H | H | 3 | 5-C₂H₅ | COO |
| 2 | H | H | H | 3 | 5-CH₃ | COO |
| 3 | H | H | H | 1 | H | COO |
| 3 | H | H | H | 2 | H | COO |
| 3 | H | H | H | 3 | H | COO |

TABLE 3

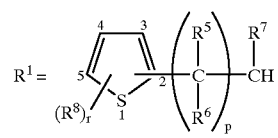

| Bonding position of heterocyclic ring | R⁵ | R⁶ | R⁷ | p | (R⁸)ᵣ |
|---|---|---|---|---|---|
| 2 | H | H | H | 0 | H |
| 2 | H | H | H | 1 | H |
| 2 | H | H | H | 2 | H |
| 2 | H | H | H | 3 | H |
| 2 | H | H | H | 4 | H |
| 2 | H | H | H | 5 | H |
| 2 | H | H | H | 6 | H |
| 2 | H | H | H | 0 | 5-CH₃ |
| 2 | H | H | H | 1 | 5-CH₃ |
| 2 | H | H | H | 2 | 5-CH₃ |

TABLE 3-continued $$R^1 = \underset{(R^8)_r}{\underset{S\ 1}{\overset{4\ \ \ 3}{\underset{2}{\bigg\langle}}}} \overset{R^5}{\underset{R^6}{\bigg(}C\bigg)_p} \overset{R^7}{\underset{}{CH}}$$

| Bonding position of heterocyclic ring | R⁵ | R⁶ | R⁷ | p | (R⁸)ᵣ |
|---|---|---|---|---|---|
| 2 | H | H | H | 3 | 5-CH₃ |
| 2 | H | H | H | 4 | 5-CH₃ |
| 2 | H | H | H | 5 | 5-CH₃ |
| 2 | H | H | H | 6 | 5-CH₃ |
| 2 | H | H | H | 0 | 5-Cl |
| 2 | H | H | H | 1 | 5-Cl |
| 2 | H | H | H | 2 | 5-Cl |
| 2 | H | H | H | 3 | 5-Cl |
| 2 | H | H | H | 4 | 5-Cl |
| 2 | H | H | H | 5 | 5-Cl |
| 2 | H | H | H | 6 | 5-Cl |
| 2 | H | H | H | 0 | 5-Br |
| 2 | H | H | H | 1 | 5-Br |
| 2 | H | H | H | 2 | 5-Br |
| 2 | H | H | H | 3 | 5-Br |
| 2 | H | H | H | 4 | 5-Br |
| 2 | H | H | H | 5 | 5-Br |
| 2 | H | H | H | 6 | 5-Br |
| 2 | H | H | H | 0 | 5-NO₂ |
| 2 | H | H | H | 1 | 5-NO₂ |
| 2 | H | H | H | 2 | 5-NO₂ |
| 2 | H | H | H | 3 | 5-NO₂ |
| 2 | H | H | H | 4 | 5-NO₂ |
| 2 | H | H | H | 5 | 5-NO₂ |
| 2 | H | H | H | 6 | 5-NO₂ |
| 2 | H | H | H | 0 | 5-NH₂ |
| 2 | H | H | H | 1 | 5-NH₂ |
| 2 | H | H | H | 2 | 5-NH₂ |
| 2 | H | H | H | 3 | 5-NH₂ |
| 2 | H | H | H | 4 | 5-NH₂ |
| 2 | H | H | H | 5 | 5-NH₂ |
| 2 | H | H | H | 6 | 5-NH₂ |
| 2 | H | H | H | 0 | 5-NHCOCH₃ |
| 2 | H | H | H | 1 | 5-NHCOCH₃ |
| 2 | H | H | H | 2 | 5-NHCOCH₃ |
| 2 | H | H | H | 3 | 5-NHCOCH₃ |
| 2 | H | H | H | 4 | 5-NHCOCH₃ |
| 2 | H | H | H | 5 | 5-NHCOCH₃ |
| 2 | H | H | H | 6 | 5-NHCOCH₃ |
| 2 | H | H | H | 0 | 5-NHCOCF₃ |
| 2 | H | H | H | 1 | 5-NHCOCF₃ |
| 2 | H | H | H | 2 | 5-NHCOCF₃ |
| 2 | H | H | H | 3 | 5-NHCOCF₃ |
| 2 | H | H | H | 4 | 5-NHCOCF₃ |
| 2 | H | H | H | 5 | 5-NHCOCF₃ |
| 2 | H | H | H | 6 | 5-NHCOCF₃ |
| 2 | H | H | CH₃ | 0 | 3-CH₃ |
| 2 | H | H | CH₃ | 0 | 5-Cl |
| 2 | H | H | CH₃ | 0 | 5-Br |
| 2 | H | H | CH₂CH₃ | 0 | H |
| 2 | H | H | H | 0 | 3-CH₃ |
| 2 | H | H | H | 1 | 3-CH₃ |
| 2 | H | H | H | 0 | 5-NH₂ |
| 2 | H | H | H | 2 | 3-CH₃ |
| 2 | H | H | H | 3 | 3-CH₃ |
| 2 | H | H | H | 4 | 3-CH₃ |
| 2 | H | H | H | 5 | 3-CH₃ |
| 2 | H | H | H | 6 | 3-CH₃ |
| 2 | H | H | H | 0 | 4-Br |
| 2 | H | H | H | 1 | 4-Br |
| 2 | H | H | H | 2 | 4-Br |
| 2 | H | H | H | 3 | 4-Br |
| 2 | H | H | H | 4 | 4-Br |
| 2 | H | H | H | 5 | 4-Br |
| 2 | H | H | H | 6 | 4-Br |
| 3 | H | H | H | 0 | H |
| 3 | H | H | H | 1 | H |
| 3 | H | H | H | 2 | H |
| 3 | H | H | H | 3 | H |
| 3 | H | H | H | 4 | H |
| 3 | H | H | H | 5 | H |
| 3 | H | H | H | 6 | H |
| 3 | H | H | CH₃ | 0 | H |
| 3 | H | H | CH₃ | 0 | 2,5-(CH₃)₂ |

TABLE 4

$$R^1 = \underset{(R^8)_r}{\underset{F\ 1}{\overset{4\ \ \ 3}{\underset{2}{\bigg\langle}}}} B \overset{R^5}{\underset{R^6}{\bigg(}C\bigg)_p} \overset{R^7}{\underset{}{CH}}$$

| Bonding position of heterocyclic ring | B | R⁵ | R⁶ | R⁷ | p | (R⁸)ᵣ | F |
|---|---|---|---|---|---|---|---|
| 3 | S | H | H | H | 0 | 2-CH₃ | O |
| 2 | SO₂ | H | H | H | 0 | H | S |
| 2 | SO₂ | H | H | H | 1 | H | S |
| 2 | SO₂ | H | H | H | 2 | H | S |
| 2 | SO₂ | H | H | H | 3 | H | S |
| 2 | SO₂ | H | H | H | 4 | H | S |
| 2 | SO₂ | H | H | H | 5 | H | S |
| 2 | SO₂ | H | H | H | 6 | H | S |
| 2 | COO | H | H | H | 2 | H | S |
| 2 | COO | H | H | H | 3 | H | S |
| 2 | COO | H | H | H | 4 | H | S |
| 3 | COO | H | H | H | 2 | H | S |
| 3 | COO | H | H | H | 3 | H | S |
| 3 | COO | H | H | H | 4 | H | S |
| 2 | COO | H | H | H | 2 | 5-CH₃ | S |
| 2 | COO | H | H | H | 3 | 5-CH₃ | S |
| 2 | COO | H | H | H | 4 | 5-CH₃ | S |

TABLE 5

$$R^1 = \underset{(R^8)_r}{\underset{O\ 1}{\overset{4\ \ \ 3}{\underset{2}{\bigg\langle}}}} \overset{R^5}{\underset{R^6}{\bigg(}C\bigg)_p} \overset{R^7}{\underset{}{CH}}$$

| Bonding position of heterocyclic ring | R⁵ | R⁶ | R⁷ | p | (R⁸)ᵣ |
|---|---|---|---|---|---|
| 2 | H | H | H | 0 | H |
| 2 | H | H | H | 1 | H |
| 2 | H | H | H | 2 | H |
| 2 | H | H | H | 3 | H |
| 2 | H | H | H | 4 | H |
| 2 | H | H | H | 5 | H |

TABLE 5-continued

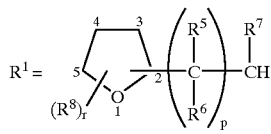

| Bonding position of heterocyclic ring | R⁵ | R⁶ | R⁷ | p | (R⁸)ᵣ |
|---|---|---|---|---|---|
| 2 | H | H | H | 6 | H |

TABLE 6

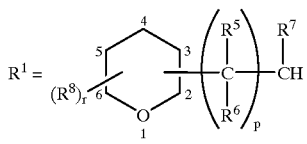

| Bonding position of heterocyclic ring | R⁵ | R⁶ | R⁷ | p | (R⁸)ᵣ |
|---|---|---|---|---|---|
| 2 | H | H | H | 0 | H |
| 2 | H | H | H | 1 | H |
| 2 | H | H | H | 2 | H |
| 2 | H | H | H | 3 | H |
| 2 | H | H | H | 4 | H |
| 2 | H | H | H | 5 | H |
| 2 | H | H | H | 6 | H |

TABLE 7

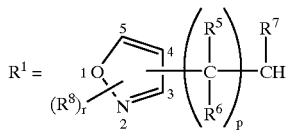

| Bonding position of heterocyclic ring | R⁵ | R⁶ | R⁷ | p | (R⁸)ᵣ |
|---|---|---|---|---|---|
| 3 | H | H | H | 0 | H |
| 3 | H | H | H | 1 | H |
| 3 | H | H | H | 2 | H |
| 3 | H | H | H | 3 | H |
| 3 | H | H | H | 4 | H |
| 3 | H | H | H | 5 | H |
| 3 | H | H | H | 6 | H |
| 3 | H | H | H | 0 | 5-Cl |
| 3 | H | H | H | 1 | 5-Cl |
| 3 | H | H | H | 2 | 5-Cl |
| 3 | H | H | H | 3 | 5-Cl |
| 3 | H | H | H | 4 | 5-Cl |
| 3 | H | H | H | 5 | 5-Cl |
| 3 | H | H | H | 6 | 5-Cl |
| 3 | H | H | H | 0 | 5-Br |
| 3 | H | H | H | 1 | 5-Br |
| 3 | H | H | H | 2 | 5-Br |
| 3 | H | H | H | 3 | 5-Br |
| 3 | H | H | H | 4 | 5-Br |
| 3 | H | H | H | 5 | 5-Br |
| 3 | H | H | H | 6 | 5-Br |
| 5 | H | H | H | 0 | H |
| 5 | H | H | H | 1 | H |

TABLE 7-continued

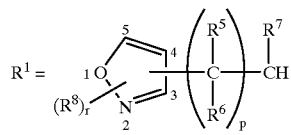

| Bonding position of heterocyclic ring | R⁵ | R⁶ | R⁷ | p | (R⁸)ᵣ |
|---|---|---|---|---|---|
| 5 | H | H | H | 2 | H |
| 5 | H | H | H | 3 | H |
| 5 | H | H | H | 4 | H |
| 5 | H | H | H | 5 | H |
| 5 | H | H | H | 6 | H |
| 5 | H | H | H | 0 | 3-Cl |
| 5 | H | H | H | 1 | 3-Cl |
| 5 | H | H | H | 2 | 3-Cl |
| 5 | H | H | H | 3 | 3-Cl |
| 5 | H | H | H | 4 | 3-Cl |
| 5 | H | H | H | 5 | 3-Cl |
| 5 | H | H | H | 6 | 3-Cl |
| 5 | H | H | H | 0 | 3-Br |
| 5 | H | H | H | 1 | 3-Br |
| 5 | H | H | H | 2 | 3-Br |
| 5 | H | H | H | 3 | 3-Br |
| 5 | H | H | H | 4 | 3-Br |
| 5 | H | H | H | 5 | 3-Br |
| 5 | H | H | H | 6 | 3-Br |
| 4 | H | H | H | 0 | H |
| 4 | H | H | H | 1 | H |
| 4 | H | H | H | 2 | H |
| 4 | H | H | H | 3 | H |
| 4 | H | H | H | 4 | H |
| 4 | H | H | H | 5 | H |
| 4 | H | H | H | 6 | H |
| 4 | H | H | H | 0 | 3,5-(CH₃)₂ |

TABLE 8

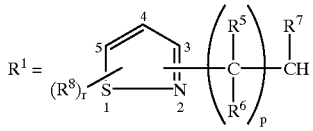

| Bonding position of heterocyclic ring | R⁵ | R⁶ | R⁷ | p | (R⁸)ᵣ |
|---|---|---|---|---|---|
| 3 | H | H | H | 0 | H |
| 3 | H | H | H | 1 | H |
| 3 | H | H | H | 2 | H |
| 3 | H | H | H | 3 | H |
| 3 | H | H | H | 4 | H |
| 3 | H | H | H | 5 | H |
| 3 | H | H | H | 6 | H |
| 3 | H | H | H | 0 | 5-Cl |
| 3 | H | H | H | 1 | 5-Cl |
| 3 | H | H | H | 2 | 5-Cl |
| 3 | H | H | H | 3 | 5-Cl |
| 3 | H | H | H | 4 | 5-Cl |
| 3 | H | H | H | 5 | 5-Cl |
| 3 | H | H | H | 6 | 5-Cl |
| 3 | H | H | H | 0 | 5-Br |
| 3 | H | H | H | 1 | 5-Br |
| 3 | H | H | H | 2 | 5-Br |
| 3 | H | H | H | 3 | 5-Br |
| 3 | H | H | H | 4 | 5-Br |
| 3 | H | H | H | 5 | 5-Br |

TABLE 8-continued $$R^1 = \underset{(R^8)_r}{\overset{5}{\underset{S}{\bigcirc}}}\overset{4}{\underset{1}{\overset{}{\underset{N}{\bigcirc}}}}\overset{3}{\underset{2}{\left(\underset{R^6}{\overset{R^5}{C}}\right)_p}}\overset{R^7}{\underset{}{CH}}$$

| Bonding position of heterocyclic ring | R⁵ | R⁶ | R⁷ | p | (R⁸)ᵣ |
|---|---|---|---|---|---|
| 3 | H | H | H | 6 | 5-Br |

TABLE 9

$$R^1 = \underset{(R^8)_r}{\overset{4}{\underset{S}{\bigcirc}}}\overset{N^3}{\underset{1}{\overset{}{\underset{2}{\bigcirc}}}}\left(\underset{R^6}{\overset{R^5}{C}}\right)_p \overset{R^7}{\underset{}{CH}}$$

| Bonding position of heterocyclic ring | R⁵ | R⁶ | R⁷ | p | (R⁸)ᵣ |
|---|---|---|---|---|---|
| 4 | H | H | H | 0 | H |
| 4 | H | H | H | 1 | H |
| 4 | H | H | H | 2 | H |
| 4 | H | H | H | 3 | H |
| 4 | H | H | H | 4 | H |
| 4 | H | H | H | 5 | H |
| 4 | H | H | H | 6 | H |
| 4 | H | H | H | 0 | 2-Cl |
| 4 | H | H | H | 1 | 2-Cl |
| 4 | H | H | H | 2 | 2-Cl |
| 4 | H | H | H | 3 | 2-Cl |
| 4 | H | H | H | 4 | 2-Cl |
| 4 | H | H | H | 5 | 2-Cl |
| 4 | H | H | H | 6 | 2-Cl |
| 4 | H | H | H | 0 | 2-Br |
| 4 | H | H | H | 1 | 2-Br |
| 4 | H | H | H | 2 | 2-Br |
| 4 | H | H | H | 3 | 2-Br |
| 4 | H | H | H | 4 | 2-Br |
| 4 | H | H | H | 5 | 2-Br |
| 4 | H | H | H | 6 | 2-Br |
| 5 | H | H | H | 0 | H |
| 5 | H | H | H | 1 | H |
| 5 | H | H | H | 2 | H |
| 5 | H | H | H | 3 | H |
| 5 | H | H | H | 4 | H |
| 5 | H | H | H | 5 | H |
| 5 | H | H | H | 6 | H |
| 5 | H | H | H | 0 | 2-Cl |
| 5 | H | H | H | 1 | 2-Cl |
| 5 | H | H | H | 2 | 2-Cl |
| 5 | H | H | H | 3 | 2-Cl |
| 5 | H | H | H | 4 | 2-Cl |
| 5 | H | H | H | 5 | 2-Cl |
| 5 | H | H | H | 6 | 2-Cl |
| 5 | H | H | H | 0 | 2-Br |
| 5 | H | H | H | 1 | 2-Br |
| 5 | H | H | H | 2 | 2-Br |
| 5 | H | H | H | 3 | 2-Br |
| 5 | H | H | H | 4 | 2-Br |
| 5 | H | H | H | 5 | 2-Br |
| 5 | H | H | H | 6 | 2-Br |
| 5 | H | H | H | 1 | 4-CH₃ |
| 5 | H | H | CH₃ | 0 | 4-CH₃ |
| 2 | H | H | CH₃ | 0 | H |

TABLE 10

$$R^1 = \underset{(R^8)_r}{\overset{4}{\underset{N}{\bigcirc}}}\overset{3}{\underset{1}{\overset{}{\underset{2}{\bigcirc}}}}\left(\underset{R^6}{\overset{R^5}{C}}\right)_p \overset{R^7}{\underset{}{CH}}$$

| Bonding position of heterocyclic ring | R⁵ | R⁶ | R⁷ | p | (R⁸)ᵣ |
|---|---|---|---|---|---|
| 1 | H | H | H | 0 | H |
| 1 | H | H | H | 1 | H |
| 1 | H | H | H | 2 | H |
| 1 | H | H | H | 3 | H |
| 1 | H | H | H | 4 | H |
| 1 | H | H | H | 5 | H |
| 1 | H | H | H | 6 | H |
| 1 | H | H | H | 0 | 2-CH₂CH₃ |
| 1 | H | H | H | 1 | 2-CH₂CH₃ |
| 1 | H | H | H | 2 | 2-CH₂CH₃ |
| 1 | H | H | H | 3 | 2-CH₂CH₃ |
| 1 | H | H | H | 4 | 2-CH₂CH₃ |
| 1 | H | H | H | 5 | 2-CH₂CH₃ |
| 1 | H | H | H | 6 | 2-CH₂CH₃ |
| 1 | H | H | H | 0 | 2,5-(CH₃)₂ |
| 1 | H | H | H | 1 | 2,5-(CH₃)₂ |
| 1 | H | H | H | 2 | 2,5-(CH₃)₂ |
| 1 | H | H | H | 3 | 2,5-(CH₃)₂ |
| 1 | H | H | H | 4 | 2,5-(CH₃)₂ |
| 1 | H | H | H | 5 | 2,5-(CH₃)₂ |
| 1 | H | H | H | 6 | 2,5-(CH₃)₂ |
| 1 | H | H | H | 0 | 2,4-(CH₃)₂, 3-CH₂CH₃ |
| 1 | H | H | H | 1 | 2,4-(CH₃)₂, 3-CH₂CH₃ |
| 1 | H | H | H | 2 | 2,4-(CH₃)₂, 3-CH₂CH₃ |
| 1 | H | H | H | 3 | 2,4-(CH₃)₂, 3-CH₂CH₃ |
| 1 | H | H | H | 4 | 2,4-(CH₃)₂, 3-CH₂CH₃ |
| 1 | H | H | H | 5 | 2,4-(CH₃)₂, 3-CH₂CH₃ |
| 1 | H | H | H | 6 | 2,4-(CH₃)₂, 3-CH₂CH₃ |
| 1 | H | H | H | 0 | 2,4-(CH₃)₂, 3-COCH₃ |
| 1 | H | H | H | 1 | 2,4-(CH₃)₂, 3-COCH₃ |
| 1 | H | H | H | 2 | 2,4-(CH₃)₂, 3-COCH₃ |
| 1 | H | H | H | 3 | 2,4-(CH₃)₂, 3-COCH₃ |
| 1 | H | H | H | 4 | 2,4-(CH₃)₂, 3-COCH₃ |
| 1 | H | H | H | 5 | 2,4-(CH₃)₂, 3-COCH₃ |
| 1 | H | H | H | 6 | 2,4-(CH₃)₂, 3-COCH₃ |
| 1 | H | H | H | 0 | 2-COCH₃ |
| 1 | H | H | H | 1 | 2-COCH₃ |
| 1 | H | H | H | 2 | 2-COCH₃ |
| 1 | H | H | H | 3 | 2-COCH₃ |
| 1 | H | H | H | 4 | 2-COCH₃ |
| 1 | H | H | H | 5 | 2-COCH₃ |
| 1 | H | H | H | 6 | 2-COCH₃ |
| 1 | H | H | H | 0 | 2-CHO |
| 1 | H | H | H | 1 | 2-CHO |
| 1 | H | H | H | 2 | 2-CHO |
| 1 | H | H | H | 3 | 2-CHO |
| 1 | H | H | H | 4 | 2-CHO |
| 1 | H | H | H | 5 | 2-CHO |
| 1 | H | H | H | 6 | 2-CHO |
| 2 | H | H | CH₃ | 0 | 2,4-(CH₃)₂ |
| 2 | H | H | CH₃ | 0 | H |
| 2 | H | H | CH₃ | 0 | 1-CH₃ |
| 3 | H | H | CH₃ | 0 | 1-CH₃ |
| 3 | H | H | H | 0 | H |
| 3 | H | H | H | 1 | H |
| 3 | H | H | H | 2 | H |
| 3 | H | H | H | 3 | H |
| 3 | H | H | H | 4 | H |
| 3 | H | H | H | 5 | H |
| 3 | H | H | H | 6 | H |
| 2 | H | H | H | 0 | H |
| 2 | H | H | H | 1 | 1-CH₃ |
| 2 | H | H | H | 2 | 1-CH₃ |
| 2 | H | H | H | 3 | 1-CH₃ |
| 2 | H | H | H | 4 | 1-CH₃ |
| 2 | H | H | H | 5 | 1-CH₃ |
| 2 | H | H | H | 6 | 1-CH₃ |

TABLE 10-continued

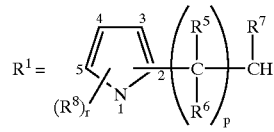

| Bonding position of heterocyclic ring | R⁵ | R⁶ | R⁷ | p | (R⁸)ᵣ |
|---|---|---|---|---|---|
| 2 | H | H | H | 0 | 3,5-(CH₃)₂ |
| 2 | H | H | H | 1 | 3,5-(CH₃)₂ |
| 2 | H | H | H | 2 | 3,5-(CH₃)₂ |
| 2 | H | H | H | 3 | 3,5-(CH₃)₂ |
| 2 | H | H | H | 4 | 3,5-(CH₃)₂ |
| 2 | H | H | H | 5 | 3,5-(CH₃)₂ |
| 2 | H | H | H | 6 | 3,5-(CH₃)₂ |
| 2 | H | H | H | 0 | 3,4,5-(CH₃)₃ |
| 2 | H | H | H | 1 | 3,4,5-(CH₃)₃ |
| 2 | H | H | H | 2 | 3,4,5-(CH₃)₃ |
| 2 | H | H | H | 3 | 3,4,5-(CH₃)₃ |
| 2 | H | H | H | 4 | 3,4,5-(CH₃)₃ |
| 2 | H | H | H | 5 | 3,4,5-(CH₃)₃ |
| 2 | H | H | H | 6 | 3,4,5-(CH₃)₃ |
| 2 | H | H | H | 0 | 3,4-(C₂H₅)₂, 5-CH₃ |
| 2 | H | H | H | 1 | 3,4-(C₂H₅)₂, 5-CH₃ |
| 2 | H | H | H | 2 | 3,4-(C₂H₅)₂, 5-CH₃ |
| 2 | H | H | H | 3 | 3,4-(C₂H₅)₂, 5-CH₃ |
| 2 | H | H | H | 4 | 3,4-(C₂H₅)₂, 5-CH₃ |
| 2 | H | H | H | 5 | 3,4-(C₂H₅)₂, 5-CH₃ |
| 2 | H | H | H | 6 | 3,4-(C₂H₅)₂, 5-CH₃ |

TABLE 11

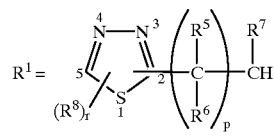

| Bonding position of heterocyclic ring | R⁵ | R⁶ | R⁷ | p | (R⁸)ᵣ |
|---|---|---|---|---|---|
| 2 | H | H | H | 0 | 5-Cl |
| 2 | H | H | H | 1 | 5-Cl |
| 2 | H | H | H | 2 | 5-Cl |
| 2 | H | H | H | 3 | 5-Cl |
| 2 | H | H | H | 4 | 5-Cl |
| 2 | H | H | H | 5 | 5-Cl |
| 2 | H | H | H | 6 | 5-Cl |
| 2 | H | H | H | 0 | 5-Br |
| 2 | H | H | H | 1 | 5-Br |
| 2 | H | H | H | 2 | 5-Br |
| 2 | H | H | H | 3 | 5-Br |
| 2 | H | H | H | 4 | 5-Br |
| 2 | H | H | H | 5 | 5-Br |
| 2 | H | H | H | 6 | 5-Br |
| 2 | H | H | H | 0 | 5-Cl |
| 2 | H | H | H | 1 | 5-Cl |
| 2 | H | H | H | 2 | 5-Cl |
| 2 | H | H | H | 3 | 5-Cl |
| 2 | H | H | H | 4 | 5-Cl |
| 2 | H | H | H | 5 | 5-Cl |
| 2 | H | H | H | 6 | 5-Cl |
| 2 | H | H | H | 0 | 5-Br |
| 2 | H | H | H | 1 | 5-Br |
| 2 | H | H | H | 2 | 5-Br |
| 2 | H | H | H | 3 | 5-Br |
| 2 | H | H | H | 4 | 5-Br |
| 2 | H | H | H | 5 | 5-Br |

TABLE 11-continued

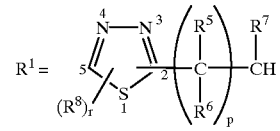

| Bonding position of heterocyclic ring | R⁵ | R⁶ | R⁷ | p | (R⁸)ᵣ |
|---|---|---|---|---|---|
| 2 | H | H | H | 6 | 5-Br |

TABLE 12

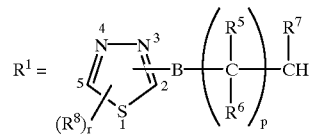

| Bonding position of heterocyclic ring | B | R⁵ | R⁶ | R⁷ | p | (R⁸)ᵣ |
|---|---|---|---|---|---|---|
| 2 | O | H | H | H | 0 | 5-CH₃ |
| 2 | O | H | H | H | 1 | 5-CH₃ |
| 2 | O | H | H | H | 2 | 5-CH₃ |
| 2 | O | H | H | H | 3 | 5-CH₃ |
| 2 | O | H | H | H | 4 | 5-CH₃ |
| 2 | O | H | H | H | 5 | 5-CH₃ |
| 2 | O | H | H | H | 6 | 5-CH₃ |
| 2 | O | H | H | H | 0 | 5-CF₃ |
| 2 | O | H | H | H | 1 | 5-CF₃ |
| 2 | O | H | H | H | 2 | 5-CF₃ |
| 2 | O | H | H | H | 3 | 5-CF₃ |
| 2 | O | H | H | H | 4 | 5-CF₃ |
| 2 | O | H | H | H | 5 | 5-CF₃ |
| 2 | O | H | H | H | 6 | 5-CF₃ |
| 2 | O | H | H | H | 0 | 5-Cl |
| 2 | O | H | H | H | 1 | 5-Cl |
| 2 | O | H | H | H | 2 | 5-Cl |
| 2 | O | H | H | H | 3 | 5-Cl |
| 2 | O | H | H | H | 4 | 5-Cl |
| 2 | O | H | H | H | 5 | 5-Cl |
| 2 | O | H | H | H | 6 | 5-Cl |
| 2 | O | H | H | H | 0 | 5-Br |
| 2 | O | H | H | H | 1 | 5-Br |
| 2 | O | H | H | H | 2 | 5-Br |
| 2 | O | H | H | H | 3 | 5-Br |
| 2 | O | H | H | H | 4 | 5-Br |
| 2 | O | H | H | H | 5 | 5-Br |
| 2 | O | H | H | H | 6 | 5-Br |
| 2 | S | H | H | H | 0 | 5-CH₃ |
| 2 | S | H | H | H | 1 | 5-CH₃ |
| 2 | S | H | H | H | 2 | 5-CH₃ |
| 2 | S | H | H | H | 3 | 5-CH₃ |
| 2 | S | H | H | H | 4 | 5-CH₃ |
| 2 | S | H | H | H | 5 | 5-CH₃ |
| 2 | S | H | H | H | 6 | 5-CH₃ |
| 2 | S | H | H | H | 0 | 5-CF₃ |
| 2 | S | H | H | H | 1 | 5-CF₃ |
| 2 | S | H | H | H | 2 | 5-CF₃ |
| 2 | S | H | H | H | 3 | 5-CF₃ |
| 2 | S | H | H | H | 4 | 5-CF₃ |
| 2 | S | H | H | H | 5 | 5-CF₃ |
| 2 | S | H | H | H | 6 | 5-CF₃ |
| 2 | S | H | H | H | 0 | 5-Cl |
| 2 | S | H | H | H | 1 | 5-Cl |
| 2 | S | H | H | H | 2 | 5-Cl |
| 2 | S | H | H | H | 3 | 5-Cl |
| 2 | S | H | H | H | 4 | 5-Cl |
| 3 | S | H | H | H | 5 | 5-Cl |
| 3 | S | H | H | H | 6 | 5-Cl |

TABLE 12-continued

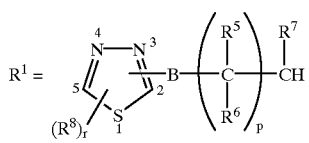

| Bonding position of heterocyclic ring | B | R⁵ | R⁶ | R⁷ | p | (R⁸)ᵣ |
|---|---|---|---|---|---|---|
| 3 | S | H | H | H | 0 | 5-Br |
| 3 | S | H | H | H | 1 | 5-Br |
| 3 | S | H | H | H | 2 | 5-Br |
| 3 | S | H | H | H | 3 | 5-Br |
| 3 | S | H | H | H | 4 | 5-Br |
| 2 | S | H | H | H | 5 | 5-Br |
| 2 | S | H | H | H | 6 | 5-Br |

TABLE 13

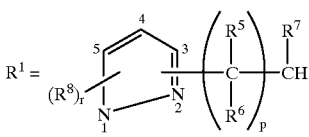

| Bonding position of heterocyclic ring | R⁵ | R⁶ | R⁷ | p | (R⁸)ᵣ |
|---|---|---|---|---|---|
| 1 | H | H | H | 0 | H |
| 1 | H | H | H | 1 | H |
| 1 | H | H | H | 2 | H |
| 1 | H | H | H | 3 | H |
| 1 | H | H | H | 4 | H |
| 1 | H | H | H | 5 | H |
| 1 | H | H | H | 6 | H |
| 1 | H | H | H | 0 | 3-CH₃ |
| 1 | H | H | H | 1 | 3-CH₃ |
| 1 | H | H | H | 2 | 3-CH₃ |
| 1 | H | H | H | 3 | 3-CH₃ |
| 1 | H | H | H | 4 | 3-CH₃ |
| 1 | H | H | H | 5 | 3-CH₃ |
| 1 | H | H | H | 6 | 3-CH₃ |
| 1 | H | H | H | 0 | 4-CH₃ |
| 1 | H | H | H | 1 | 4-CH₃ |
| 1 | H | H | H | 2 | 4-CH₃ |
| 1 | H | H | H | 3 | 4-CH₃ |
| 1 | H | H | H | 4 | 4-CH₃ |
| 1 | H | H | H | 5 | 4-CH₃ |
| 1 | H | H | H | 6 | 4-CH₃ |
| 1 | H | H | H | 0 | 4-Br |
| 1 | H | H | H | 1 | 4-Br |
| 1 | H | H | H | 2 | 4-Br |
| 1 | H | H | H | 3 | 4-Br |
| 1 | H | H | H | 4 | 4-Br |
| 1 | H | H | H | 5 | 4-Br |
| 1 | H | H | H | 6 | 4-Br |
| 1 | H | H | H | 0 | 4-I |
| 1 | H | H | H | 1 | 4-I |
| 1 | H | H | H | 2 | 4-I |
| 1 | H | H | H | 3 | 4-I |
| 1 | H | H | H | 4 | 4-I |
| 1 | H | H | H | 5 | 4-I |
| 1 | H | H | H | 6 | 4-I |
| 1 | H | H | H | 0 | 3,5-(CH₃)₂ |
| 1 | H | H | H | 1 | 3,5-(CH₃)₂ |
| 1 | H | H | H | 2 | 3,5-(CH₃)₂ |
| 1 | H | H | H | 3 | 3,5-(CH₃)₂ |
| 1 | H | H | H | 4 | 3,5-(CH₃)₂ |
| 1 | H | H | H | 5 | 3,5-(CH₃)₂ |
| 1 | H | H | H | 6 | 3,5-(CH₃)₂ |
| 1 | H | H | H | 0 | 3-CH₃, 4-Br |
| 1 | H | H | H | 1 | 3-CH₃, 4-Br |
| 1 | H | H | H | 2 | 3-CH₃, 4-Br |

TABLE 13-continued

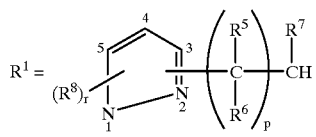

| Bonding position of heterocyclic ring | R⁵ | R⁶ | R⁷ | p | (R⁸)ᵣ |
|---|---|---|---|---|---|
| 1 | H | H | H | 3 | 3-CH₃, 4-Br |
| 1 | H | H | H | 4 | 3-CH₃, 4-Br |
| 1 | H | H | H | 5 | 3-CH₃, 4-Br |
| 1 | H | H | H | 6 | 3-CH₃, 4-Br |
| 1 | H | H | H | 0 | 3,5-(CH₃)₂, 4-Br |
| 1 | H | H | H | 1 | 3,5-(CH₃)₂, 4-Br |
| 1 | H | H | H | 2 | 3,5-(CH₃)₂, 4-Br |
| 1 | H | H | H | 3 | 3,5-(CH₃)₂, 4-Br |
| 1 | H | H | H | 4 | 3,5-(CH₃)₂, 4-Br |
| 1 | H | H | H | 5 | 3,5-(CH₃)₂, 4-Br |
| 1 | H | H | H | 6 | 3,5-(CH₃)₂, 4-Br |
| 4 | H | H | H | 0 | H |

TABLE 14

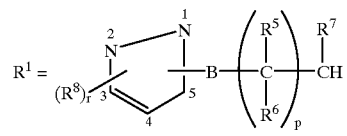

| Bonding position of heterocyclic ring | B | R⁵ | R⁶ | R⁷ | p | (R⁸)ᵣ |
|---|---|---|---|---|---|---|
| 4 | NH | H | H | H | 0 | 5-CH₃, 1-CH₃, 2-C₆H₅ |
| 5 | NH | H | H | H | 0 | 1-CH₂CH₃ |
| 5 | NH | H | H | H | 1 | 1-CH₂CH₃ |
| 5 | NH | H | H | H | 2 | 1-CH₂CH₃ |
| 5 | NH | H | H | H | 3 | 1-CH₂CH₃ |
| 5 | NH | H | H | H | 4 | 1-CH₂CH₃ |
| 5 | NH | H | H | H | 5 | 1-CH₂CH₃ |
| 5 | NH | H | H | H | 6 | 1-CH₂CH₃ |

TABLE 15

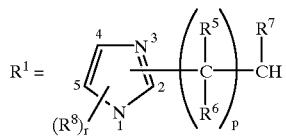

| Bonding position of heterocyclic ring | R⁵ | R⁶ | R⁷ | p | (R⁸)ᵣ |
|---|---|---|---|---|---|
| 1 | H | H | H | 0 | H |
| 1 | H | H | H | 1 | H |
| 1 | H | H | H | 2 | H |
| 1 | H | H | H | 3 | H |
| 1 | H | H | H | 4 | H |
| 1 | H | H | H | 5 | H |
| 1 | H | H | H | 6 | H |
| 1 | H | H | H | 0 | 2-CH₃ |
| 1 | H | H | H | 1 | 2-CH₃ |
| 1 | H | H | H | 2 | 2-CH₃ |
| 1 | H | H | H | 3 | 2-CH₃ |
| 1 | H | H | H | 4 | 2-CH₃ |
| 1 | H | H | H | 5 | 2-CH₃ |
| 1 | H | H | H | 6 | 2-CH₃ |
| 1 | H | H | H | 1 | 2-CH₂CH₃ |
| 1 | H | H | H | 0 | 2-CH₂CH₃ |
| 1 | H | H | H | 2 | 2-CH₂CH₃ |

TABLE 15-continued

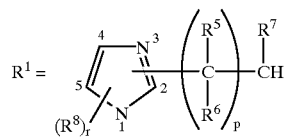

| Bonding position of heterocyclic ring | R⁵ | R⁶ | R⁷ | p | (R⁸)ᵣ |
|---|---|---|---|---|---|
| 1 | H | H | H | 3 | 2-CH₂CH₃ |
| 1 | H | H | H | 4 | 2-CH₂CH₃ |
| 1 | H | H | H | 5 | 2-CH₂CH₃ |
| 1 | H | H | H | 6 | 2-CH₂CH₃ |
| 1 | H | H | H | 0 | 2-CH₂CH₂CH₃ |
| 1 | H | H | H | 1 | 2-CH₂CH₂CH₃ |
| 1 | H | H | H | 2 | 2-CH₂CH₂CH₃ |
| 1 | H | H | H | 3 | 2-CH₂CH₂CH₃ |
| 1 | H | H | H | 4 | 2-CH₂CH₂CH₃ |
| 1 | H | H | H | 5 | 2-CH₂CH₂CH₃ |
| 1 | H | H | H | 6 | 2-CH₂CH₂CH₃ |
| 1 | H | H | H | 0 | 2-CH(CH₃)₂ |
| 1 | H | H | H | 1 | 2-CH(CH₃)₂ |
| 1 | H | H | H | 2 | 2-CH(CH₃)₂ |
| 1 | H | H | H | 3 | 2-CH(CH₃)₂ |
| 1 | H | H | H | 4 | 2-CH(CH₃)₂ |
| 1 | H | H | H | 5 | 2-CH(CH₃)₂ |
| 1 | H | H | H | 6 | 2-CH(CH₃)₂ |
| 1 | H | H | H | 0 | 2-CH(CH₃)₂ |
| 1 | H | H | H | 1 | 4,5-Cl₂ |
| 1 | H | H | H | 2 | 4,5-Cl₂ |
| 1 | H | H | H | 3 | 4,5-Cl₂ |
| 1 | H | H | H | 4 | 4,5-Cl₂ |
| 1 | H | H | H | 5 | 4,5-Cl₃ |
| 1 | H | H | H | 6 | 4,5-Cl₂ |
| 1 | H | H | H | 0 | 2,4,5-Cl₃ |
| 1 | H | H | H | 1 | 2,4,5-Cl₃ |
| 1 | H | H | H | 2 | 2,4,5-Cl₃ |
| 1 | H | H | H | 3 | 2,4,5-Cl₃ |
| 1 | H | H | H | 4 | 2,4,5-Cl₃ |
| 1 | H | H | H | 5 | 2,4,5-Cl₃ |
| 1 | H | H | H | 6 | 2,4,5-Cl₃ |
| 1 | H | H | H | 0 | 4,5-Br₂ |
| 1 | H | H | H | 1 | 4,5-Br₂ |
| 1 | H | H | H | 2 | 4,5-Br₂ |
| 1 | H | H | H | 3 | 4,5-Br₂ |
| 1 | H | H | H | 4 | 4,5-Br₂ |
| 1 | H | H | H | 5 | 4,5-Br₂ |
| 1 | H | H | H | 6 | 4,5-Br₂ |
| 1 | H | H | H | 0 | 2,4,5-Br₃ |
| 1 | H | H | H | 1 | 2,4,5-Br₃ |
| 1 | H | H | H | 2 | 2,4,5-Br₃ |
| 1 | H | H | H | 3 | 2,4,5-Br₃ |
| 1 | H | H | H | 4 | 2,4,5-Br₃ |
| 1 | H | H | H | 5 | 2,4,5-Br₃ |
| 1 | H | H | H | 6 | 2,4,5-Br₃ |
| 1 | H | H | H | 0 | 4,5-(CN)₂ |
| 1 | H | H | H | 1 | 4,5-(CN)₂ |
| 1 | H | H | H | 2 | 4,5-(CN)₂ |
| 1 | H | H | H | 3 | 4,5-(CN)₂ |
| 1 | H | H | H | 4 | 4,5-(CN)₂ |
| 1 | H | H | H | 5 | 4,5-(CN)₂ |
| 1 | H | H | H | 6 | 4,5-(CN)₂ |
| 1 | H | H | CH₃ | 0 | H |
| 1 | H | H | H | 0 | 2-NO₂ |
| 1 | H | H | H | 1 | 2-NO₂ |
| 1 | H | H | H | 2 | 2-NO₂ |
| 1 | H | H | H | 3 | 2-NO₂ |
| 1 | H | H | H | 4 | 2-NO₂ |
| 1 | H | H | H | 5 | 2-NO₂ |
| 1 | H | H | H | 6 | 2-NO₂ |
| 4 | H | H | H | 0 | H |
| 4 | H | H | H | 1 | H |
| 4 | H | H | H | 2 | H |
| 5 | H | H | H | 0 | 4-CH₃ |
| 2 | H | H | H | 0 | H |

TABLE 16

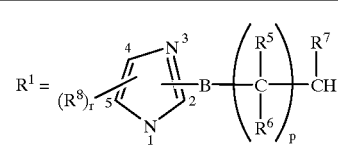

| Bonding position of heterocyclic ring | B | R⁵ | R⁶ | R⁷ | p | (R⁸)ᵣ |
|---|---|---|---|---|---|---|
| 2 | S | H | H | H | 0 | H |
| 2 | S | H | H | H | 1 | H |
| 2 | S | H | H | H | 2 | H |
| 2 | S | H | H | H | 3 | H |
| 2 | S | H | H | H | 4 | H |
| 2 | S | H | H | H | 5 | H |
| 2 | S | H | H | H | 6 | H |
| 2 | S | H | H | H | 0 | 1-CH₃ |
| 2 | S | H | H | H | 1 | 1-CH₃ |
| 2 | S | H | H | H | 2 | 1-CH₃ |
| 2 | S | H | H | H | 3 | 1-CH₃ |
| 2 | S | H | H | H | 4 | 1-CH₃ |
| 2 | S | H | H | H | 5 | 1-CH₃ |
| 2 | S | H | H | H | 6 | 1-CH₃ |

TABLE 17

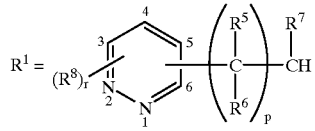

| Bonding position of heterocyclic ring | R⁵ | R⁶ | R⁷ | p | (R⁸)ᵣ |
|---|---|---|---|---|---|
| 4 | H | H | H | 0 | 3,6-Cl₂ |
| 4 | H | H | H | 1 | 3,6-Cl₂ |
| 4 | H | H | H | 2 | 3,6-Cl₂ |
| 4 | H | H | H | 3 | 3,6-Cl₂ |
| 4 | H | H | H | 4 | 3,6-Cl₂ |
| 4 | H | H | H | 5 | 3,6-Cl₂ |
| 4 | H | H | H | 6 | 3,6-Cl₂ |

TABLE 18

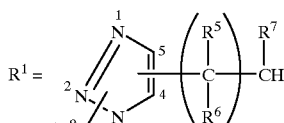

| Bonding position of heterocyclic ring | R⁵ | R⁶ | R⁷ | p | (R⁸)ᵣ |
|---|---|---|---|---|---|
| 3 | H | H | H | 0 | H |
| 3 | H | H | H | 1 | H |
| 3 | H | H | H | 2 | H |
| 3 | H | H | H | 3 | H |
| 3 | H | H | H | 4 | H |
| 3 | H | H | H | 5 | H |
| 3 | H | H | H | 6 | H |

TABLE 19

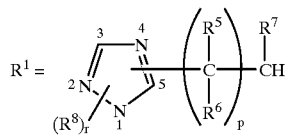

| Bonding position of heterocyclic ring | R5 | R6 | R7 | p | (R8)r |
|---|---|---|---|---|---|
| 1 | H | H | H | 0 | H |
| 1 | H | H | H | 1 | H |
| 1 | H | H | H | 2 | H |
| 1 | H | H | H | 3 | H |
| 1 | H | H | H | 4 | H |
| 1 | H | H | H | 5 | H |
| 1 | H | H | H | 6 | H |
| 4 | H | H | H | 0 | H |
| 4 | H | H | H | 1 | H |
| 4 | H | H | H | 2 | H |
| 4 | H | H | H | 3 | H |
| 4 | H | H | H | 4 | H |
| 4 | H | H | H | 5 | H |
| 4 | H | H | H | 6 | H |

TABLE 20

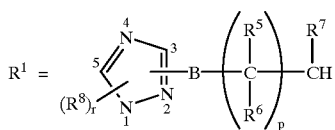

| Bonding position of heterocyclic ring | B | R5 | R6 | R7 | p | (R8)r |
|---|---|---|---|---|---|---|
| 3 | S | H | H | H | 0 | H |
| 3 | S | H | H | H | 1 | H |
| 3 | S | H | H | H | 2 | H |
| 3 | S | H | H | H | 3 | H |
| 3 | S | H | H | H | 4 | H |
| 3 | S | H | H | H | 5 | H |
| 3 | S | H | H | H | 6 | H |
| 5 | S | H | H | H | 0 | 1-CH3 |
| 5 | S | H | H | H | 1 | 1-CH3 |
| 5 | S | H | H | H | 2 | 1-CH3 |
| 5 | S | H | H | H | 3 | 1-CH3 |
| 5 | S | H | H | H | 4 | 1-CH3 |
| 5 | S | H | H | H | 5 | 1-CH3 |
| 5 | S | H | H | H | 6 | 1-CH3 |

TABLE 21

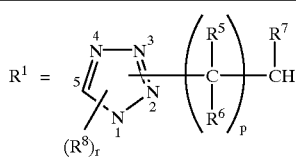

| Bonding position of heterocyclic ring | R5 | R6 | R7 | p | (R8)r |
|---|---|---|---|---|---|
| 1 | H | H | H | 0 | H |
| 1 | H | H | H | 1 | H |
| 1 | H | H | H | 2 | H |
| 1 | H | H | H | 3 | H |
| 1 | H | H | H | 4 | H |
| 1 | H | H | H | 5 | H |
| 1 | H | H | H | 6 | H |

TABLE 22

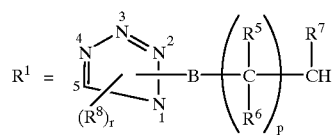

| Bonding position of heterocyclic ring | B | R5 | R6 | R7 | p | (R8)r |
|---|---|---|---|---|---|---|
| 5 | S | H | H | H | 0 | 1-CH3 |
| 5 | S | H | H | H | 1 | 1-CH3 |
| 5 | S | H | H | H | 2 | 1-CH3 |
| 5 | S | H | H | H | 3 | 1-CH3 |
| 5 | S | H | H | H | 4 | 1-CH3 |
| 5 | S | H | H | H | 5 | 1-CH3 |
| 5 | S | H | H | H | 6 | 1-CH3 |

TABLE 23

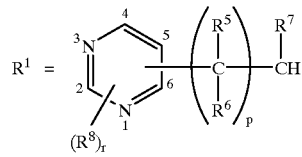

| Bonding position of heterocyclic ring | R5 | R6 | R7 | p | (R8)r |
|---|---|---|---|---|---|
| 4 | H | H | H | 0 | H |
| 4 | H | H | H | 1 | H |
| 4 | H | H | H | 2 | H |
| 4 | H | H | H | 3 | H |
| 4 | H | H | H | 4 | H |
| 4 | H | H | H | 5 | H |
| 4 | H | H | H | 6 | H |
| 4 | H | H | H | 0 | 6-CH3 |
| 4 | H | H | H | 1 | 6-CH3 |
| 4 | H | H | H | 2 | 6-CH3 |
| 4 | H | H | H | 3 | 6-CH3 |
| 4 | H | H | H | 4 | 6-CH3 |
| 4 | H | H | H | 5 | 6-CH3 |
| 4 | H | H | H | 6 | 6-CH3 |
| 4 | H | H | H | 0 | 2,6-Cl2 |

TABLE 24

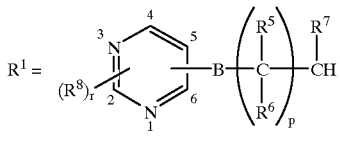

| Bonding position of heterocyclic ring | B | R5 | R6 | R7 | p | (R8)r |
|---|---|---|---|---|---|---|
| 2 | O | H | H | H | 6 | 4-CH3 |
| 4 | O | H | H | H | 0 | 2,6-(CH3)2 |
| 4 | O | H | H | H | 1 | 2,6-(CH3)2 |
| 4 | O | H | H | H | 2 | 2,6-(CH3)2 |
| 4 | O | H | H | H | 3 | 2,6-(CH3)2 |
| 4 | O | H | H | H | 4 | 2,6-(CH3)2 |
| 4 | O | H | H | H | 5 | 2,6-(CH3)2 |
| 4 | O | H | H | H | 6 | 2,6-(CH3)2 |
| 2 | S | H | H | H | 0 | H |
| 2 | S | H | H | H | 1 | H |
| 2 | S | H | H | H | 2 | H |
| 2 | S | H | H | H | 3 | H |
| 2 | S | H | H | H | 4 | H |

TABLE 24-continued

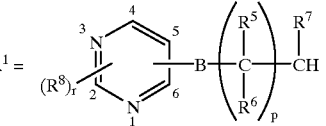

$R^1 =$

| Bonding position of heterocyclic ring | B | $R^5$ | $R^6$ | $R^7$ | p | $(R^8)_r$ |
|---|---|---|---|---|---|---|
| 2 | S | H | H | H | 5 | H |
| 2 | S | H | H | H | 6 | H |
| 2 | NH | H | H | H | 1 | H |
| 2 | NH | H | H | H | 0 | H |
| 2 | O | H | H | H | 2 | 5-$CF_3$ |
| 2 | O | H | H | H | 3 | 5-$CF_3$ |
| 5 | O | H | H | H | 2 | 5-$CF_3$ |
| 5 | O | H | H | H | 3 | 5-$CF_3$ |
| 2 | NH | H | H | H | 2 | H |
| 2 | NH | H | H | H | 3 | H |
| 2 | NH | H | H | H | 4 | H |
| 3 | NH | H | H | H | 5 | H |
| 3 | NH | H | H | H | 6 | H |
| 3 | S | H | H | H | 0 | 4-$CH_3$ |
| 3 | S | H | H | H | 1 | 4-$CH_3$ |
| 3 | S | H | H | H | 2 | 4-$CH_3$ |
| 3 | S | H | H | H | 3 | 4-$CH_3$ |
| 3 | S | H | H | H | 4 | 4-$CH_3$ |
| 2 | O | H | H | H | 0 | H |
| 2 | O | H | H | H | 1 | H |
| 2 | O | H | H | H | 2 | H |
| 2 | O | H | H | H | 3 | H |
| 2 | O | H | H | H | 4 | H |
| 2 | O | H | H | H | 5 | H |
| 2 | O | H | H | H | 6 | H |
| 2 | O | H | H | H | 0 | 4,6-$(CH_3)_2$ |
| 2 | O | H | H | H | 1 | 4,6-$(CH_3)_2$ |
| 2 | O | H | H | H | 2 | 4,6-$(CH_3)_2$ |
| 2 | O | H | H | H | 3 | 4,6-$(CH_3)_2$ |
| 2 | O | H | H | H | 4 | 4,6-$(CH_3)_2$ |
| 2 | O | H | H | H | 5 | 4,6-$(CH_3)_2$ |
| 2 | O | H | H | H | 6 | 4,6-$(CH_3)_2$ |
| 2 | NH | H | H | H | 0 | 4,6-$(CH_3)_2$ |
| 2 | NH | H | H | H | 1 | 4,6-$(CH_3)_2$ |
| 2 | NH | H | H | H | 2 | 4,6-$(CH_3)_2$ |
| 2 | NH | H | H | H | 3 | 4,6-$(CH_3)_2$ |
| 2 | NH | H | H | H | 4 | 4,6-$(CH_3)_2$ |
| 2 | NH | H | H | H | 5 | 4,6-$(CH_3)_2$ |
| 2 | NH | H | H | H | 6 | 4,6-$(CH_3)_2$ |
| 2 | O | H | H | H | 0 | 4-$CH_3$ |
| 2 | O | H | H | H | 1 | 4-$CH_3$ |
| 2 | O | H | H | H | 2 | 4-$CH_3$ |
| 2 | O | H | H | H | 3 | 4-$CH_3$ |
| 2 | O | H | H | H | 4 | 4-$CH_3$ |
| 2 | O | H | H | H | 5 | 4-$CH_3$ |
| 2 | S | H | H | H | 5 | 4-$CH_3$ |
| 2 | S | H | H | H | 6 | 4-$CH_3$ |
| 2 | NH | H | H | H | 0 | 4-$CH_3$ |
| 2 | NH | H | H | H | 1 | 4-$CH_3$ |
| 2 | NH | H | H | H | 2 | 4-$CH_3$ |
| 2 | NH | H | H | H | 3 | 4-$CH_3$ |
| 2 | NH | H | H | H | 4 | 4-$CH_3$ |
| 2 | NH | H | H | H | 5 | 4-$CH_3$ |
| 2 | NH | H | H | H | 6 | 4-$CH_3$ |
| 2 | S | H | H | H | 0 | 4,6-$(CH_3)_2$ |
| 2 | S | H | H | H | 1 | 4,6-$(CH_3)_2$ |
| 2 | S | H | H | H | 2 | 4,6-$(CH_3)_2$ |
| 2 | S | H | H | H | 3 | 4,6-$(CH_3)_2$ |
| 2 | S | H | H | H | 4 | 4,6-$(CH_3)_2$ |
| 2 | S | H | H | H | 5 | 4,6-$(CH_3)_2$ |
| 2 | S | H | H | H | 0 | 4,6-$Cl_2$ |
| 2 | S | H | H | H | 6 | 4,6-$(CH_3)_2$ |
| 2 | S | H | H | H | 1 | 4,6-$Cl_2$ |
| 2 | S | H | H | H | 2 | 4,6-$Cl_2$ |
| 2 | S | H | H | H | 3 | 4,6-$Cl_2$ |
| 2 | S | H | H | H | 4 | 4,6-$Cl_2$ |
| 2 | S | H | H | H | 5 | 4,6-$Cl_2$ |
| 2 | S | H | H | H | 6 | 4,6-$Cl_2$ |
| 4 | NH | H | H | H | 0 | H |
| 4 | NH | H | H | H | 1 | H |
| 4 | NH | H | H | H | 2 | H |
| 4 | NH | H | H | H | 3 | H |
| 4 | NH | H | H | H | 4 | H |
| 4 | NH | H | H | H | 5 | H |
| 4 | NH | H | H | H | 6 | H |
| 2 | NH | H | H | H | 0 | 5-Br |
| 2 | NH | H | H | H | 1 | 5-Br |
| 2 | NH | H | H | H | 2 | 5-Br |
| 2 | NH | H | H | H | 3 | 5-Br |
| 2 | NH | H | H | H | 4 | 5-Br |
| 2 | NH | H | H | H | 5 | 5-Br |
| 2 | NH | H | H | H | 6 | 5-Br |
| 4 | NH | H | H | H | 0 | 2,6-$(CH_3)_2$ |
| 4 | NH | H | H | H | 1 | 2,6-$(CH_3)_2$ |
| 4 | NH | H | H | H | 2 | 2,6-$(CH_3)_2$ |
| 4 | NH | H | H | H | 3 | 2,6-$(CH_3)_2$ |
| 4 | NH | H | H | H | 4 | 2,6-$(CH_3)_2$ |
| 4 | NH | H | H | H | 5 | 2,6-$(CH_3)_2$ |
| 4 | NH | H | H | H | 6 | 2,6-$(CH_3)_2$ |
| 2 | NH | H | H | H | 0 | 4-Cl, 6-$CH_3$ |
| 2 | NH | H | H | H | 1 | 4-Cl, 6-$CH_3$ |
| 2 | NH | H | H | H | 2 | 4-Cl, 6-$CH_3$ |
| 2 | NH | H | H | H | 3 | 4-Cl, 6-$CH_3$ |
| 2 | NH | H | H | H | 4 | 4-Cl, 6-$CH_3$ |
| 2 | NH | H | H | H | 5 | 4-Cl, 6-$CH_3$ |
| 2 | NH | H | H | H | 6 | 4-Cl, 6-$CH_3$ |
| 2 | NH | H | H | H | 0 | 4-$OCH_3$, 6-$CH_3$ |
| 2 | NH | H | H | H | 1 | 4-$OCH_3$, 6-$CH_3$ |
| 2 | NH | H | H | H | 2 | 4-$OCH_3$, 6-$CH_3$ |
| 2 | NH | H | H | H | 3 | 4-$OCH_3$, 6-$CH_3$ |
| 2 | NH | H | H | H | 4 | 4-$OCH_3$, 6-$CH_3$ |
| 2 | NH | H | H | H | 5 | 4-$OCH_3$, 6-$CH_3$ |
| 2 | NH | H | H | H | 6 | 4-$OCH_3$, 6-$CH_3$ |
| 2 | O | H | H | H | 0 | 4,6-$(OCH_3)_2$ |
| 2 | O | H | H | H | 1 | 4,6-$(OCH_3)_2$ |
| 2 | O | H | H | H | 2 | 4,6-$(OCH_3)_2$ |
| 2 | O | H | H | H | 3 | 4,6-$(OCH_3)_2$ |
| 2 | O | H | H | H | 4 | 4,6-$(OCH_3)_2$ |
| 2 | O | H | H | H | 5 | 4,6-$(OCH_3)_2$ |
| 2 | O | H | H | H | 6 | 4,6-$(OCH_3)_2$ |
| 2 | NH | H | H | H | 0 | 4,6-$(OCH_3)_2$ |
| 2 | NH | H | H | H | 1 | 4,6-$(OCH_3)_2$ |
| 2 | NH | H | H | H | 2 | 4,6-$(OCH_3)_2$ |
| 2 | NH | H | H | H | 4 | 4,6-$(OCH_3)_2$ |
| 2 | NH | H | H | H | 3 | 4,6-$(OCH_3)_2$ |
| 2 | NH | H | H | H | 2 | 5-$CF_3$ |
| 2 | NH | H | H | H | 3 | 5-$CF_3$ |
| 5 | NH | H | H | H | 2 | 5-$CF_3$ |
| 5 | NH | H | H | H | 3 | 5-$CF_3$ |
| 2 | NH | H | H | H | 5 | 4,6-$(OCH_3)_2$ |
| 2 | NH | H | H | H | 6 | 4,6-$(OCH_3)_2$ |
| 2 | S | H | H | H | 0 | 4,6-$(OCH_3)_2$ |
| 2 | S | H | H | H | 1 | 4,6-$(OCH_3)_2$ |
| 2 | S | H | H | H | 2 | 4,6-$(OCH_3)_2$ |
| 2 | S | H | H | H | 3 | 4,6-$(OCH_3)_2$ |
| 2 | S | H | H | H | 4 | 4,6-$(OCH_3)_2$ |
| 2 | S | H | H | H | 5 | 4,6-$(OCH_3)_2$ |
| 2 | S | H | H | H | 6 | 4,6-$(OCH_3)_2$ |
| 5 | NH | H | H | H | 0 | 4,6-$Cl_2$ |
| 5 | NH | H | H | H | 1 | 4,6-$Cl_2$ |
| 2 | S | H | H | H | 2 | 5-$CF_3$ |
| 2 | S | H | H | H | 3 | 5-$CF_3$ |
| 5 | S | H | H | H | 2 | 5-$CF_3$ |
| 5 | S | H | H | H | 3 | 5-$CF_3$ |

TABLE 25

$R^1 =$ 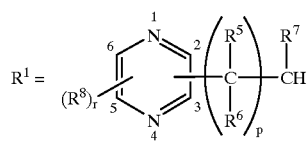

| Bonding position of heterocyclic ring | $R^5$ | $R^6$ | $R^7$ | p | $(R^8)_r$ |
|---|---|---|---|---|---|
| 2 | H | H | H | 0 | H |
| 2 | H | H | H | 1 | H |
| 2 | H | H | H | 2 | H |
| 2 | H | H | H | 3 | H |
| 2 | H | H | H | 4 | H |
| 2 | H | H | H | 5 | H |
| 2 | H | H | H | 6 | 5-CH$_3$ |
| 2 | H | H | H | 0 | 5-CH$_3$ |
| 2 | H | H | H | 1 | 5-CH$_3$ |
| 2 | H | H | H | 2 | 5-CH$_3$ |
| 2 | H | H | H | 3 | 5-CH$_3$ |
| 2 | H | H | H | 4 | 5-CH$_3$ |
| 2 | H | H | H | 5 | 5-CH$_3$ |
| 2 | H | H | H | 6 | 5-CH$_3$ |
| 2 | H | H | H | 0 | 6-CH$_3$ |
| 2 | H | H | H | 1 | 6-CH$_3$ |
| 2 | H | H | H | 2 | 6-CH$_3$ |
| 2 | H | H | H | 3 | 6-CH$_3$ |
| 2 | H | H | H | 4 | 6-CH$_3$ |
| 2 | H | H | H | 5 | 6-CH$_3$ |
| 2 | H | H | H | 6 | 6-CH$_3$ |
| 2 | H | H | H | 0 | 3-CH$_3$ |
| 2 | H | H | H | 1 | 3-CH$_3$ |
| 2 | H | H | H | 2 | 3-CH$_3$ |
| 2 | H | H | H | 3 | 3-CH$_3$ |
| 2 | H | H | H | 4 | 3-CH$_3$ |
| 2 | H | H | H | 5 | 3-CH$_3$ |
| 2 | H | H | H | 6 | 3-CH$_3$ |
| 2 | H | H | H | 0 | 5-CH$_3$ |
| 2 | H | H | H | 1 | 5-CH$_3$ |
| 2 | H | H | H | 2 | 5-CH$_3$ |
| 2 | H | H | H | 3 | 5-CH$_3$ |
| 2 | H | H | H | 4 | 5-CH$_3$ |
| 2 | H | H | H | 5 | 5-CH$_3$ |
| 2 | H | H | H | 6 | 5-CH$_3$ |
| 2 | H | H | H | 0 | 3-OCH$_3$ |
| 2 | H | H | H | 1 | 3-OCH$_3$ |
| 2 | H | H | H | 2 | 3-OCH$_3$ |
| 2 | H | H | H | 3 | 3-OCH$_3$ |
| 2 | H | H | H | 4 | 3-OCH$_3$ |
| 2 | H | H | H | 5 | 3-OCH$_3$ |
| 2 | H | H | H | 6 | 3-OCH$_3$ |
| 2 | H | H | H | 0 | 6-OCH$_2$CH$_2$CH$_3$ |
| 2 | H | H | H | 1 | 6-OCH$_2$CH$_2$CH$_3$ |
| 2 | H | H | H | 2 | 6-OCH$_2$CH$_2$CH$_3$ |
| 2 | H | H | H | 3 | 6-OCH$_2$CH$_2$CH$_3$ |
| 2 | H | H | H | 4 | 6-OCH$_2$CH$_2$CH$_3$ |
| 2 | H | H | H | 5 | 6-OCH$_2$CH$_2$CH$_3$ |
| 2 | H | H | H | 6 | 6-OCH$_2$CH$_2$CH$_3$ |

TABLE 26

$R^1 =$ 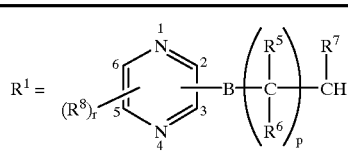

| Bonding position of heterocyclic ring | B | $R^5$ | $R^6$ | $R^7$ | p | $(R^8)_r$ |
|---|---|---|---|---|---|---|
| 2 | O | H | H | H | 0 | H |
| 2 | O | H | H | H | 1 | H |
| 2 | O | H | H | H | 2 | H |

TABLE 26-continued $R^1 =$ 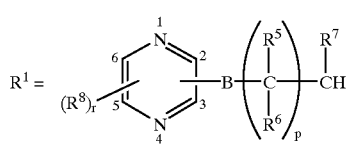

| Bonding position of heterocyclic ring | B | $R^5$ | $R^6$ | $R^7$ | p | $(R^8)_r$ |
|---|---|---|---|---|---|---|
| 2 | O | H | H | H | 3 | H |
| 2 | O | H | H | H | 4 | H |
| 2 | O | H | H | H | 5 | H |
| 2 | O | H | H | H | 6 | H |
| 2 | NH | H | H | H | 0 | H |
| 2 | NH | H | H | H | 1 | H |
| 2 | NH | H | H | H | 2 | H |
| 2 | NH | H | H | H | 3 | H |
| 2 | NH | H | H | H | 4 | H |
| 2 | NH | H | H | H | 5 | H |
| 2 | NH | H | H | H | 6 | H |
| 2 | S | H | H | H | 0 | H |
| 2 | S | H | H | H | 1 | H |
| 2 | S | H | H | H | 2 | H |
| 2 | S | H | H | H | 3 | H |
| 2 | S | H | H | H | 4 | H |
| 2 | S | H | H | H | 5 | H |
| 2 | S | H | H | H | 6 | H |
| 2 | O | H | H | H | 0 | 6-Cl |
| 2 | O | H | H | H | 1 | 6-Cl |
| 2 | O | H | H | H | 2 | 6-Cl |
| 2 | O | H | H | H | 3 | 6-Cl |
| 2 | O | H | H | H | 4 | 6-Cl |
| 2 | O | H | H | H | 5 | 6-Cl |
| 2 | O | H | H | H | 6 | 6-Cl |
| 2 | NH | H | H | H | 0 | 6-Cl |
| 2 | NH | H | H | H | 1 | 6-Cl |
| 2 | NH | H | H | H | 2 | 6-Cl |
| 2 | NH | H | H | H | 3 | 6-Cl |
| 2 | NH | H | H | H | 4 | 6-Cl |
| 2 | NH | H | H | H | 5 | 6-Cl |
| 2 | NH | H | H | H | 6 | 6-Cl |
| 2 | S | H | H | H | 0 | 6-Cl |
| 2 | S | H | H | H | 1 | 6-Cl |
| 2 | S | H | H | H | 2 | 6-Cl |
| 2 | S | H | H | H | 3 | 6-Cl |
| 2 | S | H | H | H | 4 | 6-Cl |
| 2 | S | H | H | H | 5 | 6-Cl |
| 2 | S | H | H | H | 6 | 6-Cl |

TABLE 27

$R^1 =$ 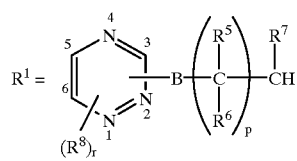

| Bonding position of heterocyclic ring | B | $R^5$ | $R^6$ | $R^7$ | p | $(R^8)_r$ |
|---|---|---|---|---|---|---|
| 3 | NH | H | H | H | 0 | H |
| 3 | NH | H | H | H | 1 | H |
| 3 | NH | H | H | H | 2 | H |
| 3 | NH | H | H | H | 3 | H |
| 3 | NH | H | H | H | 4 | H |
| 3 | NH | H | H | H | 5 | H |
| 3 | NH | H | H | H | 6 | H |

TABLE 28

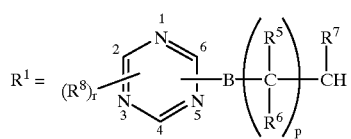

| Bonding position of heterocyclic ring | B | R⁵ | R⁶ | R⁷ | p | (R⁸)ᵣ |
|---|---|---|---|---|---|---|
| 2 | O | H | H | H | 0 | 4,6-Cl₂ |
| 2 | O | H | H | H | 1 | 4,6-Cl₂ |
| 2 | O | H | H | H | 2 | 4,6-Cl₂ |
| 2 | O | H | H | H | 3 | 4,6-Cl₂ |
| 2 | O | H | H | H | 4 | 4,6-Cl₂ |
| 2 | O | H | H | H | 5 | 4,6-Cl₂ |
| 2 | O | H | H | H | 6 | 4,6-Cl₂ |
| 2 | S | H | H | H | 0 | 4,6-Cl₂ |
| 2 | S | H | H | H | 1 | 4,6-Cl₂ |
| 2 | S | H | H | H | 2 | 4,6-Cl₂ |
| 2 | S | H | H | H | 3 | 4,6-Cl₂ |
| 2 | S | H | H | H | 4 | 4,6-Cl₂ |
| 2 | S | H | H | H | 5 | 4,6-Cl₂ |
| 2 | S | H | H | H | 6 | 4,6-Cl₂ |
| 2 | NH | H | H | H | 0 | 4,6-Cl₂ |
| 2 | NH | H | H | H | 2 | 4,6-Cl₂ |
| 2 | NH | H | H | H | 1 | 4,6-Cl₂ |
| 2 | NH | H | H | H | 3 | 4,6-Cl₂ |
| 2 | NH | H | H | H | 4 | 4,6-Cl₂ |
| 2 | NH | H | H | H | 5 | 4,6-Cl₂ |
| 2 | NH | H | H | H | 6 | 4,6-Cl₂ |
| 2 | O | H | H | H | 0 | 4-Cl, 6-OCH₃ |
| 2 | O | H | H | H | 1 | 4-Cl, 6-OCH₃ |
| 2 | O | H | H | H | 2 | 4-Cl, 6-OCH₃ |
| 2 | O | H | H | H | 3 | 4-Cl, 6-OCH₃ |
| 2 | O | H | H | H | 4 | 4-Cl, 6-OCH₃ |
| 2 | O | H | H | H | 5 | 4-Cl, 6-OCH₃ |
| 2 | O | H | H | H | 6 | 4-Cl, 6-OCH₃ |
| 2 | NH | H | H | H | 1 | 4-Cl, 6-OCH₃ |
| 2 | NH | H | H | H | 0 | 4-Cl, 6-OCH₃ |
| 2 | NH | H | H | H | 2 | 4-Cl, 6-OCH₃ |
| 2 | NH | H | H | H | 3 | 4-Cl, 6-OCH₃ |
| 2 | NH | H | H | H | 4 | 4-Cl, 6-OCH₃ |
| 2 | NH | H | H | H | 5 | 4-Cl, 6-OCH₃ |
| 2 | NH | H | H | H | 6 | 4-Cl, 6-OCH₃ |
| 2 | S | H | H | H | 0 | 4-Cl, 6-OCH₃ |
| 2 | S | H | H | H | 1 | 4-Cl, 6-OCH₃ |
| 2 | S | H | H | H | 2 | 4-Cl, 6-OCH₃ |
| 2 | S | H | H | H | 3 | 4-Cl, 6-OCH₃ |
| 2 | S | H | H | H | 4 | 4-Cl, 6-OCH₃ |
| 2 | S | H | H | H | 5 | 4-Cl, 6-OCH₃ |
| 2 | S | H | H | H | 6 | 4-Cl, 6-OCH₃ |

TABLE 29

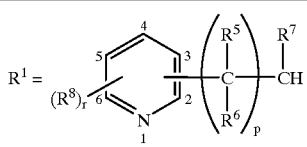

| Bonding position of heterocyclic ring | R⁵ | R⁶ | R⁷ | p | (R⁸)ᵣ |
|---|---|---|---|---|---|
| 3 | H | H | H | 0 | H |
| 3 | H | H | H | 0 | 6-Cl |
| 3 | H | H | H | 0 | 6-Br |
| 3 | H | H | H | 0 | 6-I |
| 3 | H | H | H | 0 | 6-CH₃ |
| 3 | H | H | H | 0 | 6-CF₃ |
| 3 | H | H | CH₃ | 0 | H |
| 3 | H | H | H | 0 | 2-CH₃ |

TABLE 29-continued

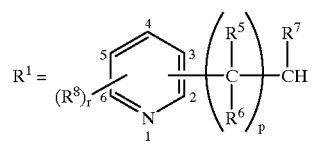

| Bonding position of heterocyclic ring | R⁵ | R⁶ | R⁷ | p | (R⁸)ᵣ |
|---|---|---|---|---|---|
| 3 | H | H | H | 0 | 4-(CH₂)₃CH₃ |
| 3 | H | H | H | 0 | 2-Cl |
| 3 | H | H | H | 0 | 4-Br |
| 3 | H | H | H | 0 | 2,6-Cl₂ |
| 3 | H | H | H | 0 | 2-Cl, 6-CH₃ |
| 3 | H | H | H | 0 | 5,6-Cl₂ |
| 3 | H | H | H | 0 | 2,6-(OCH₃)₂ |
| 3 | H | H | H | 0 | 2-SCH₃ |
| 3 | H | H | H | 0 | 5-CH₃ |
| 3 | H | H | H | 1 | H |
| 3 | H | H | H | 2 | H |
| 3 | H | H | H | 3 | H |
| 3 | H | H | H | 4 | H |
| 3 | H | H | H | 5 | H |
| 3 | H | H | H | 6 | H |
| 3 | H | H | H | 1 | 5-CH₃ |
| 3 | H | H | H | 2 | 5-CH₃ |
| 3 | H | H | H | 3 | 5-CH₃ |
| 3 | H | H | H | 4 | 5-CH₃ |
| 3 | H | H | H | 5 | 5-CH₃ |
| 3 | H | H | H | 6 | 5-CH₃ |
| 3 | H | H | CH₃ | 1 | H |
| 3 | H | H | CH₃ | 2 | H |
| 3 | H | H | CH₃ | 4 | H |
| 3 | H | H | CH₃ | 5 | H |
| 3 | H | H | CH₃ | 3 | H |
| 3 | H | H | CH₃ | 6 | H |
| 3 | H | H | CH₃ | 1 | 2-CH₃ |
| 3 | H | H | CH₃ | 2 | 2-CH₃ |
| 3 | H | H | CH₃ | 3 | 2-CH₃ |
| 3 | H | H | CH₃ | 4 | 2-CH₃ |
| 3 | H | H | CH₃ | 5 | 2-CH₃ |
| 3 | H | H | CH₃ | 6 | 2-CH₃ |
| 3 | H | H | CH₃ | 1 | 6-CH₃ |
| 3 | H | H | CH₃ | 2 | 6-CH₃ |
| 3 | H | H | CH₃ | 3 | 6-CH₃ |
| 3 | H | H | H | 4 | 6-CH₃ |
| 3 | H | H | H | 6 | 6-CH₃ |
| 3 | H | H | H | 5 | 6-CH₃ |
| 3 | H | H | H | 1 | 6-Cl |
| 3 | H | H | H | 2 | 6-Cl |
| 3 | H | H | H | 3 | 6-Cl |
| 3 | H | H | H | 4 | 6-Cl |
| 3 | H | H | H | 5 | 6-Cl |
| 3 | H | H | H | 6 | 6-Cl |
| 3 | H | H | H | 1 | 6-Br |
| 3 | H | H | H | 2 | 6-Br |
| 3 | H | H | H | 3 | 6-Br |
| 3 | H | H | H | 4 | 6-Br |
| 3 | H | H | H | 5 | 6-Br |
| 3 | H | H | H | 6 | 6-Br |
| 3 | H | H | H | 1 | 6-I |
| 3 | H | H | H | 2 | 6-I |
| 3 | H | H | H | 3 | 6-I |
| 3 | H | H | H | 4 | 6-I |
| 3 | H | H | H | 5 | 6-I |
| 3 | H | H | H | 6 | 6-I |
| 3 | H | H | H | 1 | 6-CF₃ |
| 3 | H | H | H | 2 | 6-CF₃ |
| 3 | H | H | H | 3 | 6-CF₃ |
| 3 | H | H | H | 4 | 6-CF₃ |
| 3 | H | H | H | 5 | 6-CF₃ |
| 3 | H | H | H | 6 | 6-CF₃ |
| 3 | H | H | H | 1 | 2-Cl |
| 3 | H | H | H | 2 | 2-Cl |
| 3 | H | H | H | 3 | 2-Cl |

TABLE 29-continued $$R^1 = (R^8)_r \underset{\underset{1}{N}}{\overset{5}{\underset{6}{\bigcirc}}\overset{4}{\underset{3}{\phantom{\bigcirc}}}} - \left(\underset{R^6}{\overset{R^5}{\underset{|}{C}}}\right)_p \underset{R^7}{\overset{R^7}{\text{CH}}}$$

| Bonding position of heterocyclic ring | $R^5$ | $R^6$ | $R^7$ | p | $(R^8)_r$ |
|---|---|---|---|---|---|
| 3 | H | H | H | 4 | 2-Cl |
| 3 | H | H | H | 5 | 2-Cl |
| 3 | H | H | H | 6 | 2-Cl |
| 3 | H | H | H | 1 | 5-Br |
| 3 | H | H | H | 2 | 5-Br |
| 3 | H | H | H | 3 | 5-Br |
| 3 | H | H | H | 4 | 5-Br |
| 3 | H | H | H | 5 | 5-Br |
| 3 | H | H | H | 6 | 5-Br |
| 3 | H | H | H | 1 | 2-Cl, 6-CH$_3$ |
| 3 | H | H | H | 2 | 2-Cl, 6-CH$_3$ |
| 3 | H | H | H | 4 | 2-Cl, 6-CH$_3$ |
| 3 | H | H | H | 3 | 2-Cl, 6-CH$_3$ |
| 3 | H | H | H | 5 | 2-Cl, 6-CH$_3$ |
| 3 | H | H | H | 6 | 2-Cl, 6-CH$_3$ |
| 3 | H | H | H | 1 | 2,6-Cl$_2$ |
| 3 | H | H | H | 2 | 2,6-Cl$_2$ |
| 3 | H | H | H | 3 | 2,6-Cl$_2$ |
| 3 | H | H | H | 4 | 2,6-Cl$_2$ |
| 3 | H | H | H | 5 | 2,6-Cl$_2$ |
| 3 | H | H | H | 6 | 2,6-Cl$_2$ |
| 3 | H | H | H | 1 | 5,6-Cl$_2$ |
| 3 | H | H | H | 2 | 5,6-Cl$_2$ |
| 3 | H | H | H | 3 | 5,6-Cl$_2$ |
| 3 | H | H | H | 4 | 5,6-Cl$_2$ |
| 3 | H | H | H | 5 | 5,6-Cl$_2$ |
| 3 | H | H | H | 6 | 5,6-Cl$_2$ |
| 3 | H | H | H | 1 | 5,6-(OCH$_3$)$_2$ |
| 3 | H | H | H | 2 | 5,6-(OCH$_3$)$_2$ |
| 3 | H | H | H | 3 | 5,6-(OCH$_3$)$_2$ |
| 3 | H | H | H | 4 | 5,6-(OCH$_3$)$_2$ |
| 3 | H | H | H | 5 | 5,6-(OCH$_3$)$_2$ |
| 3 | H | H | H | 6 | 5,6-(OCH$_3$)$_2$ |
| 3 | H | H | H | 1 | 2-SCH$_3$ |
| 3 | H | H | H | 2 | 2-SCH$_3$ |
| 3 | H | H | H | 3 | 2-SCH$_3$ |
| 3 | H | H | H | 4 | 2-SCH$_3$ |
| 3 | H | H | H | 5 | 2-SCH$_3$ |
| 3 | H | H | H | 6 | 2-SCH$_3$ |
| 2 | H | H | H | 0 | H |
| 2 | H | H | H | 1 | H |
| 2 | H | H | H | 2 | H |
| 2 | H | H | H | 3 | H |
| 2 | H | H | H | 4 | H |
| 2 | H | H | H | 5 | H |
| 2 | H | H | H | 6 | H |
| 2 | H | H | H | 0 | 6-CH$_3$ |
| 2 | H | H | H | 1 | 6-CH$_3$ |
| 2 | H | H | H | 2 | 6-CH$_3$ |
| 2 | H | H | H | 3 | 6-CH$_3$ |
| 2 | H | H | H | 4 | 6-CH$_3$ |
| 2 | H | H | H | 5 | 6-CH$_3$ |
| 2 | H | H | H | 6 | 6-CH$_3$ |
| 2 | H | H | H | 0 | 6-Cl |
| 2 | H | H | H | 1 | 6-Cl |
| 2 | H | H | H | 2 | 6-Cl |
| 2 | H | H | H | 3 | 6-Cl |
| 2 | H | H | H | 4 | 6-Cl |
| 2 | H | H | H | 5 | 6-Cl |
| 2 | H | H | H | 6 | 6-Cl |
| 2 | H | H | H | 0 | 5-CF$_3$ |
| 2 | H | H | H | 1 | 5-CF$_3$ |
| 2 | H | H | H | 2 | 5-CF$_3$ |
| 2 | H | H | H | 3 | 5-CF$_3$ |
| 2 | H | H | H | 4 | 5-CF$_3$ |
| 2 | H | H | H | 5 | 5-CF$_3$ |
| 2 | H | H | H | 0 | 5-Cl |
| 2 | H | H | H | 6 | 5-CF$_3$ |
| 2 | H | H | H | 1 | 5-Cl |
| 2 | H | H | H | 2 | 5-Cl |
| 2 | H | H | H | 3 | 5-Cl |
| 2 | H | H | H | 4 | 5-Cl |
| 2 | H | H | H | 5 | 5-Cl |
| 2 | H | H | H | 6 | 5-Cl |
| 2 | H | H | H | 0 | 3-Cl |
| 2 | H | H | H | 1 | 3-Cl |
| 2 | H | H | H | 2 | 3-Cl |
| 2 | H | H | H | 3 | 3-Cl |
| 2 | H | H | H | 4 | 3-Cl |
| 2 | H | H | H | 5 | 3-Cl |
| 2 | H | H | H | 6 | 3-Cl |
| 2 | H | H | H | 0 | 6-F |
| 2 | H | H | H | 1 | 6-F |
| 2 | H | H | H | 2 | 6-F |
| 2 | H | H | H | 3 | 6-F |
| 2 | H | H | H | 4 | 6-F |
| 2 | H | H | H | 5 | 6-F |
| 2 | H | H | H | 6 | 6-F |
| 2 | H | H | H | 0 | 6-Br |
| 2 | H | H | H | 1 | 6-Br |
| 2 | H | H | H | 2 | 6-Br |
| 2 | H | H | H | 3 | 6-Br |
| 2 | H | H | H | 4 | 6-Br |
| 2 | H | H | H | 5 | 6-Br |
| 2 | H | H | H | 6 | 6-Br |
| 3 | H | H | H | 0 | 6-Cl |
| 3 | H | H | H | 1 | 6-Cl |
| 3 | H | H | H | 2 | 6-Cl |
| 3 | H | H | H | 3 | 6-Cl |
| 3 | H | H | H | 4 | 6-Cl |
| 3 | H | H | H | 5 | 6-Cl |
| 3 | H | H | H | 6 | 6-Cl |
| 3 | H | H | H | 0 | 5-Cl |
| 3 | H | H | H | 1 | 5-Cl |
| 2 | H | H | H | 2 | 5-Cl |
| 2 | H | H | H | 3 | 5-Cl |
| 2 | H | H | H | 4 | 5-Cl |
| 2 | H | H | H | 5 | 5-Cl |
| 2 | H | H | H | 6 | 5-Cl |
| 2 | H | H | H | 0 | 5-Br |
| 2 | H | H | H | 1 | 5-Br |
| 2 | H | H | H | 2 | 5-Br |
| 2 | H | H | H | 3 | 5-Br |
| 2 | H | H | H | 4 | 5-Br |
| 2 | H | H | H | 5 | 5-Br |
| 2 | H | H | H | 6 | 5-Br |
| 2 | H | H | H | 0 | 3,5-(CF$_3$)$_2$ |
| 2 | H | H | H | 1 | 3,5-(CF$_3$)$_2$ |
| 2 | H | H | H | 2 | 3,5-(CF$_3$)$_2$ |
| 2 | H | H | H | 3 | 3,5-(CF$_3$)$_2$ |
| 2 | H | H | H | 4 | 3,5-(CF$_3$)$_2$ |
| 2 | H | H | H | 5 | 3,5-(CF$_3$)$_2$ |
| 2 | H | H | H | 6 | 3,5-(CF$_3$)$_2$ |
| 2 | H | H | H | 0 | 4,5-(CF$_3$)$_2$ |
| 2 | H | H | H | 1 | 4,5-(CF$_3$)$_2$ |
| 2 | H | H | H | 2 | 4,5-(CF$_3$)$_2$ |
| 2 | H | H | H | 3 | 4,5-(CF$_3$)$_2$ |
| 2 | H | H | H | 4 | 4,5-(CF$_3$)$_2$ |
| 2 | H | H | H | 5 | 4,5-(CF$_3$)$_2$ |
| 2 | H | H | H | 6 | 4,5-(CF$_3$)$_2$ |
| 2 | H | H | H | 0 | 3,5-Cl$_2$ |
| 2 | H | H | H | 1 | 3,5-Cl$_2$ |

TABLE 29-continued

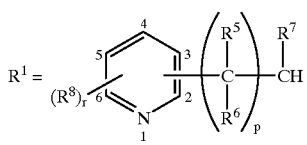

| Bonding position of heterocyclic ring | R⁵ | R⁶ | R⁷ | p | (R⁸)ᵣ |
|---|---|---|---|---|---|
| 2 | H | H | H | 2 | 3,5-Cl₂ |
| 2 | H | H | H | 3 | 3,5-Cl₂ |
| 2 | H | H | H | 4 | 3,5-Cl₂ |
| 2 | H | H | H | 5 | 3,5-Cl₂ |
| 2 | H | H | H | 6 | 3,5-Cl₂ |
| 2 | H | H | H | 0 | 3-Cl, 5-CF₃ |
| 2 | H | H | H | 1 | 3-Cl, 5-CF₃ |
| 2 | H | H | H | 2 | 3-Cl, 5-CF₃ |
| 2 | H | H | H | 3 | 3-Cl, 5-CF₃ |
| 2 | H | H | H | 4 | 3-Cl, 5-CF₃ |
| 2 | H | H | H | 5 | 3-Cl, 5-CF₃ |
| 2 | H | H | H | 6 | 3-Cl, 5-CF₃ |
| 2 | H | H | H | 0 | 3,5,6-F₃ |
| 2 | H | H | H | 0 | 3,5,6-F₃, 4CH₃ |
| 2 | H | H | H | 0 | 5-CN, 6-Cl |
| 4 | H | H | H | 0 | H |
| 4 | H | H | H | 1 | H |
| 4 | H | H | H | 2 | H |
| 4 | H | H | H | 3 | H |
| 4 | H | H | H | 4 | H |
| 4 | H | H | H | 5 | H |
| 4 | H | H | H | 6 | H |
| 4 | H | H | H | 0 | 2,3,5,6-F₄ |
| 4 | H | H | CH₃ | 0 | H |
| 4 | H | H | CH₃ | 1 | H |
| 4 | H | H | CH₃ | 2 | H |
| 4 | H | H | CH₃ | 3 | H |
| 4 | H | H | CH₃ | 4 | H |
| 4 | H | H | CH₃ | 5 | H |
| 4 | H | H | CH₃ | 6 | H |
| 2 | H | H | CH₃ | 0 | H |
| 2 | H | H | CH₃ | 1 | H |
| 2 | H | H | CH₃ | 2 | H |
| 2 | H | H | CH₃ | 3 | H |
| 2 | H | H | CH₃ | 4 | H |
| 2 | H | H | CH₃ | 5 | H |
| 2 | H | H | CH₃ | 6 | H |

TABLE 30

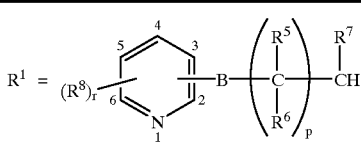

| Bonding position of heterocyclic ring | B | R⁵ | R⁶ | R⁷ | p | (R⁸)ᵣ |
|---|---|---|---|---|---|---|
| 2 | O | H | H | H | 0 | H |
| 2 | O | H | H | H | 1 | H |
| 2 | O | H | H | H | 2 | H |
| 2 | O | H | H | H | 3 | H |
| 2 | O | H | H | H | 4 | H |
| 2 | O | H | H | H | 5 | H |
| 2 | O | H | H | H | 6 | H |
| 2 | NH | H | H | H | 0 | H |
| 2 | NH | H | H | H | 1 | H |
| 2 | NH | H | H | H | 2 | H |
| 2 | NH | H | H | H | 3 | H |
| 2 | NH | H | H | H | 4 | H |
| 2 | NH | H | H | H | 5 | H |
| 2 | NH | H | H | H | 6 | H |
| 2 | S | H | H | H | 0 | H |
| 2 | S | H | H | H | 1 | H |
| 2 | S | H | H | H | 2 | H |
| 2 | S | H | H | H | 3 | H |
| 2 | S | H | H | H | 4 | H |
| 2 | S | H | H | H | 5 | H |
| 2 | S | H | H | H | 6 | H |
| 2 | O | H | H | H | 0 | 4-CH₃ |
| 2 | O | H | H | H | 1 | 4-CH₃ |
| 2 | O | H | H | H | 2 | 4-CH₃ |
| 2 | O | H | H | H | 3 | 4-CH₃ |
| 2 | O | H | H | H | 4 | 4-CH₃ |
| 2 | O | H | H | H | 5 | 4-CH₃ |
| 2 | O | H | H | H | 6 | 4-CH₃ |
| 2 | NH | H | H | H | 0 | 4-CH₃ |
| 2 | NH | H | H | H | 1 | 4-CH₃ |
| 2 | NH | H | H | H | 2 | 4-CH₃ |
| 2 | NH | H | H | H | 3 | 4-CH₃ |
| 2 | NH | H | H | H | 4 | 4-CH₃ |
| 2 | NH | H | H | H | 5 | 4-CH₃ |
| 2 | NH | H | H | H | 6 | 4-CH₃ |
| 2 | S | H | H | H | 0 | 4-CH₃ |
| 2 | S | H | H | H | 1 | 4-CH₃ |
| 2 | S | H | H | H | 2 | 4-CH₃ |
| 2 | S | H | H | H | 3 | 4-CH₃ |
| 2 | S | H | H | H | 4 | 4-CH₃ |
| 2 | S | H | H | H | 5 | 4-CH₃ |
| 2 | S | H | H | H | 6 | 4-CH₃ |
| 2 | O | H | H | H | 0 | 6-CH₃ |
| 2 | O | H | H | H | 1 | 6-CH₃ |
| 2 | O | H | H | H | 2 | 6-CH₃ |
| 2 | O | H | H | H | 3 | 6-CH₃ |
| 2 | O | H | H | H | 4 | 6-CH₃ |
| 2 | O | H | H | H | 5 | 6-CH₃ |
| 2 | O | H | H | H | 6 | 6-CH₃ |
| 2 | NH | H | H | H | 0 | 6-CH₃ |
| 2 | NH | H | H | H | 1 | 6-CH₃ |
| 2 | NH | H | H | H | 2 | 6-CH₃ |
| 2 | NH | H | H | H | 3 | 6-CH₃ |
| 2 | NH | H | H | H | 4 | 6-CH₃ |
| 2 | COO | H | H | H | 1 | H |
| 2 | COO | H | H | H | 2 | H |
| 2 | COO | H | H | H | 3 | H |
| 3 | COO | H | H | H | 1 | H |
| 3 | COO | H | H | H | 2 | H |
| 3 | COO | H | H | H | 3 | H |
| 4 | COO | H | H | H | 1 | H |
| 4 | COO | H | H | H | 2 | H |
| 4 | COO | H | H | H | 3 | H |
| 2 | COO | H | H | H | 2 | 3-Cl, 5-CF₃ |
| 2 | COO | H | H | H | 3 | 3-Cl, 5-CF₃ |
| 2 | COO | H | H | H | 2 | 5-CF₃ |
| 2 | COO | H | H | H | 3 | 5-CF₃ |
| 3 | COO | H | H | H | 2 | 6-CF₃ |
| 3 | COO | H | H | H | 3 | 6-CF₃ |
| 3 | COO | H | H | H | 2 | 6-CH₃ |
| 3 | COO | H | H | H | 3 | 6-CH₃ |
| 3 | COO | H | H | H | 2 | 6-Cl |
| 3 | COO | H | H | H | 3 | 6-Cl |
| 3 | COO | H | H | H | 2 | 6-Br |
| 3 | COO | H | H | H | 3 | 6-Br |
| 3 | COO | H | H | H | 2 | 6-I |
| 3 | COO | H | H | H | 3 | 6-I |

TABLE 30-continued $$R^1 = (R^8)_r \underset{N_1}{\overset{4}{\underset{6}{\bigcirc}}} {\overset{3}{\underset{2}{\bigcirc}}} - B - \left( \underset{R^6}{\overset{R^5}{C}} \right)_p - \underset{R^7}{\overset{}{CH}}$$

| Bonding position of heterocyclic ring | B | R⁵ | R⁶ | R⁷ | p | (R⁸)r |
|---|---|---|---|---|---|---|
| 2 | NH | H | H | H | 5 | 6-CH₃ |
| 2 | NH | H | H | H | 6 | 6-CH₃ |
| 2 | S | H | H | H | 0 | 6-CH₃ |
| 2 | S | H | H | H | 1 | 6-CH₃ |
| 2 | S | H | H | H | 2 | 6-CH₃ |
| 2 | S | H | H | H | 3 | 6-CH₃ |
| 2 | S | H | H | H | 4 | 6-CH₃ |
| 2 | S | H | H | H | 5 | 6-CH₃ |
| 2 | S | H | H | H | 6 | 6-CH₃ |
| 2 | O | H | H | H | 0 | 6-Cl |
| 2 | O | H | H | H | 1 | 6-Cl |
| 2 | O | H | H | H | 2 | 6-Cl |
| 2 | O | H | H | H | 3 | 6-Cl |
| 2 | O | H | H | H | 4 | 6-Cl |
| 2 | O | H | H | H | 5 | 6-Cl |
| 2 | O | H | H | H | 6 | 6-Cl |
| 2 | S | H | H | H | 0 | 6-Cl |
| 2 | S | H | H | H | 1 | 6-Cl |
| 2 | S | H | H | H | 2 | 6-Cl |
| 2 | S | H | H | H | 3 | 6-Cl |
| 2 | S | H | H | H | 4 | 6-Cl |
| 2 | S | H | H | H | 5 | 6-Cl |
| 2 | S | H | H | H | 6 | 6-Cl |
| 2 | NH | H | H | H | 0 | 6-Cl |
| 2 | NH | H | H | H | 1 | 6-Cl |
| 2 | NH | H | H | H | 2 | 6-Cl |
| 2 | NH | H | H | H | 3 | 6-Cl |
| 2 | NH | H | H | H | 4 | 6-Cl |
| 2 | NH | H | H | H | 5 | 6-Cl |
| 2 | NH | H | H | H | 6 | 6-Cl |
| 2 | O | H | H | H | 0 | 5-Cl |
| 2 | O | H | H | H | 1 | 5-Cl |
| 2 | O | H | H | H | 2 | 5-Cl |
| 2 | O | H | H | H | 3 | 5-Cl |
| 2 | O | H | H | H | 4 | 5-Cl |
| 2 | O | H | H | H | 5 | 5-Cl |
| 2 | O | H | H | H | 6 | 5-Cl |
| 2 | NH | H | H | H | 0 | 5-Cl |
| 2 | NH | H | H | H | 1 | 5-Cl |
| 2 | NH | H | H | H | 2 | 5-Cl |
| 2 | NH | H | H | H | 3 | 5-Cl |
| 2 | NH | H | H | H | 4 | 5-Cl |
| 2 | NH | H | H | H | 5 | 5-Cl |
| 2 | NH | H | H | H | 6 | 5-Cl |
| 2 | S | H | H | H | 0 | 5-Cl |
| 2 | S | H | H | H | 1 | 5-Cl |
| 2 | S | H | H | H | 2 | 5-Cl |
| 2 | S | H | H | H | 3 | 5-Cl |
| 2 | S | H | H | H | 4 | 5-Cl |
| 2 | S | H | H | H | 5 | 5-Cl |
| 2 | S | H | H | H | 6 | 5-Cl |
| 2 | N—CH₃ | H | H | H | 0 | 5-Cl |
| 2 | N—CH₃ | H | H | H | 1 | 5-Cl |
| 2 | N—CH₃ | H | H | H | 2 | 5-Cl |
| 2 | N—CH₃ | H | H | H | 3 | H |
| 2 | N—CH₃ | H | H | H | 4 | H |
| 2 | N—CH₃ | H | H | H | 5 | H |
| 2 | N—CH₃ | H | H | H | 6 | H |
| 2 | NH | H | H | H | 0 | 3-CH₃ |
| 2 | NH | H | H | H | 1 | 3-CH₃ |
| 2 | NH | H | H | H | 2 | 3-CH₃ |
| 2 | NH | H | H | H | 3 | 3-CH₃ |
| 2 | NH | H | H | H | 4 | 3-CH₃ |
| 2 | NH | H | H | H | 5 | 3-CH₃ |
| 2 | NH | H | H | H | 6 | 3-CH₃ |
| 2 | S | H | H | H | 0 | 3-CH₃ |
| 2 | S | H | H | H | 1 | 3-CH₃ |
| 2 | S | H | H | H | 2 | 3-CH₃ |
| 2 | S | H | H | H | 3 | 3-CH₃ |
| 2 | S | H | H | H | 4 | 3-CH₃ |
| 2 | S | H | H | H | 5 | 3-CH₃ |
| 2 | S | H | H | H | 6 | 3-CH₃ |
| 2 | O | H | H | H | 0 | 3-CH₃ |
| 2 | O | H | H | H | 1 | 3-CH₃ |
| 2 | O | H | H | H | 2 | 3-CH₃ |
| 2 | O | H | H | H | 3 | 3-CH₃ |
| 2 | O | H | H | H | 4 | 3-CH₃ |
| 2 | O | H | H | H | 5 | 3-CH₃ |
| 2 | O | H | H | H | 6 | 3-CH₃ |
| 2 | NH | H | H | H | 0 | 5-CH₃ |
| 2 | NH | H | H | H | 1 | 5-CH₃ |
| 2 | NH | H | H | H | 2 | 5-CH₃ |
| 2 | NH | H | H | H | 3 | 5-CH₃ |
| 2 | NH | H | H | H | 4 | 5-CH₃ |
| 2 | NH | H | H | H | 5 | 5-CH₃ |
| 2 | NH | H | H | H | 6 | 5-CH₃ |
| 2 | O | H | H | H | 0 | 5-CH₃ |
| 2 | O | H | H | H | 1 | 5-CH₃ |
| 2 | O | H | H | H | 2 | 5-CH₃ |
| 2 | O | H | H | H | 3 | 5-CH₃ |
| 2 | O | H | H | H | 4 | 5-CH₃ |
| 2 | O | H | H | H | 5 | 5-CH₃ |
| 2 | O | H | H | H | 6 | 5-CH₃ |
| 2 | S | H | H | H | 0 | 5-CH₃ |
| 2 | S | H | H | H | 1 | 5-CH₃ |
| 2 | S | H | H | H | 2 | 5-CH₃ |
| 2 | S | H | H | H | 3 | 5-CH₃ |
| 2 | S | H | H | H | 4 | 5-CH₃ |
| 2 | S | H | H | H | 5 | 5-CH₃ |
| 2 | S | H | H | H | 6 | 5-CH₃ |
| 2 | NH | H | H | H | 0 | 5-Br |
| 2 | NH | H | H | H | 1 | 5-Br |
| 2 | NH | H | H | H | 2 | 5-Br |
| 2 | NH | H | H | H | 3 | 5-Br |
| 2 | NH | H | H | H | 4 | 5-Br |
| 2 | NH | H | H | H | 5 | 5-Br |
| 2 | NH | H | H | H | 6 | 5-Br |
| 2 | O | H | H | H | 0 | 5-Br |
| 2 | O | H | H | H | 1 | 5-Br |
| 2 | O | H | H | H | 2 | 5-Br |
| 2 | O | H | H | H | 3 | 5-Br |
| 2 | O | H | H | H | 4 | 5-Br |
| 2 | O | H | H | H | 5 | 5-Br |
| 2 | O | H | H | H | 6 | 5-Br |
| 2 | S | H | H | H | 0 | 5-Br |
| 2 | S | H | H | H | 1 | 5-Br |
| 2 | S | H | H | H | 2 | 5-Br |
| 2 | S | H | H | H | 3 | 5-Br |
| 2 | S | H | H | H | 4 | 5-Br |
| 2 | S | H | H | H | 5 | 5-Br |
| 2 | S | H | H | H | 6 | 5-Br |
| 2 | S | H | H | H | 0 | 5-Br |
| 2 | S | H | H | H | 1 | 5-Br |
| 2 | S | H | H | H | 2 | 5-Br |
| 2 | S | H | H | H | 3 | 5-Br |
| 2 | S | H | H | H | 4 | 5-Br |
| 2 | S | H | H | H | 5 | 5-Br |
| 2 | S | H | H | H | 6 | 5-Br |
| 2 | NH | H | H | H | 0 | 4,6-(CH₃)₂ |
| 2 | NH | H | H | H | 1 | 4,6-(CH₃)₂ |
| 2 | NH | H | H | H | 2 | 4,6-(CH₃)₂ |
| 2 | NH | H | H | H | 3 | 4,6-(CH₃)₂ |

TABLE 30-continued

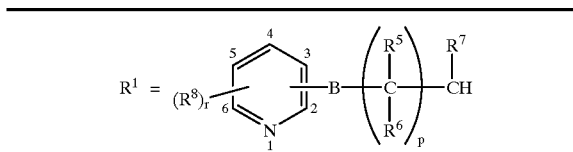

| Bonding position of heterocyclic ring | B | R⁵ | R⁶ | R⁷ | p | (R⁸)ᵣ |
|---|---|---|---|---|---|---|
| 2 | NH | H | H | H | 4 | 4,6-(CH₃)₂ |
| 2 | NH | H | H | H | 5 | 4,6-(CH₃)₂ |
| 2 | NH | H | H | H | 6 | 4,6-(CH₃)₂ |
| 2 | O | H | H | H | 0 | 4,6-(CH₃)₂ |
| 2 | O | H | H | H | 1 | 4,6-(CH₃)₂ |
| 2 | O | H | H | H | 2 | 4,6-(CH₃)₂ |
| 2 | O | H | H | H | 3 | 4,6-(CH₃)₂ |
| 2 | O | H | H | H | 4 | 4,6-(CH₃)₂ |
| 2 | O | H | H | H | 5 | 4,6-(CH₃)₂ |
| 2 | O | H | H | H | 6 | 4,6-(CH₃)₂ |
| 2 | S | H | H | H | 0 | 4,6-(CH₃)₂ |
| 2 | S | H | H | H | 1 | 4,6-(CH₃)₂ |
| 2 | S | H | H | H | 2 | 4,6-(CH₃)₂ |
| 2 | S | H | H | H | 3 | 4,6-(CH₃)₂ |
| 2 | S | H | H | H | 4 | 4,6-(CH₃)₂ |
| 2 | S | H | H | H | 5 | 4,6-(CH₃)₂ |
| 2 | S | H | H | H | 6 | 4,6-(CH₃)₂ |
| 2 | NH | H | H | H | 0 | 3-Cl, 5-CF₃ |
| 2 | NH | H | H | H | 1 | 3-Cl, 5-CF₃ |
| 2 | NH | H | H | H | 2 | 3-Cl, 5-CF₃ |
| 2 | NH | H | H | H | 3 | 3-Cl, 5-CF₃ |
| 2 | NH | H | H | H | 4 | 3-Cl, 5-CF₃ |
| 2 | NH | H | H | H | 5 | 3-Cl, 5-CF₃ |
| 2 | NH | H | H | H | 6 | 3-Cl, 5-CF₃ |
| 2 | O | H | H | H | 0 | 3-Cl, 5-CF₃ |
| 2 | O | H | H | H | 1 | 3-Cl, 5-CF₃ |
| 2 | O | H | H | H | 2 | 3-Cl, 5-CF₃ |
| 2 | O | H | H | H | 3 | 3-Cl, 5-CF₃ |
| 2 | O | H | H | H | 4 | 3-Cl, 5-CF₃ |
| 2 | O | H | H | H | 5 | 3-Cl, 5-CF₃ |
| 2 | O | H | H | H | 6 | 3-Cl, 5-CF₃ |
| 2 | S | H | H | H | 0 | 3-Cl, 5-CF₃ |
| 2 | S | H | H | H | 1 | 3-Cl, 5-CF₃ |
| 2 | S | H | H | H | 2 | 3-Cl, 5-CF₃ |
| 2 | S | H | H | H | 3 | 3-Cl, 5-CF₃ |
| 2 | S | H | H | H | 4 | 3-Cl, 5-CF₃ |
| 2 | S | H | H | H | 5 | 3-Cl, 5-CF₃ |
| 2 | S | H | H | H | 6 | 3-Cl, 5-CF₃ |
| 2 | NH | H | H | H | 0 | 5-NO₂ |
| 2 | NH | H | H | H | 1 | 5-NO₂ |
| 2 | NH | H | H | H | 0 | 3-Br, 5-CF₃ |
| 2 | NH | H | H | H | 1 | 3-Br, 5-CF₃ |
| 2 | NH | H | H | H | 2 | 3-Br, 5-CF₃ |
| 2 | NH | H | H | H | 3 | 3-Br, 5-CF₃ |
| 2 | NH | H | H | H | 4 | 3-Br, 5-CF₃ |
| 2 | NH | H | H | H | 5 | 3-Br, 5-CF₃ |
| 2 | NH | H | H | H | 6 | 3-Br, 5-CF₃ |
| 2 | O | H | H | H | 0 | 3-Br, 5-CF₃ |
| 2 | O | H | H | H | 1 | 3-Br, 5-CF₃ |
| 2 | O | H | H | H | 2 | 3-Br, 5-CF₃ |
| 2 | O | H | H | H | 3 | 3-Br, 5-CF₃ |
| 2 | O | H | H | H | 4 | 3-Br, 5-CF₃ |
| 2 | O | H | H | H | 5 | 3-Br, 5-CF₃ |
| 2 | O | H | H | H | 6 | 3-Br, 5-CF₃ |
| 2 | S | H | H | H | 0 | 3-Br, 5-CF₃ |
| 2 | S | H | H | H | 1 | 3-Br, 5-CF₃ |
| 2 | S | H | H | H | 2 | 3-Br, 5-CF₃ |
| 2 | S | H | H | H | 3 | 3-Br, 5-CF₃ |
| 2 | S | H | H | H | 4 | 3-Br, 5-CF₃ |
| 2 | S | H | H | H | 5 | 3-Br, 5-CF₃ |
| 2 | S | H | H | H | 6 | 3-Br, 5-CF₃ |
| 2 | NH | H | H | H | 0 | 3-F, 5-CF₃ |
| 2 | NH | H | H | H | 1 | 3-F, 5-CF₃ |
| 2 | NH | H | H | H | 2 | 3-F, 5-CF₃ |
| 2 | NH | H | H | H | 3 | 3-F, 5-CF₃ |
| 2 | NH | H | H | H | 4 | 3-F, 5-CF₃ |

TABLE 30-continued

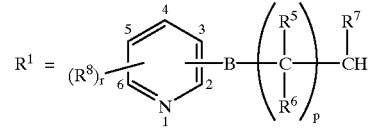

| Bonding position of heterocyclic ring | B | R⁵ | R⁶ | R⁷ | p | (R⁸)ᵣ |
|---|---|---|---|---|---|---|
| 2 | NH | H | H | H | 5 | 3-F, 5-CF₃ |
| 2 | NH | H | H | H | 6 | 3-F, 5-CF₃ |
| 2 | O | H | H | H | 0 | 3-F, 5-CF₃ |
| 2 | O | H | H | H | 1 | 3-F, 5-CF₃ |
| 2 | O | H | H | H | 2 | 3-F, 5-CF₃ |
| 2 | O | H | H | H | 3 | 3-F, 5-CF₃ |
| 2 | O | H | H | H | 4 | 3-F, 5-CF₃ |
| 2 | O | H | H | H | 5 | 3-F, 5-CF₃ |
| 2 | O | H | H | H | 6 | 3-F, 5-CF₃ |
| 2 | S | H | H | H | 0 | 3-F 5-CF₃ |
| 2 | S | H | H | H | 1 | 3-F, 5-CF₃ |
| 2 | S | H | H | H | 2 | 3-F, 5-CF₃ |
| 2 | S | H | H | H | 3 | 3-F, 5-CF₃ |
| 2 | S | H | H | H | 4 | 3-F, 5-CF₃ |
| 2 | S | H | H | H | 5 | 3-F, 5-CF₃ |
| 2 | S | H | H | H | 6 | 3-F, 5-CF₃ |
| 2 | NH | H | H | H | 2 | 5-NO₂ |
| 2 | NH | H | H | H | 3 | 5-NO₂ |
| 2 | NH | H | H | H | 4 | 5-NO₂ |
| 2 | NH | H | H | H | 5 | 5-NO₂ |
| 2 | NH | H | H | H | 6 | 5-NO₂ |
| 2 | O | H | H | H | 0 | 5-NO₂ |
| 2 | O | H | H | H | 1 | 5-NO₂ |
| 2 | O | H | H | H | 2 | 5-NO₂ |
| 2 | O | H | H | H | 3 | 5-NO₂ |
| 2 | O | H | H | H | 4 | 5-NO₂ |
| 2 | O | H | H | H | 5 | 5-NO₂ |
| 2 | O | H | H | H | 6 | 5-NO₂ |
| 2 | S | H | H | H | 0 | 5-NO₂ |
| 2 | S | H | H | H | 1 | 5-NO₂ |
| 2 | S | H | H | H | 2 | 5-NO₂ |
| 2 | S | H | H | H | 3 | 5-NO₂ |
| 2 | S | H | H | H | 4 | 5-NO₂ |
| 2 | S | H | H | H | 5 | 5-NO₂ |
| 2 | S | H | H | H | 6 | 5-NO₂ |
| 2 | NH | H | H | H | 0 | 3-NO₂, 5-Br |
| 2 | NH | H | H | H | 1 | 3-NO₂, 5-Br |
| 2 | NH | H | H | H | 2 | 3-NO₂, 5-Br |
| 2 | NH | H | H | H | 3 | 3-NO₂, 5-Br |
| 2 | NH | H | H | H | 4 | 3-NO₂, 5-Br |
| 2 | NH | H | H | H | 5 | 3-NO₂, 5-Br |
| 2 | NH | H | H | H | 6 | 3-NO₂, 5-Br |
| 2 | O | H | H | H | 0 | 3-NO₂, 5-Br |
| 2 | O | H | H | H | 1 | 3-NO₂, 5-Br |
| 2 | O | H | H | H | 2 | 3-NO₂, 5-Br |
| 2 | O | H | H | H | 3 | 3-NO₂, 5-Br |
| 2 | O | H | H | h | 4 | 3-NO₂, 5-Br |
| 2 | O | H | H | H | 5 | 3-NO₂, 5-Br |
| 2 | O | H | H | H | 6 | 3-NO₂, 5-Br |
| 2 | S | H | H | H | 0 | 3-NO₂, 5-Br |
| 2 | S | H | H | H | 1 | 3-NO₂, 5-Br |
| 2 | S | H | H | H | 2 | 3-NO₂, 5-Br |
| 2 | S | H | H | H | 3 | 3-NO₂, 5-Br |
| 2 | S | H | H | H | 4 | 3-NO₂, 5-Br |
| 2 | S | H | H | H | 5 | 3-NO₂, 5-Br |
| 2 | S | H | H | H | 6 | 3-NO₂, 5-Br |
| 2 | NH | H | H | H | 0 | 3-NO₂, 4-CH₃ |
| 2 | NH | H | H | H | 1 | 3-NO₂, 4-CH₃ |
| 2 | NH | H | H | H | 2 | 3-NO₂, 4-CH₃ |
| 2 | NH | H | H | H | 3 | 3-NO₂, 4-CH₃ |
| 2 | NH | H | H | H | 4 | 3-NO₂, 4-CH₃ |
| 2 | NH | H | H | H | 5 | 3-NO₂, 4-CH₃ |
| 2 | NH | H | H | H | 6 | 3-NO₂, 4-CH₃ |
| 2 | S | H | H | H | 0 | 3-NO₂, 4-CH₃ |
| 2 | S | H | H | H | 1 | 3-NO₂, 4-CH₃ |
| 2 | S | H | H | H | 2 | 3-NO₂, 4-CH₃ |

TABLE 30-continued

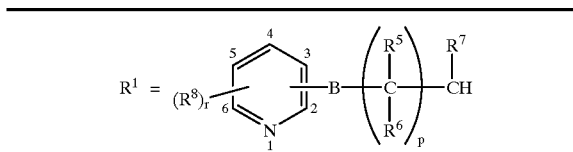

| Bonding position of heterocyclic ring | B | R⁵ | R⁶ | R⁷ | p | (R⁸)ᵣ |
|---|---|---|---|---|---|---|
| 2 | S | H | H | H | 3 | 3-NO₂, 4-CH₃ |
| 2 | S | H | H | H | 4 | 3-NO₂, 4-CH₃ |
| 2 | S | H | H | H | 5 | 3-NO₂, 4-CH₃ |
| 2 | S | H | H | H | 6 | 3-NO₂, 4-CH₃ |
| 2 | O | H | H | H | 0 | 3-NO₂, 4-CH₃ |
| 2 | O | H | H | H | 1 | 3-NO₂, 4-CH₃ |
| 2 | O | H | H | H | 2 | 3-NO₂, 4-CH₃ |
| 2 | O | H | H | H | 3 | 3-NO₂, 4-CH₃ |
| 2 | O | H | H | H | 4 | 3-NO₂, 4-CH₃ |
| 2 | O | H | H | H | 5 | 3-NO₂, 4-CH₃ |
| 2 | O | H | H | H | 6 | 3-NO₂, 4-CH₃ |
| 2 | NH | H | H | H | 0 | 4-CH₃, 5-NO₂ |
| 2 | NH | H | H | H | 1 | 4-CH₃, 5-NO₂ |
| 2 | NH | H | H | H | 2 | 4-CH₃, 5-NO₂ |
| 2 | NH | H | H | H | 3 | 4-CH₃, 5-NO₂ |
| 2 | NH | H | H | H | 4 | 4-CH₃, 5-NO₂ |
| 2 | NH | H | H | H | 5 | 4-CH₃, 5-NO₂ |
| 2 | NH | H | H | H | 6 | 4-CH₃, 5-NO₂ |
| 2 | O | H | H | H | 0 | 4-CH₃, 5-NO₂ |
| 2 | O | H | H | H | 1 | 4-CH₃, 5-NO₂ |
| 2 | O | H | H | H | 2 | 4-CH₃, 5-NO₂ |
| 2 | O | H | H | H | 0 | 3,5-(CF₃)₂ |
| 2 | O | H | H | H | 1 | 3,5-(CF₃)₂ |
| 2 | O | H | H | H | 2 | 3,5-(CF₃)₂ |
| 2 | O | H | H | H | 3 | 3,5-(CF₃)₂ |
| 2 | O | H | H | H | 4 | 3,5-(CF₃)₂ |
| 2 | O | H | H | H | 5 | 3,5-(CF₃)₂ |
| 2 | O | H | H | H | 6 | 3,5-(CF₃)₂ |
| 2 | NH | H | H | H | 0 | 3,5-(CF₃)₂ |
| 2 | NH | H | H | H | 1 | 3,5-(CF₃)₂ |
| 2 | NH | H | H | H | 2 | 3,5-(CF₃)₂ |
| 2 | NH | H | H | H | 3 | 3,5-(CF₃)₂ |
| 2 | NH | H | H | H | 4 | 3,5-(CF₃)₂ |
| 2 | NH | H | H | H | 5 | 3,5-(CF₃)₂ |
| 2 | NH | H | H | H | 6 | 3,5-(CF₃)₂ |
| 2 | S | H | H | H | 0 | 3,5-(CF₃)₂ |
| 2 | S | H | H | H | 1 | 3,5-(CF₃)₂ |
| 2 | S | H | H | H | 2 | 3,5-(CF₃)₂ |
| 2 | S | H | H | H | 3 | 3,5-(CF₃)₂ |
| 2 | S | H | H | H | 4 | 3,5-(CF₃)₂ |
| 2 | S | H | H | H | 5 | 3,5-(CF₃)₂ |
| 2 | S | H | H | H | 6 | 3,5-(CF₃)₂ |
| 2 | O | H | H | H | 0 | 5-CF₃ |
| 2 | O | H | H | H | 1 | 5-CF₃ |
| 2 | O | H | H | H | 2 | 5-CF₃ |
| 2 | O | H | H | H | 3 | 5-CF₃ |
| 2 | O | H | H | H | 4 | 5-CF₃ |
| 2 | O | H | H | H | 5 | 5-CF₃ |
| 2 | O | H | H | H | 6 | 5-CF₃ |
| 2 | S | H | H | H | 0 | 5-CF₃ |
| 2 | S | H | H | H | 1 | 5-CF₃ |
| 2 | S | H | H | H | 2 | 5-CF₃ |
| 2 | S | H | H | H | 3 | 5-CF₃ |
| 2 | S | H | H | H | 4 | 5-CF₃ |
| 2 | S | H | H | H | 5 | 5-CF₃ |
| 2 | S | H | H | H | 6 | 5-CF₃ |
| 2 | NH | H | H | H | 0 | 5-CF₃ |
| 2 | NH | H | H | H | 1 | 5-CF₃ |
| 2 | NH | H | H | H | 2 | 5-CF₃ |
| 2 | NH | H | H | H | 3 | 5-CF₃ |
| 2 | NH | H | H | H | 4 | 5-CF₃ |
| 2 | NH | H | H | H | 5 | 5-CF₃ |
| 2 | NH | H | H | H | 6 | 5-CF₃ |
| 2 | NCH₃ | H | H | H | 0 | 5-CF₃ |
| 2 | NCH₃ | H | H | H | 1 | 5-CF₃ |
| 2 | NCH₃ | H | H | H | 2 | 5-CF₃ |
| 2 | NCH₃ | H | H | H | 3 | 5-CF₃ |
| 2 | NCH₃ | H | H | H | 4 | 5-CF₃ |
| 2 | N—CH₂CH₃ | H | H | H | 0 | 5-CF₃ |
| 2 | N—CH₂CH₃ | H | H | H | 1 | 5-CF₃ |
| 2 | N—CH₂CH₃ | H | H | H | 2 | 5-CF₃ |
| 2 | N—CH₂CH₃ | H | H | H | 3 | 5-CF₃ |
| 2 | N—CH₂CH₃ | H | H | H | 4 | 5-CF₃ |
| 2 | N—(CH₂)₂CH₃ | H | H | H | 0 | 5-CF₃ |
| 2 | N—(CH₂)₂CH₃ | H | H | H | 1 | 5-CF₃ |
| 2 | N—(CH₂)₂CH₃ | H | H | H | 2 | 5-CF₃ |
| 2 | N—(CH₂)₂CH₃ | H | H | H | 3 | 5-CF₃ |
| 2 | N—(CH₂)₂CH₃ | H | H | H | 4 | 5-CF₃ |
| 2 | N—CH(CH₃)₂ | H | H | H | 0 | 5-CF₃ |
| 2 | N—CH(CH₃)₂ | H | H | H | 1 | 5-CF3 |
| 2 | N—CH(CH₃)₂ | H | H | H | 2 | 5-CF3 |
| 2 | N—CH(CH₃)₂ | H | H | H | 3 | 5-CF3 |
| 2 | N—CH(CH₃)₂ | H | H | H | 4 | 5-CF₃ |
| 2 | O | H | H | H | 3 | 4-CH₃, 5-NO₂ |
| 2 | O | H | H | H | 4 | 4-CH₃, 5-NO₂ |
| 2 | O | H | H | H | 5 | 4-CH₃, 5-NO₂ |
| 2 | O | H | H | H | 6 | 4-CH₃, 5-NO₂ |
| 2 | S | H | H | H | 0 | 4-CH₃, 5-NO₂ |
| 2 | S | H | H | H | 1 | 4-CH₃, 5-NO₂ |
| 2 | S | H | H | H | 2 | 4-CH₃, 5-NO₂ |
| 2 | S | H | H | H | 3 | 4-CH₃, 5-NO₂ |
| 2 | S | H | H | H | 4 | 4-CH₃, 5-NO₂ |
| 2 | S | H | H | H | 5 | 4-CH₃, 5-NO₂ |
| 2 | S | H | H | H | 6 | 4-CH₃, 5-NO₂ |
| 3 | O | H | H | H | 0 | H |
| 3 | O | H | H | H | 1 | H |
| 3 | O | H | H | H | 2 | H |
| 3 | O | H | H | H | 3 | H |
| 3 | O | H | H | H | 4 | H |
| 3 | O | H | H | H | 5 | H |
| 3 | O | H | H | H | 6 | H |
| 3 | O | H | H | H | 0 | 2-CH₃ |
| 3 | O | H | H | H | 1 | 2-CH₃ |
| 3 | O | H | H | H | 2 | 2-CH₃ |
| 3 | O | H | H | H | 3 | 2-CH₃ |
| 3 | O | H | H | H | 4 | 2-CH₃ |
| 3 | O | H | H | H | 5 | 2-CH₃ |
| 3 | O | H | H | H | 6 | 2-CH₃ |
| 3 | O | H | H | H | 0 | 6-CH₃ |
| 3 | O | H | H | H | 1 | 6-CH₃ |
| 3 | O | H | H | H | 2 | 6-CH₃ |
| 3 | O | H | H | H | 3 | 6-CH₃ |
| 3 | O | H | H | H | 4 | 6-CH₃ |
| 3 | O | H | H | H | 5 | 6-CH₃ |
| 3 | O | H | H | H | 6 | 6-CH₃ |
| 3 | O | H | H | H | 0 | 5-Cl |
| 3 | O | H | H | H | 1 | 5-Cl |
| 3 | O | H | H | H | 2 | 5-Cl |
| 3 | O | H | H | H | 3 | 5-Cl |
| 3 | O | H | H | H | 4 | 5-Cl |
| 3 | O | H | H | H | 5 | 5-Cl |
| 3 | O | H | H | H | 6 | 5-Cl |
| 3 | O | H | H | H | 0 | 2-Cl |
| 3 | O | H | H | H | 1 | 2-Cl |
| 3 | O | H | H | H | 2 | 2-Cl |
| 3 | O | H | H | H | 3 | 2-Cl |
| 3 | O | H | H | H | 4 | 2-Cl |
| 3 | O | H | H | H | 5 | 2-Cl |
| 3 | O | H | H | H | 6 | 2-Cl |
| 3 | O | H | H | H | 0 | 2-Br |
| 3 | O | H | H | H | 1 | 2-Br |
| 3 | O | H | H | H | 2 | 2-Br |

TABLE 30-continued

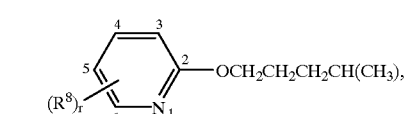

| Bonding position of heterocyclic ring | B | $R^5$ | $R^6$ | $R^7$ | p | $(R^8)_r$ |
|---|---|---|---|---|---|---|
| 3 | O | H | H | H | 3 | 2-Br |
| 3 | O | H | H | H | 4 | 2-Br |
| 3 | O | H | H | H | 5 | 2-Br |
| 3 | O | H | H | H | 6 | 2-Br |
| 3 | O | H | H | H | 0 | 2-I, 6-$CH_3$ |
| 3 | O | H | H | H | 1 | 2-I, 6-$CH_3$ |
| 3 | O | H | H | H | 2 | 2-I, 6-$CH_3$ |
| 3 | O | H | H | H | 3 | 2-I, 6-$CH_3$ |
| 3 | O | H | H | H | 4 | 2-I, 6-$CH_3$ |
| 3 | O | H | H | H | 5 | 2-I, 6-$CH_3$ |
| 3 | O | H | H | H | 6 | 2-I, 6-$CH_3$ |
| 3 | NH | H | H | H | 0 | H |
| 3 | NH | H | H | H | 1 | H |
| 3 | NH | H | H | H | 2 | H |
| 3 | NH | H | H | H | 3 | H |
| 3 | NH | H | H | H | 4 | H |
| 3 | NH | H | H | H | 5 | H |
| 3 | NH | H | H | H | 6 | H |
| 3 | NH | H | H | H | 0 | 2-Cl |
| 3 | NH | H | H | H | 1 | 2-Cl |
| 3 | NH | H | H | H | 2 | 2-Cl |
| 3 | NH | H | H | H | 3 | 2-Cl |
| 3 | NH | H | H | H | 4 | 2-Cl |
| 3 | NH | H | H | H | 5 | 2-Cl |
| 3 | NH | H | H | H | 6 | 2-Cl |
| 3 | NH | H | H | H | 0 | 5-$OCH_3$ |
| 3 | NH | H | H | H | 1 | 5-$OCH_3$ |
| 3 | NH | H | H | H | 2 | 5-$OCH_3$ |
| 3 | NH | H | H | H | 3 | 5-$OCH_3$ |
| 3 | NH | H | H | H | 4 | 5-$OCH_3$ |
| 3 | NH | H | H | H | 5 | 5-$OCH_3$ |
| 3 | NH | H | H | H | 6 | 5-$OCH_3$ |
| 3 | NH | H | H | H | 0 | 2,6-$(OCH_3)_2$ |
| 3 | NH | H | H | H | 1 | 2,6-$(OCH_3)_2$ |
| 3 | NH | H | H | H | 2 | 2,6-$(OCH_3)_2$ |
| 3 | NH | H | H | H | 3 | 2,6-$(OCH_3)_2$ |
| 3 | NH | H | H | H | 4 | 2,6-$(OCH_3)_2$ |
| 3 | NH | H | H | H | 5 | 2,6-$(OCH_3)_2$ |
| 3 | NH | H | H | H | 6 | 2,6-$(OCH_3)_2$ |
| 4 | S | H | H | H | 0 | H |
| 4 | S | H | H | H | 1 | H |
| 4 | S | H | H | H | 2 | H |
| 4 | S | H | H | H | 3 | H |
| 4 | S | H | H | H | 4 | H |
| 4 | S | H | H | H | 5 | H |
| 4 | S | H | H | H | 6 | H |
| 4 | NH | H | H | H | 0 | H |
| 4 | NH | H | H | H | 1 | H |
| 4 | NH | H | H | H | 2 | H |
| 4 | NH | H | H | H | 3 | H |
| 4 | NH | H | H | H | 4 | H |
| 4 | NH | H | H | H | 5 | H |
| 4 | NH | H | H | H | 6 | H |
| 4 | NH | H | H | H | 0 | H |
| 4 | O | H | H | H | 1 | H |
| 4 | O | H | H | H | 2 | H |
| 4 | O | H | H | H | 3 | H |
| 4 | O | H | H | H | 4 | H |
| 4 | O | H | H | H | 5 | H |
| 4 | O | H | H | H | 6 | H |
| 4 | S | H | H | H | 0 | 2,3,5,6-$Cl_4$ |
| 4 | S | H | H | H | 1 | 2,3,5,6-$Cl_4$ |
| 4 | S | H | H | H | 2 | 2,3,5,6-$Cl_4$ |
| 4 | S | H | H | H | 3 | 2,3,5,6-$Cl_4$ |
| 4 | S | H | H | H | 4 | 2,3,5,6-$Cl_4$ |
| 4 | S | H | H | H | 5 | 2,3,5,6-$Cl_4$ |
| 4 | S | H | H | H | 6 | 2,3,5,6-$Cl_4$ |

TABLE 31

$R^1$ =

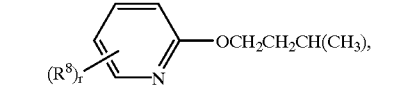

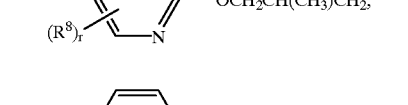

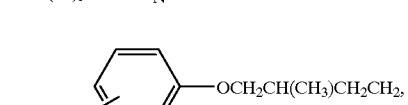

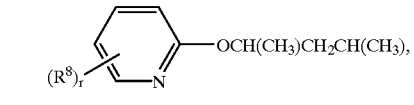

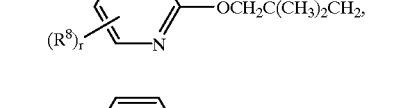

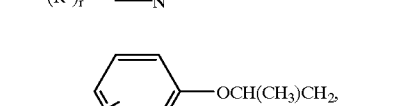

TABLE 32

R¹ =

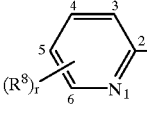 —SCH₂CH₂CH₂CH(CH₃),

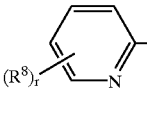 —SHC₂CH₂CH(CH₃),

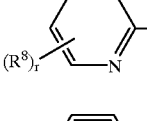 —SCH₂CH(CH₃)CH₂,

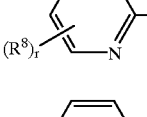 —SCH₂CH₂CH(CH₃)CH₂,

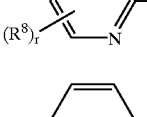 —SCH₂CH(CH₃)CH₂CH₂,

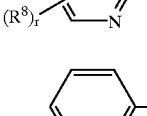 —SCH(CH₃)CH₂CH(CH₃),

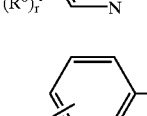 —SCH₂C(CH₃)₂CH₂,

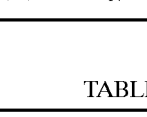 —SCH(CH₃)CH(CH₃)CH₂,

TABLE 33

R¹ =

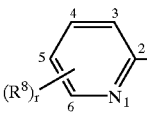 —NHCH₂CH₂CH₂CH(CH₃),

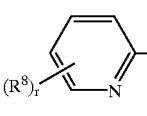 —NHCH₂CH₂CH(CH₃),

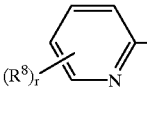 —NHCH₂CH(CH₃)CH₂,

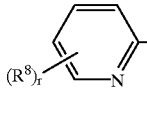 —NHCH₂CH₂CH(CH₃)CH₂,

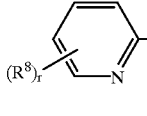 —NHCH₂CH(CH₃)CH₂CH₂,

TABLE 33-continued

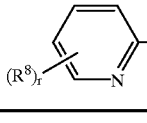 —NHCH(CH₃)CH₂CH(CH₃),

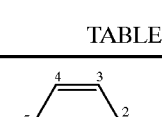 —NHCH₂C(CH₃)₂CH₂,

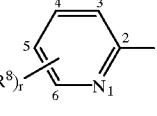 —NHCH(CH₃)CH(CH₃)CH₂,

TABLE 34

R¹ =

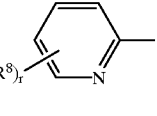 —CH₂OCH₂CH₂,

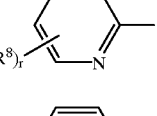 —CH₂OCH₂CH₂CH₂,

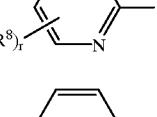 —CH₂OCH₂CH₂CH₂CH₂,

—CH₂CH₂OCH₂CH₂,

—OCH₂CH=CHCH₂,

—OCH₂C(CH₃)=C(CH₃)CH₂,

In Tables 31 to 34, (R⁸)ᵣ is defined as follows:

| (R⁸)ᵣ |
|---|
| 3-Cl, 5-CF₃ |
| 3-Br, 5-CF₃ |
| 3-F, 5-CF₃ |
| 3, 5-(CF₃)₂ |
| 5-CF₃ |
| 3, 5-Cl₂ |
| 6-Cl |
| 6-CF₃ |
| 6-Br |

TABLE 35

$R^1=$ pyridine with $(R^8)_r$, positions 1(N),2,3,4,5, substituted at 3 with $-C(R^{13})=C(R^{14})-(C(R^5)(R^6))_p-CHR^7$

| $(R^8)_r$ | $R^{13}$ | $R^{14}$ | $R^5$ | $R^6$ | p | $R^7$ |
|---|---|---|---|---|---|---|
| H | H | H | H | H | 0 | H |
| H | H | H | H | H | 1 | H |
| 6-Cl | H | H | H | H | 0 | H |
| 6-Cl | H | H | H | H | 1 | H |
| 6-Br | H | H | H | H | 0 | H |
| 6-Br | H | H | H | H | 1 | H |
| 6-F | H | H | H | H | 0 | H |
| 6-F | H | H | H | H | 1 | H |
| 6-I | H | H | H | H | 0 | H |
| 6-I | H | H | H | H | 1 | H |
| 6-CH$_3$ | H | H | H | H | 0 | H |
| 6-CH$_3$ | H | H | H | H | 1 | H |
| 6-CF$_3$ | H | H | H | H | 0 | H |
| 6-CF$_3$ | H | H | H | H | 1 | H |
| 6-Cl | CH$_3$ | H | H | H | 0 | H |
| 6-Cl | CH$_3$ | H | H | H | 1 | H |
| 6-CH$_3$ | CH$_3$ | CH$_3$ | H | H | 0 | H |
| 6-CH$_3$ | CH$_3$ | CH$_3$ | H | H | 1 | H |
| 6-CF$_3$ | CH$_3$ | CH$_3$ | H | H | 0 | H |
| 6-CF$_3$ | CH$_3$ | CH$_3$ | H | H | 1 | H |
| 6-Cl | CH$_3$ | CH$_3$ | H | H | 0 | H |
| 6-Cl | CH$_3$ | CH$_3$ | H | H | 1 | H |
| 6-CH$_3$ | CH$_3$ | CH$_3$ | H | H | 0 | H |
| 6-CH$_3$ | CH$_3$ | CH$_3$ | H | H | 1 | H |
| 6-CF$_3$ | CH$_3$ | CH$_3$ | H | H | 0 | H |
| 6-CF$_3$ | CH$_3$ | CH$_3$ | H | H | 1 | H |

TABLE 36

$R^1=$ pyridine substituted at 2 with $-C(R^{13})=C(R^{14})-(C(R^5)(R^6))_p-CHR^7$

| $(R^8)_r$ | $R^{13}$ | $R^{14}$ | $R^5$ | $R^6$ | p | $R^7$ |
|---|---|---|---|---|---|---|
| H | H | H | H | H | 0 | H |
| H | H | H | H | H | 1 | H |
| 5-Cl | H | H | H | H | 0 | H |
| 5-Cl | H | H | H | H | 1 | H |
| 5-Br | H | H | H | H | 0 | H |
| 5-Br | H | H | H | H | 1 | H |
| 5-F | H | H | H | H | 0 | H |
| 5-F | H | H | H | H | 1 | H |
| 5-I | H | H | H | H | 0 | H |
| 5-I | H | H | H | H | 1 | H |
| 5-CH$_3$ | H | H | H | H | 0 | H |
| 5-CH$_3$ | H | H | H | H | 1 | H |
| 5-CF$_3$ | H | H | H | H | 0 | H |
| 5-CF$_3$ | H | H | H | H | 1 | H |
| 5-Cl | CH$_3$ | H | H | H | 0 | H |
| 5-Cl | CH$_3$ | H | H | H | 1 | H |
| 5-CH$_3$ | CH$_3$ | CH$_3$ | H | H | 0 | H |
| 5-CH$_3$ | CH$_3$ | CH$_3$ | H | H | 1 | H |
| 5-CF$_3$ | CH$_3$ | CH$_3$ | H | H | 0 | H |
| 5-CF$_3$ | CH$_3$ | CH$_3$ | H | H | 1 | H |
| 5-Cl | CH$_3$ | CH$_3$ | H | H | 0 | H |
| 5-Cl | CH$_3$ | CH$_3$ | H | H | 1 | H |
| 5-CH$_3$ | CH$_3$ | CH$_3$ | H | H | 0 | H |
| 5-CH$_3$ | CH$_3$ | CH$_3$ | H | H | 1 | H |
| 5-CF$_3$ | CH$_3$ | CH$_3$ | H | H | 0 | H |
| 5-CF$_3$ | CH$_3$ | CH$_3$ | H | H | 1 | H |

TABLE 37

$R^1=$ pyridine substituted at 2 with $-O-(C(R^{11})(R^{12}))_s-C(O)-(C(R^5)(R^6))_p-CHR^7$

| $(R^8)_r$ | $R^{11}$ | $R^{12}$ | s | $R^5$ | $R^6$ | p | $R^7$ |
|---|---|---|---|---|---|---|---|
| H | H | H | 1 | H | H | 1 | H |
| H | H | H | 2 | H | H | 1 | H |
| 5-Cl | H | H | 1 | H | H | 1 | H |
| 5-Cl | H | H | 2 | H | H | 1 | H |
| 5-CF$_3$ | H | H | 1 | H | H | 1 | H |
| 5-CF$_3$ | H | H | 2 | H | H | 1 | H |

TABLE 38

$R^1=$ pyridine substituted at 3 with $-C(R^{13})=C(R^{14})-C(O)-(C(R^5)(R^6))_p-CHR^7$

| $(R^8)_r$ | $R^{13}$ | $R^{14}$ | $R^5$ | $R^6$ | p | $R^7$ |
|---|---|---|---|---|---|---|
| H | H | H | H | H | 1 | H |
| H | H | H | H | H | 2 | H |
| 6-Cl | H | H | H | H | 1 | H |
| 6-Cl | H | H | H | H | 2 | H |
| 6-Br | H | H | H | H | 1 | H |
| 6-Br | H | H | H | H | 2 | H |
| 6-F | H | H | H | H | 1 | H |
| 6-F | H | H | H | H | 2 | H |
| 6-I | H | H | H | H | 1 | H |
| 6-I | H | H | H | H | 2 | H |
| 6-CH$_3$ | H | H | H | H | 1 | H |
| 6-CH$_3$ | H | H | H | H | 2 | H |
| 6-CF$_3$ | H | H | H | H | 1 | H |
| 6-CF$_3$ | H | H | H | H | 2 | H |

TABLE 39

$R^1=$ pyridine substituted at 2 with $-C(R^{13})=C(R^{14})-C(O)-(C(R^5)(R^6))_p-CHR^7$

| $(R^8)_r$ | $R^{13}$ | $R^{14}$ | $R^5$ | $R^6$ | p | $R^7$ |
|---|---|---|---|---|---|---|
| H | H | H | H | H | 1 | H |
| H | H | H | H | H | 2 | H |
| 5-Cl | H | H | H | H | 1 | H |
| 5-Cl | H | H | H | H | 2 | H |
| 5-Br | H | H | H | H | 1 | H |
| 5-Br | H | H | H | H | 2 | H |
| 5-F | H | H | H | H | 1 | H |
| 5-F | H | H | H | H | 2 | H |
| 5-I | H | H | H | H | 1 | H |
| 5-I | H | H | H | H | 2 | H |
| 5-CH$_3$ | H | H | H | H | 1 | H |
| 5-CH$_3$ | H | H | H | H | 2 | H |
| 5-CF$_3$ | H | H | H | H | 1 | H |
| 5-CF$_3$ | H | H | H | H | 2 | H |

TABLE 40

$R^1 = $ pyridine structure with $(R^8)_r$, positions 1-6, linked to $-C(R^{11})(R^{12})-_s-B-[C(R^5)(R^6)]_p-CHR^7$

| $(R^8)_r$ | $R^{11}$ | $R^{12}$ | s | B | $R^5$ | $R^6$ | p | $R^7$ |
|---|---|---|---|---|---|---|---|---|
| H | H | H | 1 | COO | H | H | 1 | H |
| H | H | H | 2 | COO | H | H | 1 | H |
| H | H | H | 1 | COO | H | H | 2 | H |
| H | H | H | 2 | COO | H | H | 2 | H |
| 6-CH$_3$ | H | H | 1 | COO | H | H | 1 | H |
| 6-CH$_3$ | H | H | 2 | COO | H | H | 1 | H |
| 6-CH$_3$ | H | H | 1 | COO | H | H | 2 | H |
| 6-CH$_3$ | H | H | 2 | COO | H | H | 2 | H |

TABLE 41

$R^1 = $ quinoline structure with $(R^8)_r$, linked to $-B-[C(R^5)(R^6)]_p-CHR^7$

| Bonding position of heterocyclic ring | B | $(R_8)_r$ | $R^5$ | $R^6$ | p | $R^7$ |
|---|---|---|---|---|---|---|
| 2 | COO | H | H | H | 2 | H |
| 2 | COO | H | H | H | 3 | H |
| 3 | COO | H | H | H | 2 | H |
| 3 | COO | H | H | H | 3 | H |
| 2 | O | H | H | H | 1 | H |
| 2 | O | H | H | H | 2 | H |
| 2 | O | H | H | H | 3 | H |
| 2 | S | H | H | H | 1 | H |
| 2 | S | H | H | H | 2 | H |
| 2 | S | H | H | H | 3 | H |
| 2 | NH | H | H | H | 1 | H |
| 2 | NH | H | H | H | 2 | H |
| 2 | NH | H | H | H | 3 | H |
| 2 | NH | H | H | H | 1 | H |
| 2 | NH | H | H | H | 2 | H |
| 2 | NH | H | H | H | 3 | H |

TABLE 42

$R^1 = $ benzodioxine structure with $(R^8)_r$, linked to $-[C(R^5)(R^6)]_p-CHR^7$

| $(R^8)_r$ | $R^5$ | $R^6$ | p | $R^7$ |
|---|---|---|---|---|
| H | H | H | 0 | H |
| H | H | H | 1 | H |
| H | H | H | 2 | H |
| H | H | H | 3 | H |

TABLE 43

$R^1 = $ 2-pyridone structure with $(R^8)_r$, linked to $-C(R^5)(R^6)_p-CHR^7$

| $(R^8)_r$ | $R^5$ | $R^6$ | p | $R^7$ |
|---|---|---|---|---|
| 3-Br, 5-CF$_3$ | H | H | 1 | H |
| 3-Br, 5-CF$_3$ | H | H | 2 | H |
| 3-Br, 5-CF$_3$ | H | H | 3 | H |
| 3-Cl, 5-CF$_3$ | H | H | 1 | H |
| 3-Cl, 5-CF$_3$ | H | H | 2 | H |
| 3-Cl, 5-CF$_3$ | H | H | 3 | H |
| 3-F, 5-CF$_3$ | H | H | 1 | H |
| 3-F, 5-CF$_3$ | H | H | 2 | H |
| 3-F, 5-CF$_3$ | H | H | 3 | H |
| 3,5-(CF$_3$)$_2$ | H | H | 1 | H |
| 3,5-(CF$_3$)$_2$ | H | H | 2 | H |
| 3,5-(CF$_3$)$_2$ | H | H | 3 | H |
| 5-CF$_3$ | H | H | 1 | H |
| 5-CF$_3$ | H | H | 2 | H |
| 5-CF$_3$ | H | H | 3 | H |

TABLE 44

$R^1 = $ 1,3-dioxolane structure with $(R^8)_r$, linked to $-[C(R^5)(R^6)]_p-CHR^7$

| $(R^8)_r$ | $R^5$ | $R^6$ | p | $R^7$ |
|---|---|---|---|---|
| C$_6$H$_5$ | H | H | 0 | H |
| C$_6$H$_5$ | H | H | 1 | H |
| C$_6$H$_5$ | H | H | 2 | H |
| C$_6$H$_5$ | H | H | 3 | H |
| C$_6$H$_4$(4-Cl) | H | H | 0 | H |
| C$_6$H$_4$(4-Cl) | H | H | 1 | H |
| C$_6$H$_4$(4-Cl) | H | H | 2 | H |
| C$_6$H$_4$(4-Cl) | H | H | 3 | H |
| C$_6$H$_4$(4-CF$_3$) | H | H | 0 | H |
| C$_6$H$_4$(4-CF$_3$) | H | H | 1 | H |
| C$_6$H$_4$(4-CF$_3$) | H | H | 2 | H |
| C$_6$H$_4$(4-CF$_3$) | H | H | 3 | H |
| C$_6$H$_4$(4-OCF$_3$) | H | H | 0 | H |
| C$_6$H$_4$(4-OCF$_3$) | H | H | 1 | H |
| C$_6$H$_4$(4-OCF$_3$) | H | H | 2 | H |
| C$_6$H$_4$(4-OCF$_3$) | H | H | 3 | H |
| C$_6$H$_4$(4-Br) | H | H | 0 | H |
| C$_6$H$_4$(4-Br) | H | H | 1 | H |
| C$_6$H$_4$(4-Br) | H | H | 2 | H |
| C$_6$H$_4$(4-Br) | H | H | 3 | H |

TABLE 45

$R^1 = $ benzothiazole-like structure with $(R^8)_r$, linked to $-B-[C(R^5)(R^6)]_p-CHR^7$

| $(R^8)_r$ | R | B | $R^5$ | $R^6$ | p | $R^7$ |
|---|---|---|---|---|---|---|
| H | S | S | H | H | 1 | H |
| H | S | S | H | H | 2 | H |

TABLE 45-continued

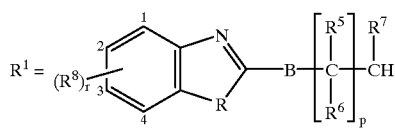

| (R⁸)ᵣ | R | B | R⁵ | R⁶ | p | R⁷ |
|---|---|---|---|---|---|---|
| H | S | O | H | H | 1 | H |
| H | S | O | H | H | 2 | H |
| H | S | NH | H | H | 1 | H |
| H | S | NH | H | H | 2 | H |
| H | S | S | H | H | 2 | H |
| H | S | O | H | H | 2 | H |
| 2-CF₃ | S | NH | H | H | 2 | H |
| 2-CF₃ | S | S | H | H | 2 | H |
| 2-CF₃ | S | O | H | H | 2 | H |
| 3-CF₃ | S | NH | H | H | 2 | H |
| 3-CF₃ | S | S | H | H | 2 | H |
| 3-CF₃ | S | O | H | H | 2 | H |
| 2-OCF₃ | S | NH | H | H | 2 | H |
| 2-OCF₃ | S | S | H | H | 2 | H |
| 2-OCF₃ | S | O | H | H | 2 | H |
| 3-OCF₃ | S | NH | H | H | 2 | H |
| 3-OCF₃ | S | S | H | H | 2 | H |
| 3-OCF₃ | S | O | H | H | 2 | H |
| 2-Cl | S | NH | H | H | 2 | H |
| 2-Cl | S | S | H | H | 2 | H |
| 2-Cl | S | O | H | H | 2 | H |
| 3-Cl | S | NH | H | H | 2 | H |
| 3-Cl | S | S | H | H | 2 | H |
| 3-Cl | S | O | H | H | 2 | H |
| 3-Cl | S | NH | H | H | 2 | H |
| 2-Br | S | S | H | H | 2 | H |
| 2-Br | S | O | H | H | 2 | H |
| 2-Br | S | NH | H | H | 2 | H |
| 3-Br | S | S | H | H | 2 | H |
| 3-Br | S | O | H | H | 2 | H |
| 3-Br | S | NH | H | H | 2 | H |
| 3,4-(CH₃)₂ | S | S | H | H | 2 | H |
| 3,4-(CH₃)₂ | S | O | H | H | 2 | H |
| 3,4-(CH₃)₂ | S | NH | H | H | 2 | H |
| 3-OCH₃ | S | S | H | H | 2 | H |
| 3-OCH₃ | S | O | H | H | 2 | H |
| 3-OCH₃ | S | NH | H | H | 2 | H |
| 3-OCH₂CH₃ | S | S | H | H | 2 | H |
| 3-OCH₂CH₃ | S | O | H | H | 2 | H |
| 3-OCH₂CH₃ | S | NH | H | H | 2 | H |
| 4-OCH₃ | S | S | H | H | 2 | H |
| 4-OCH₃ | S | O | H | H | 2 | H |
| 4-OCH₃ | S | NH | H | H | 2 | H |
| 4-OCH₂CH₃ | S | S | H | H | 2 | H |
| 4-OCH₂CH₃ | S | O | H | H | 2 | H |
| 4-OCH₂CH₃ | S | NH | H | H | 2 | H |
| 3-OCH(CH₃)₂ | S | S | H | H | 2 | H |
| 3-OCH(CH₃)₂ | S | O | H | H | 2 | H |
| 3-OCH(CH₃)₂ | S | NH | H | H | 2 | H |
| 4-OCH(CH₃)₂ | S | S | H | H | 2 | H |
| 4-OCH(CH₃)₂ | S | O | H | H | 2 | H |
| 4-OCH(CH₃)₂ | S | NH | H | H | 2 | H |
| H | NH | S | H | H | 1 | H |
| H | NH | S | H | H | 2 | H |
| 2-CH₃ | NH | S | H | H | 1 | H |
| 2-CH₃ | NH | S | H | H | 2 | H |
| 2-OCH₃ | NH | S | H | H | 1 | H |
| 2-OCH₃ | NH | S | H | H | 2 | H |
| 2-OCF₃ | NH | S | H | H | 1 | H |
| 2-OCF₃ | NH | S | H | H | 2 | H |
| 2-NO₂ | NH | S | H | H | 1 | H |
| 2-NO₂ | NH | S | H | H | 2 | H |
| 2-Cl | NH | S | H | H | 1 | H |
| 2-Cl | NH | S | H | H | 2 | H |
| 2-Br | NH | S | H | H | 1 | H |
| 2-Br | NH | S | H | H | 2 | H |
| 2-CH₃ | NH | O | H | H | 1 | H |
| 2-CH₃ | NH | NH | H | H | 2 | H |
| 2-OCH₃ | NH | O | H | H | 1 | H |

TABLE 45-continued

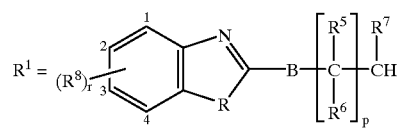

| (R⁸)ᵣ | R | B | R⁵ | R⁶ | p | R⁷ |
|---|---|---|---|---|---|---|
| 2-OCH₃ | NH | NH | H | H | 2 | H |
| 2-OCF₃ | NH | O | H | H | 1 | H |
| 2-OCF₃ | NH | NH | H | H | 2 | H |
| 2-Cl | NH | O | H | H | 1 | H |
| 2-Cl | NH | NH | H | H | 2 | H |
| 2-Br | NH | O | H | H | 1 | H |
| 2-Br | NH | NH | H | H | 2 | H |
| H | O | S | H | H | 1 | H |
| H | O | O | H | H | 1 | H |
| H | O | NH | H | H | 1 | H |
| H | O | S | H | H | 2 | H |
| H | O | O | H | H | 2 | H |
| H | O | NH | H | H | 2 | H |
| 2-Cl | O | S | H | H | 2 | H |
| 2-Cl | O | O | H | H | 2 | H |
| 2-Cl | O | NH | H | H | 2 | H |
| 3-Cl | O | S | H | H | 2 | H |
| 3-Cl | O | O | H | H | 2 | H |
| 3-Cl | O | NH | H | H | 2 | H |
| 2-CF₃ | O | S | H | H | 2 | H |
| 2-CF₃ | O | O | H | H | 2 | H |
| 2-CF₃ | O | NH | H | H | 2 | H |
| 3-CF₃ | O | S | H | H | 2 | H |
| 3-CF₃ | O | O | H | H | 2 | H |
| 3-CF₃ | O | NH | H | H | 2 | H |
| 2-OCF₃ | O | S | H | H | 2 | H |
| 2-OCF₃ | O | O | H | H | 2 | H |
| 2-OCF₃ | O | NH | H | H | 2 | H |
| 3-OCF₃ | O | S | H | H | 2 | H |
| 3-OCF₃ | O | O | H | H | 2 | H |
| 3-OCF₃ | O | NH | H | H | 2 | H |
| 2-NO₂ | NH | O | H | H | 1 | H |
| 2-NO₂ | NH | NH | H | H | 2 | H |

TABLE 46

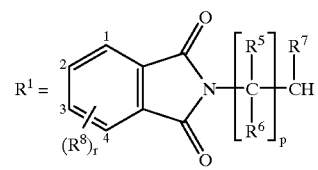

| (R⁸)ᵣ | R⁵ | R⁶ | p | R⁷ |
|---|---|---|---|---|
| H | H | H | 1 | H |
| H | H | H | 2 | H |

The aldehyde compound of the general formula [VI], which is an intermediate for use in the production of the present compounds, can be produced, for example, according to the following scheme 1:

SCHEME 1

[III] + L¹—CH₂CH(OC₂H₅)₂

↓

-continued

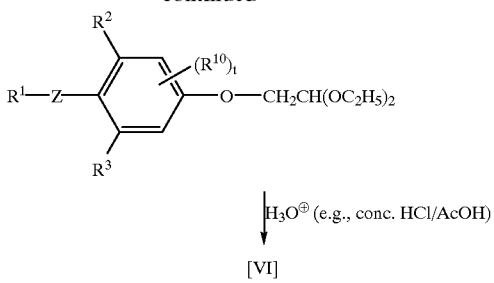

[VI]

wherein all variables are as defined above.

The compounds of the general formula [II] or [III], which are intermediate for use in the production of the present compounds, can be produced, for example, according to the following schemes 2 to 6:

SCHEME 2

(when Y and Z are both oxygen)

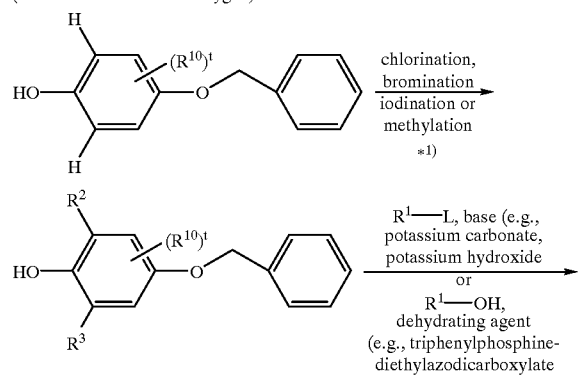

*1): see, e.g., Tetrahedron Lett., 889 (1974).
wherein $R^1$, $R^2$, $R^3$, $R^{10}$, t and L are each as defined above.

SCHEME 3

(when Y and Z are both oxygen)

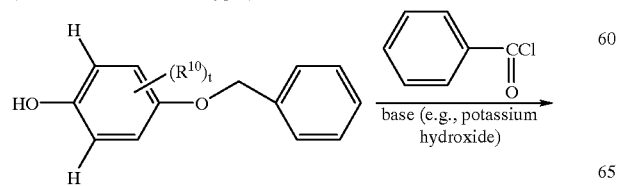

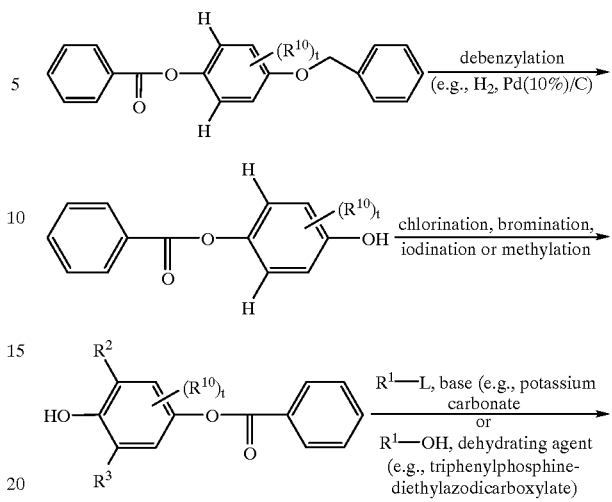

wherein $R^1$, $R^2$, $R^3$, $R^{10}$, t and L are each as defined above.

SCHEME 4

(when Y and Z are not both oxygen)

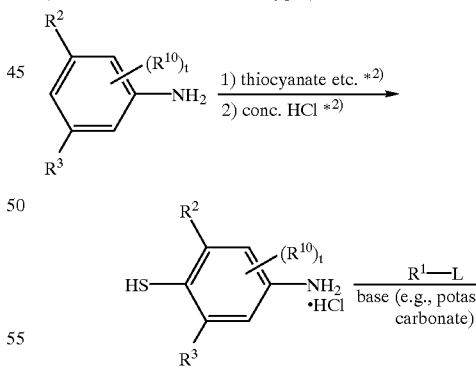

83
-continued

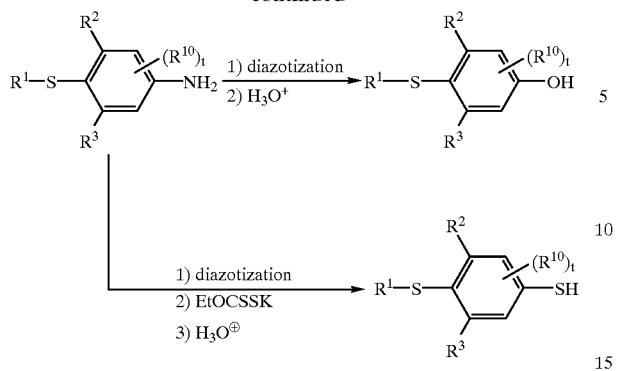

*2): see JP-A 60-181076/1985.
wherein $R^1$, $R^2$, $R^3$, $R^{10}$, t and L are each as defined above.

84
-continued

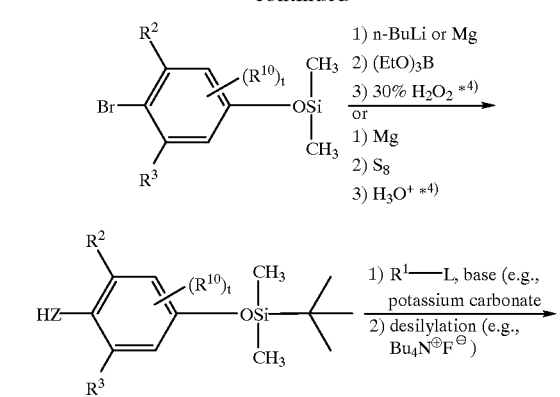

SCHEME 5

(when Y and Z are both oxygen)

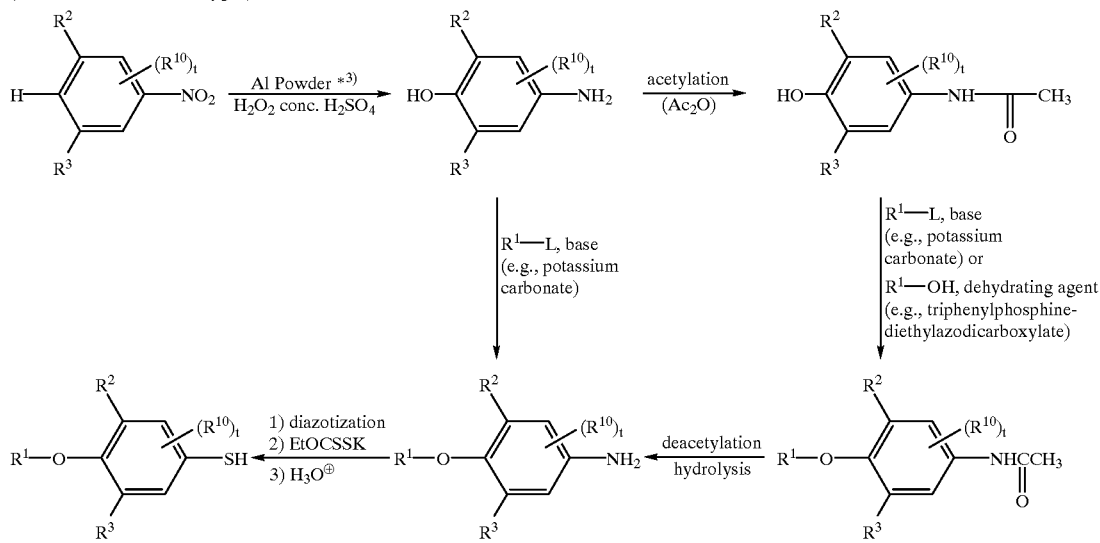

*3): See H. J. Shine, "Aromatic Rearrangement", Elsevier, 182(1967).
wherein $R^1$, $R^2$, $R^3$, $R^{10}$, t and L are each as defined above.

SCHEME 6

(when Y is oxygen)

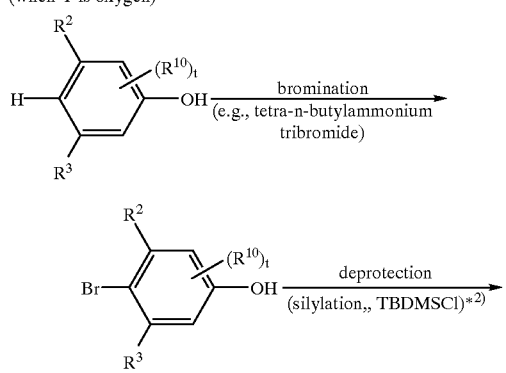

-continued

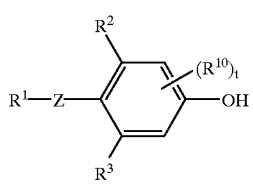

*4): see J. Org. Chem., 22, 1001 (1957)
*5): see Ber., 72, 594 (1939)
wherein $R^1$, $R^2$, $R^3$, L, $R^{10}$, t and z are each as defined above.

The compounds of the general formula [VII], which are intermediates for use in the production of the present compounds, can be produced, for example, according to the following scheme 7:

SCHEME 7

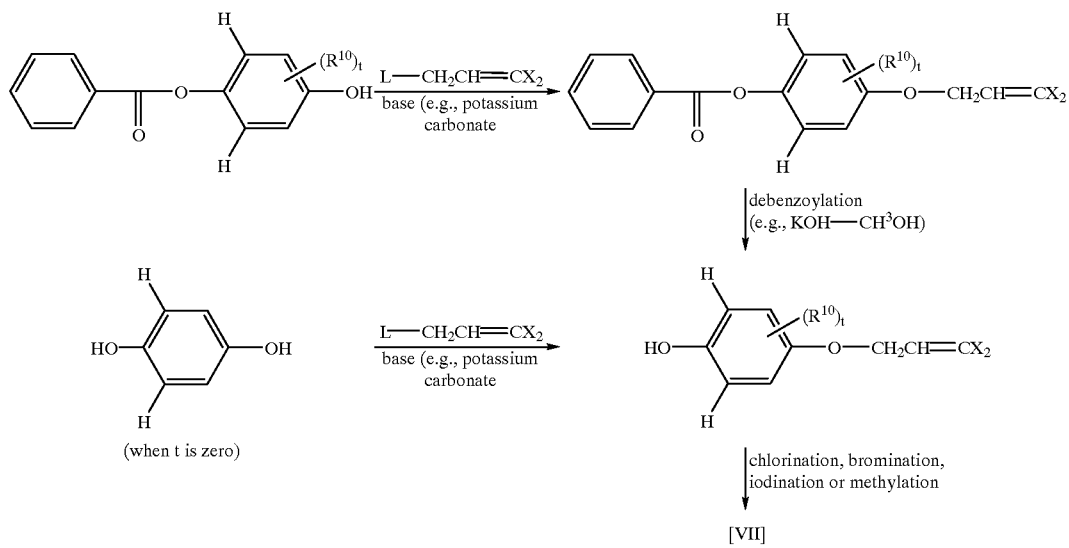

The compounds of the general formula [IV] and the alcohol compounds of the general formula [V], which are intermediates for use in the production of the present compounds, can be produced, for example, according to the following scheme 8:

SCHEME 8

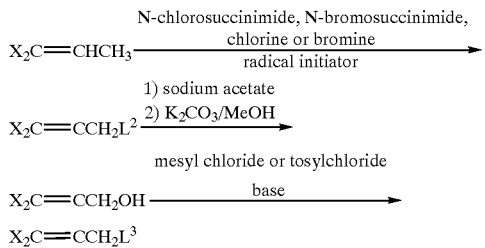

wherein $L^2$ is chlorine or bromine, $L^3$ is mesyloxy or tosyloxy, and X is as defined above.

The compounds of the general formula [VIII] or [IX] wherein $R^1$ is $R^1_1$ (wherein $R^1_1$ is $Q_1$ or $Q_2$ in the definition of $R^1$), which are intermediates for use in the production of the present compounds, can be obtained from various commercial sources or can be produced, for example, according to the schemes 9 and 10 depicted below.

The aldehyde compounds of the general formula: A—CHO (wherein A is as defined above), which are the starting compounds in the production of the compounds [VIII] or [IX], can be obtained, for example, by the processes disclosed in the following references.

Furancarbaldehydes:
  Zh. Org. Khim., 11, 1955;
  Tetrahedron., 39, 3881;
  Chem. Pharm. Bull., 28, 2846
Thiophenecarbaldehydes:
  Tetrahedron., 32, 1403;
  J. Org. Chem., 41, 2835;
  Zh. Obshch. Khim., 34, 4010;
  Bull. Soc. Chim. France., 479 (1963)
Pyrrolecarbaldehydes:
  Beilstein., 21, 1279
Isothiazolecarbaldehydes:
  J. Medicin. Chem., 13, 1208;
  J. Chem. Soc., 446 (1964)
Pyrazolecarboaldehydes:
  Chem. Ber., 97, 3407;
  J. Chem. Soc., 3314 (1957)
Imidazolecarbaldehydes:
  J. Pharm. Soc. Japan., 60, 184;
  J. Amer. Chem. Soc., 71, 2444
Thiazolecarbaldehydes:
  JP-A 59-2063701/984
  Chem. Ab., 62, 7764d;
  Chem. Ber., 101, 3872;
  JP-A 59-2063701/984
Thiadiazolecarbaldehydes:
  U.S. Pat. No. 1,113,705

SCHEME 9

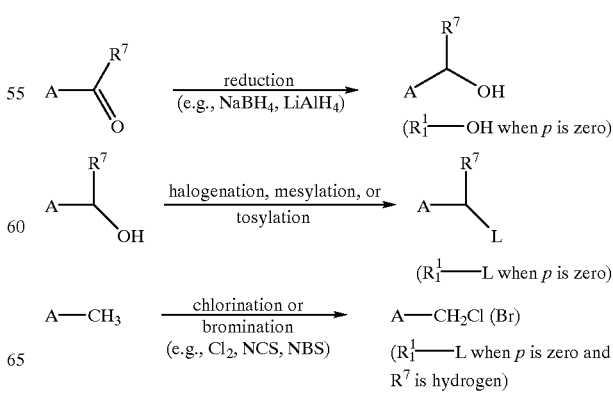

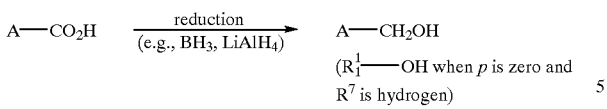

(R₁¹——OH when $p$ is zero and R⁷ is hydrogen)

wherein all the variables are each as defined above.

SCHEME 10

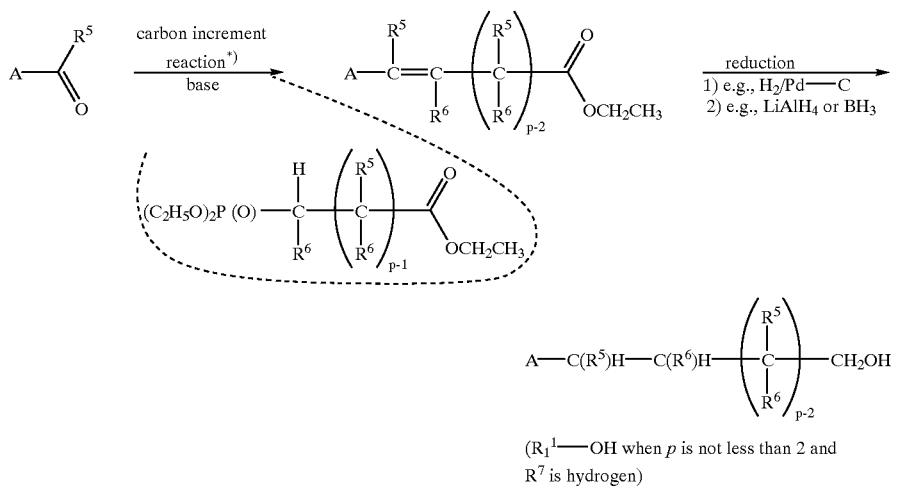

(R₁¹——OH when $p$ is not less than 2 and R⁷ is hydrogen)

*): see, e.g., *Chem.Ber.*, 95, 581 (1962).

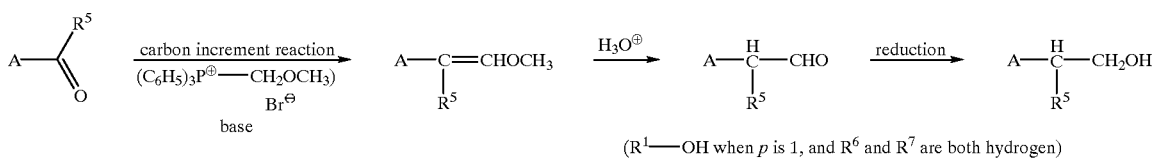

(R¹——OH when $p$ is 1, and R⁶ and R⁷ are both hydrogen)

wherein all the variables are each as defined above.

The compounds of the general formula: A—L' (wherein L' is halogen (e.g., chlorine, bromine, iodine)) included in the compounds [XI], which are intermediates for use in the production of the present compounds, can be obtained from various commercial sources or can be produced, for example, according to the following scheme 11:

SCHEME 11

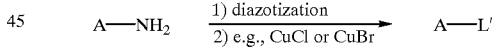

wherein A and L' are each as defined above.

The compounds [X], [XII] or [XIII], which are intermediates for use in the production of the present compounds, can be produced, for example, according to the following schemes 12 and 13:

SCHEME 12

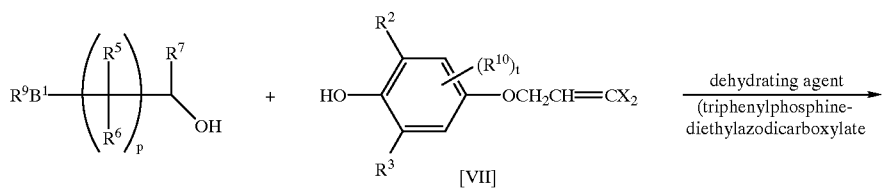

-continued
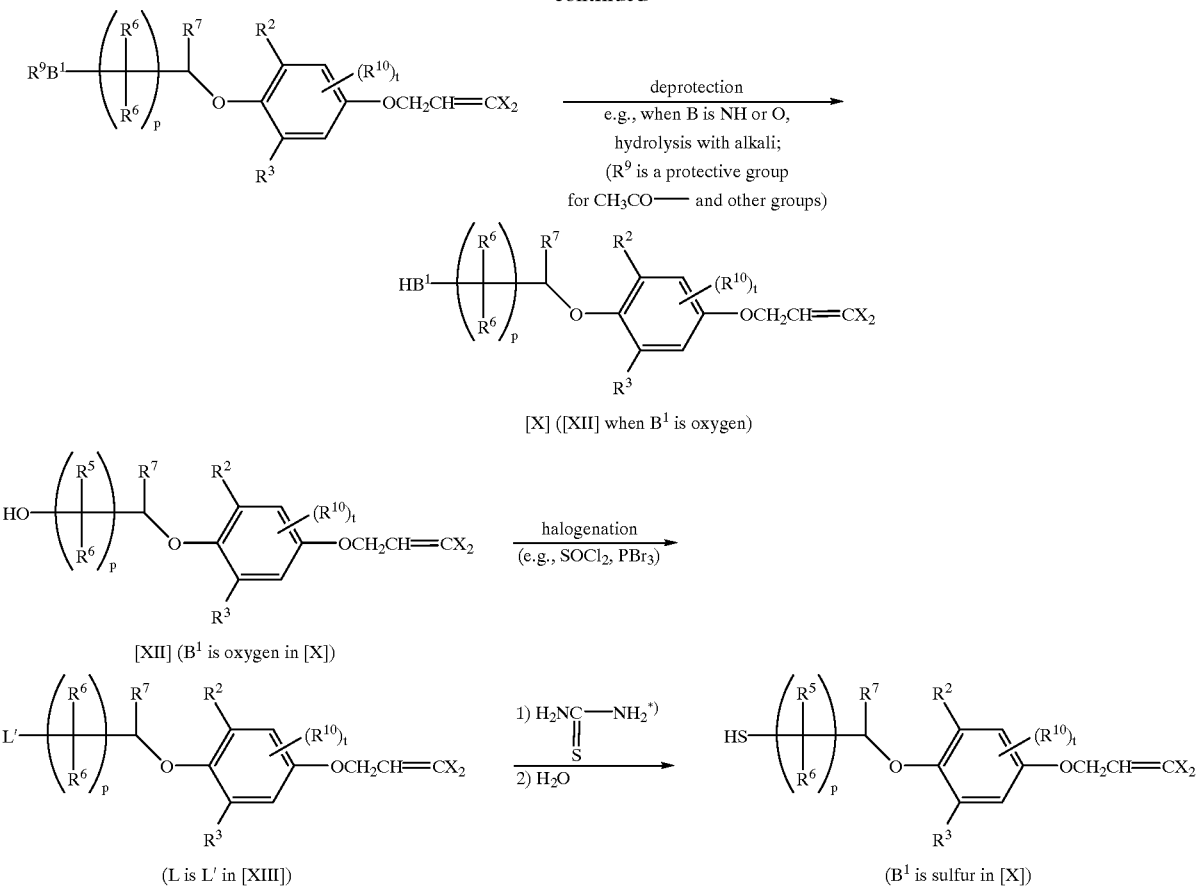
wherein all the variables are each as defined above.
*) J.Amer.Chem.Soc., 33, 440 (1905)
SCHEME 13
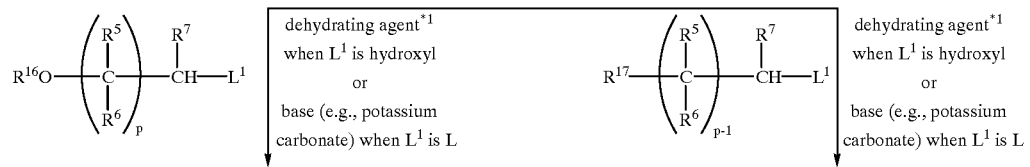

-continued

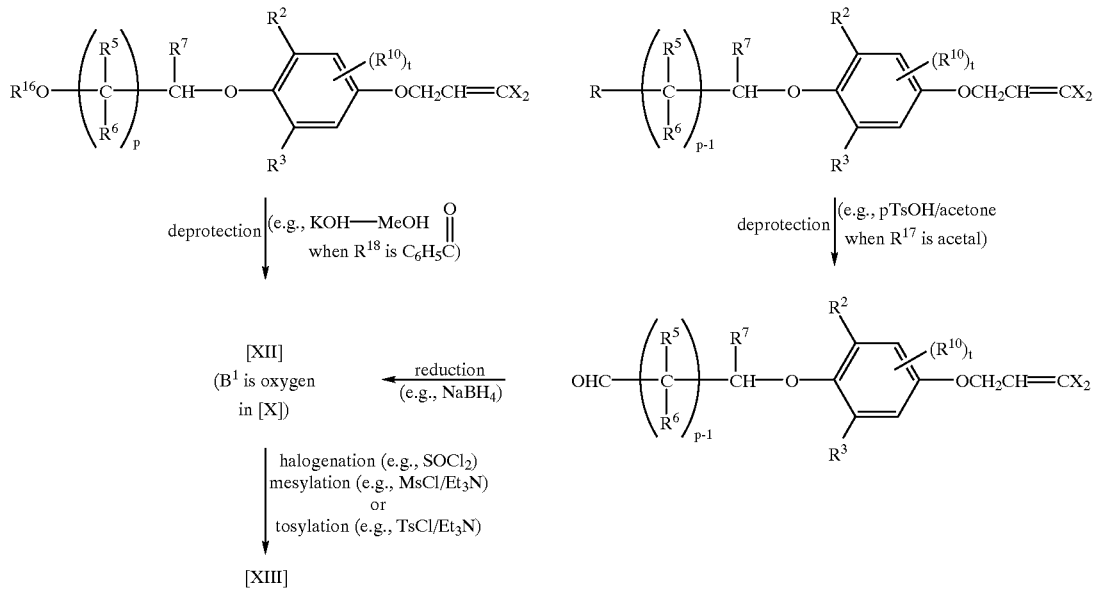

*1): e.g., triphenylphosphine-
diethylazodicarboxylate wherein $M_s$ is mesyl; $T_s$ is tosyl; $R^{16}$ is a protecting group for alcohols (e.g., benzoyl); $R^{17}$ is protected formyl (e.g., acetal); $L^1$ is hydroxy or L; and $R^2$, $R^3$, $R^7$, $R^{10}$, $R^{11}$, $R^{14}$, X, L, p and t are each as defined above.

SCHEME 14

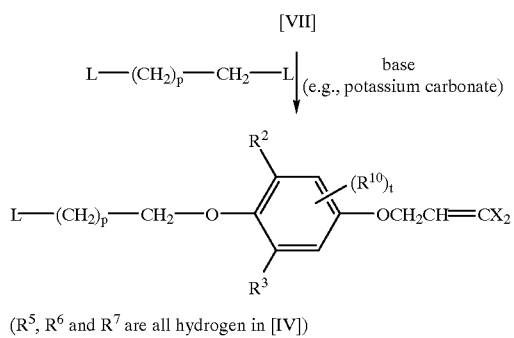

($R^5$, $R^6$ and $R^7$ are all hydrogen in [IV])

wherein all the variables are each as defined above.

The present compounds are satisfactorily effective for the control of various noxious insects, mites and ticks, examples of which are as follows:

Hemiptera:
Delphacidae such as *Laodelphax striatellus, Nilaparvata lugens* and *Sogatella furcifera,* Deltocephalidae such as *Nephotettix cincticeps* and *Nephotettix virescens,* Aphididae, Pentatomidae, Aleyrodidae, Coccidae, Tingidae, Psyllidae, etc.

Lepidoptera:
Pyralidae such as *Chilo suppressalis, Cnaphalocrocis medinalis, Ostrinia nubilalis, Parapediasia teterrella, Notarcha derogata* and *Plodia interpunctella,* Noctuidae such as *Spodoptera litura, Spodoptera exigua, Spodoptera littoralis, Pseudaletia separata, Mamestra brassicae, Agrotis ipsilon,* Trichoplusia spp., Heliothisspp., Helicoverpa spp. and Earias spp., Pieridae such as *Pieris rapae crucivora,* Tortricidae such as Adoxophyes spp., *Grapholita molesta* and *Cydia pomonella,* Carposinidae such as *Carposina niponensis,* Lyonetiidae such as Lyonetia spp., Lymantriidae such as Lymantria spp. and Euproctis spp., Yponomeutidae such as *Plutella xylostella,* Gelechiidae such as *Pectinophora gossypiella,* Arctiidae such as *Hyphantria cunea,* Tineidae such as *Tinea translucens* and *Tineola bisselliella,* etc.

Diptera:
Culex such as *Culex pipiens pallens* and *Cules tritaeniorhynchus,* Aedes such as *Aedes albopictus* and *Aedes aegypti,* Anopheles such as *Anophelinae sinensis,* Chironomidae, Muscidae such as *Musca domestica* and *Muscina stabulans,* Calliphoridae, Sarcophagidae, *Fannia canicularis,* Anthomyiidae such as *Delia Platura* and *Delia antigua,* Trypetidae, Drosophilidae, Psychodidae, Tabanidae, Simuliidae, Stomoxyinae, etc.

Coleoptera:
Diabrotica such as *Diabrotica virgifera* and *Diabrotica undecimpunctata,* Scarabaeidae such as *Anomala cuprea* and *Anomala rufocuprea,* Curculionidae such as *Lissorphoptrus oryzophilus, Hypera pastica,* and *Calosobruchys chinensis,* Tenebrionidae such as *Tenebrio molitor* and *Tribolium castaneum,* Chrysomelidae such as *Phyllotreta striolata* and *Aulacophora femoralis,* Anobiidae, Epilachna spp. such as *Henosepilachna vigintioctopunctata,* Lyctidae, Bostrychidae, Cerambycidae, *Paederus fuscipes,* etc.

Dictyoptera:
*Blattella germanica, Periplaneta fuliginosa, Peroplaneta americana, Periplaneta brunnea, Blatta orientalis,* etc.

Thysanoptera:
*Thrips palmi, Thrips hawaiiensis,* etc.

Hymenoptera:
Formicidae, Vespidae, Bethylidae, Tenthredinidae such as *Athalia rosae japonensis,* etc.

Orthoptera:
Gryllotalpidae, Acrididae, etc.

Siphonaptera:
*Purex irritans,* etc.

Anoplura:
*Pediculus humanus capitis, Phthirus pubis,* etc.
Isoptera (termites):
*Reticulitermes speratus, Coptotermes formosanus,* etc.
Acarina:
plant patasitic Tetranychidae such as *Tetranychus uriticae, Panonychus citri, Tetranychus cinnabarinus* and *Panonychus ulmi,* animal parasitic Ixodidae such as *Boophilus microphus,* house dust mites, etc.

The present compounds are also effective for the control of various noxious insects, mites and ticks having resistance to conventional insecticides and acaricides.

When the present compound is used as an active ingredient of insecticidal/acaricidal agents, it may be used as such without any addition of other ingredients. The present compound is, however, usually formulated into a dosage form such as oil sprays, emulsifiable concentrates, wettable powders, flowables, granules, dusts, aerosols, fumigants (foggings) and poison baits. These formulations are usually prepared by mixing the present compound with a solid carrier, a liquid carrier, a gaseous carrier or a bait, and if necessary, adding a surfactant and other auxiliaries used for formulation.

Each of the formulations usually contains the present compound as an active ingredient in an amount of 0.01% to 95% by weight.

Examples of the solid carrier to be used for the formulation are fine powder or granules of clay materials such as kaolin clay, diatomaceous earth, synthetic hydrated silicon oxide, bentonite, Fubasami clay and acid clay; various kinds of talc, ceramics, other inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride.

Examples of the liquid carrier are water, alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier or propellant are flon gas, butane gas, LPG (liquefied petroleum gas), dimethyl ether and carbon dioxide.

Examples of the surfactant are alkyl sulfates, alkyl sulfonates, alkyl arylsulfonates, alkyl aryl ethers and their polyoxyethylene derivatives, polyethylene glycol ethers, polyhydric alcohol esters and sugar alcohol derivatives.

Examples of the auxiliaries used for formulation, such as fixing agents or dispersing agents, are casein, gelatin, polysaccharides such as starch, gum arabic, cellulose derivatives and alginic acid, lignin derivatives, bentonite, sugars, and synthetic water-soluble polymers such as polyvinyl alcohol, polyvinyl pyrrolidone and polyacrylic acid.

Examples of the stabilizer are PAP (isopropyl acid phosphate), BHT (2,6-di-tert-butyl-4-methylphenol), BHA (mixtures of 2-t-butyl-4-methoxyphenol and 3-tert-butyl-4-methoxyphenol), vegetable oils, mineral oils, surfactants, fatty acids and their esters.

Examples of the base material to be used in the poison baits are bait materials such as grain powder, vegetable oils, sugars and crystalline cellulose; antioxidants such as dibutylhydroxytoluene and nordihydroguaiaretic acid; preservatives such as dehydroacetic acid; substances for preventing erroneous eating, such as red pepper powder, attractant flavors such as cheese flavor or onion flavor.

The formulation thus obtained is used as such or after diluted with water. The formulation may also be used in combination with other insecticides, nematocides, acaricides, bactericides, fungicides, herbicides, plant growth regulators, synergists, fertilizers, soil conditioners and/or animal feed under non-mixing conditions or pre-mixing conditions.

Examples of the insecticide, acaricide and/or nematocide which can be used are organophosphorus compounds such as Fenitrothion[(O,O-dimethyl O-(3-methyl-4-nitrophenyl) phosphorothioate], Fenthion[O,O-dimethyl O-(3-methyl-4methylthio)phenyl)phosphorothioate], Diazinon[O,O-diethyl-O-2-isopropyl-6-methylpyrimidin-4-ylphosphorothioate], Chlorpyriphos[O,O-diethyl-O-3,5,6-trichloro-2-pyridylphosphorothioate], Acephate[O,S-dimethylacetylphosphoramidothioate], Methidachion[S-2,3-dihydro-5-methoxy-2-oxo-1,3,4-thiadiazol-3-ylmethyl O,O-dimethylphosphorodithioate], Disulfoton[O,O-diethyl S-2-ethylthioethylphosphorothioate], DDVP[2,2-dichlorovinyldimethylphosphate], Sulprofos[O-ethyl O-4-(methylthio)phenyl S-propyl phosphorodithioate], Cyanophos[O-4-cyanophenyl O,O-dimethylphosphorothioate], Dioxabenzofos[2-methoxy-4H-1,3,2-benzodioxaphosphinin-2-sulfide], Dimethoate[O,O-dimethyl-S-(N-methyl-carbamoylmethyl)dithiophosphate], phenthoate[ethyl 2-dimethoxyphosphinothioylthio-(phenyl) acetate], Malathion[diethyl(dimethoxyphosphinothioylthio) succinate], Trichlorfon [dimethyl 2,2,2-trichloro-1-hydroxyethylphosphonate], Azinphos-methyl[S-3,4-dihydro-4-oxo-1,2,3-benzotriazin-3-ylmethyl-O,O,-dimethylphosphorodithioate], Monocrotophos[dimethyl (E)-1-methyl-2-(methylcarbamoyl)vinylphosphate], Ethion [O,O,O',O'-tetraethyl S,S'-methylenebis (phosphorodithioate)] and Profenfos[O-4-bromo-2-chlorophenyl O-ethyl S-propylphosphorothioate]; carbamate compounds such as BPMC[2-sec-butylphenylmethylcarbamate], Benfuracarb[ethyl N-[2,3-dihydro-2,2-dimethylbenzofuran-7-yloxycarbonyl(methyl) aminothio]-N-isopropyl-β-alaninate], Propoxur[2-isopropoxyphenyl N-methylcarbamate], Carbosulfan[2,3-dihydro-2,2-dimethyl-7-benzo[b]-furanyl N-dibutylaminothio-N-methylcarbamate], Carbaril[1-naphthyl-N-methylcarbamate], Methomyl[S-methyl-N-[(methylcarbamoyl)oxy]thioacetoimidate], Ethiofencarb[2-(ethylthiomethyl)phenylmethylcarbamate], Aldicarb[2-methyl-2-(methylthio)propanaldehyde O-methylcarbamoyloxime], Oxamyl[N,N-dimethyl-2-methylcarbamoyloxyimino- 2-(methylthio)acetamide], Alanylcarb[ethyl (Z)-N-benzyl-N-{[methyl(1-methylthioethylideneaminooxycarbonyl)amino]thio}-β-alanylate], Fenothiocarb[S-(4-phenoxy-butyl)-N,N-dimethylthiocarbamate] and Thiodicarb[3,7,9,13-tetramethyl-5,11-dioxa-2,8,14-trithia-4,7,9,12-tetraazapentadeca-3,12-dien-6,10-dione]; pyrethroid compounds such as Etofenprox[2-(4ethoxyphenyl)-2-methylpropyl-3-phenoxybenzylether], Fenvalerate[(RS)-α-cyano-3-phenoxybenzyl(RS)-2-(4-chlorophenyl)-3-methylbutyrate], Esfenvalerate[(S)-α-cyano-3-phenoxybenzyl(S)-2-(4-chlorophenyl)-3-methylbutyrate], Fenpropathrin[(RS)-α-cyano-3-phenoxybenzyl 2,2,3,3-tetramethylcyclopropanecarboxylate], Cypermethrin[(RS)-α-cyano-3-phenoxybenzyl(1RS,3RS)-3-(2,2- dichlorovinyl)-2,2-dimethylcyclopropanecarboxylate], Permethrin[3-phenoxybenzyl (1RS,3RS)-3-(2,2-dichlorovinyl)-2,2-dimethylcyclopropanecarboxylate], Cyhalothrin[(RS)-α-cyano-3-phenoxybenzyl (Z)-(1RS, 3RS)-3-(2-chloro-3,3,3-trifluoropropenyl)-2,2-dimethylcyclopropanecarboxylate], Deltamethrin[(S)-α-cyano-m-phenoxybenzyl(1R,3R)-3-(2,2-dibromovinyl)-2,2-dimethylcyclopropanecarboxylate], Cycloprothrin[(RS)-α-cyano-3-phenoxybenzyl(RS)-2,2-dichloro-1-(4-ethoxyphenyl)cyclopropanecarboxylate], Fluvalinate[α-cyano-3-phenoxybenzyl N-(2-chloro-α,α,α-trifluoro-p-tolyl)-D-valinate], Bifenthrin[2-methylbiphenyl-3-ylmethyl)(Z)-(1RS)-cis-3-(2-chloro-3,3,3-trifluoropropen-1-yl)-2,2-dimethylcyclopropanecarboxylate], Acrinathrin [cyano-(3-phenoxyphenyl)methyl[1R-{1α(S*),3α(Z)}]-2, 2-dimethyl-3-[3-oxo-3-(2,2,2-trifluoro-1-(trifluoromethyl)-ethoxy-1-propenyl]cyclopropanecarboxylate], 2-methyl-2-(4bromodifluoromethoxyphenyl)propyl(3-phenoxybenzyl) ether, Traromethrin[(S)-α-cyano-3-phenoxylbenzyl (1R, 3R)-3-[(1'RS)(1',1',2',2'-tetrabromoethyl)]-2,2-dimethylcyclopropanecarboxylate] and Silafluofen[4-ethoxylphenyl[3-(4fluoro-3-phenoxyphenyl)propyl] dimethylsilane]; thiadiazine derivatives such as Buprofezin [2-tert-butylimino-3-isopropyl-5-phenyl-1,3,5-thiadiazin-4-one]; nitroimidazolidine derivatives such as Imidacloprid[1-(6-chloro-3-pyridylmethyl)-N-nitroimidazolidin-2-ylidenamine]; Nereistoxin derivatives such as Cartap[S,S'-(2-dimethylaminotrimethylene)bisthiocarbamate], Thiocyclam[N,N-di-methyl-1,2,3-trithian-5-ylamine] and Bensultap[S,S'-2-dimethylaminotrimethylene di-(benzenethiosulfonate)]; N-cyanoamidine derivatives such as acetamiprid[N-cyano-N'-methyl-N'-(6-chloro-3-pyridylmethyl)acetamidine]; chlorinated hydrocarbons such as Endosulfan[6,7,8,9,10,10-hexachloro-1,5,5a,6,9,9a-hexahydro-6,9-methano-2,4,3-benzodioxathiepinoxide], γ-BHC[1,2,3,4,5,6-hexachlorocyclohexane] and Kelthane [1,1-bis(chlorophenyl)-2,2,2-trichloroethanol]; benzoylphenylurea compounds such as Chlorfluazuron[1-(3,5-dichloro-4(3-chloro-5-trifluoromethylpyridin-2-yloxy)phenyl)-3-(2, 6-difluorobenzoyl)urea], Teflubenzuron[1-(3,5-dichloro-2, 4-difluorophenyl)-3-(2,6-difluorobenzoyl)urea] and Fulphenoxron[1-(4-(2-chloro-4trifluoromethylphenoxy)-2-fluorophenyl)-3-(2,6-difluorobenzoyl)urea]; formamidine derivatives such as Amitraz[N,N'-[(methylimino) dimethylidine]-di-2,4-xylidine] and Chlordimeform[N'-(4chloro-2-methylphenyl)-N,N-dimethylmethanimidamide]; thiourea derivatives such as Diafenthiuron[N-(2,6-diisopropyl-4-phenoxyphenyl)-N'-tert-butylcarbodiimide]; Fipronyl[5-amino-1-(2,6-dichloro-α,α,α-trifluoro-p-tolyl) -4-trifluoromethylsulfinylpyrazole-3-carbonitrite], Tebfenozide[N-tert-butyl-N'-(4-ethylbenzoyl)-3,5-dimethylbenzohydrazide], 4-bromo-2-(4-chlorophenyl)-1-ethoxymethyl-5-trifluoromethylpyrrole-3-carbonitrile, Chlorfenapyl[4-bromo-2-(4chlorophenyl)-1-ethoxymethyl-S-trifluoromethylpyrole-3-carbonitril], Bromopropylate[isopropyl 4,4'-dibromobenzylate], Tetradifon[4chlorophenyl-2,4,5-trichlorophenyl sulfone], Quinomethionate[S,S-6-methylquinoxaline-2,3-diyldithiocarbonate], Propargite[2-(4-tert-butylphenoxy) cyclohexyl prop-2-yl sulfite], Fenbutatin oxide[bis[tris(2-methyl-2-phenylpropyl)tin)oxide], Hexythiazox[(4RS, 5RS)-5-(4-chlorophenyl)-N-chlorohexylmethyl-2-oxo-1,3-thiazolidine-3-carboxamide], Chlofentezine[3,6-bis(2-chlorophenyl)-1,2,4,5-tetrazine], Pyridaben[2-tert-butyl-5-(4-tert-butylbenzylthio)-4chloropyridazin-3(2H)-one], Fenpyroximate[tert-butyl-(E)-4-[(1,3-dimethyl -5-phenoxypyrazol-4-yl)methyleneaminooxymethyl] benzoate], Tebfenpyrad[N-4-tert-butylbenzyl)-4-chloro-3-ethyl-1-methyl-5-pyrazol carboxamide], polynactin complexes including tetranactin, dinactin and trinactin; Milbemectin, Avermectin, Ivermectin, Azadilactin[AZAD], pyrimidifen[5-chloro-N-[2-{4-(2-ethoxyethyl)- 2,3-dimethylphenoxy}ethyl]-6-ethylpyrimidin-4-amine] and Pimetrozine[2,3,4,5-tetra-hydro-3-oxo-4-[(pyridin-3-yl)-methyleneamino]-6-methyl-1,2,4-triazine].

When the present compound is used as an active ingredient of insecticidal/acaricidal agents for agriculture, the application amount thereof is usually in the range of 0.1 to 100 g per 10 ares. In the case of emulsifiable concentrates, wettable powders and flowable concentrates, which are used after diluted with water, the application concentration thereof is usually in the range of 0.1 to 500 ppm. In the case of granules and dusts, they are applied as such without any dilution. When the present compound is used as an active ingredient of insecticidal/acaricidal agents for epidemic prevention, it is formulated into a dosage form such as emulsifiable concentrates, wettable powders and flowable concentrates, which are applied after diluted with water to a typical concentration of 0.1 to 500 ppm; or it is formulated into a dosage form such as oil sprays, aerosols, fumigants and poisonous baits, which are applied as such without any dilution.

The application amount and application concentration may vary depending upon various conditions such as formulation type, application time, place and method, kind of noxious insects, mites and ticks, and degree of damage, and they can be increased or decreased without limitation to the above range.

The present invention will be further illustrated by the following production examples, formulation examples and test examples, which are not to be construed to limit the scope thereof.

The following are production examples for the present compounds according to various production processes.

PRODUCTION EXAMPLE 1

Production of Compound (10) by Production Process E

To a solution of 0.44 g of 4-(3,3-dichloro-2-propenyloxy)-2,6-dichlorophenol, 0.20 g of 2-(2-hydroxyethyl)thiophene and 0.40 g of triphenylphosphine dissolved in 10 ml of tetrahydrofuran was added dropwise a solution of 0.31 g of diisopropyl azodicarboxylate dissolved in 5 ml of tetrahydrofuran, while stirring at room temperature. After stirring at room temperature for 12 hours, the reaction mixture was concentrated, to which 20 ml of diethyl ether was added, and the precipitate was filtered. The filtrate was concentrated, and the residue was subjected to silica gel chromatography, which afforded 0.38 g of 3,5-dichloro-4-(2-(2-thienyl)ethoxy)-1-(3,3-dichloro-2-propenyloxy) benzene (62% yield), $n_D^{25.6}$ 1.5919.

PRODUCTION EXAMPLE 2

Production of Compound (1) by Production Process D

To a mixture of 0.40 g of 2,6-dichloro-4-(3,3-dichloro-2-propenyloxy)phenol, 0.21 g of potassium carbonate and 20 ml of N,N-dimethylformamide was added dropwise a solution of 0.25 g of 6-chloro-3-(chloromethyl)pyridine dissolved in 5 ml of N,N-dimethylformamide, while stirring at room temperature. After stirring at room temperature for 7 hours, the reaction mixture was poured into ice-water, and extracted twice with 50 ml of diethyl ether. The combined ether layer was washed with water, dried with anhydrous magnesium sulfate, and concentrated to obtain a crude product. The crude product was subjected to silica gel chromatography, which afforded 0.44 g of 3,5-dichloro-4-(6-chloro-3-pyridylmethyloxy)-1-(3,3-dichloro-2-propenyloxy)benzene (77% yield), m.p. 93.3° C.

PRODUCTION EXAMPLE 3

Production of Compound (9) by Production Process E

To a solution of 0.43 g of 4-(3,3-dichloro-2-propenyloxy)-2,6-dichlorophenol, 0. 16 g of 4-(hydroxymethyl)pyridine and 0.39 g of triphenylphosphine dissolved in 10 ml of tetrahydrofuran was added dropwise a solution of 0.30 g of diisopropyl azodicarboxylate dissolved in 5 ml of tetrahydrofuran, while stirring at room temperature. After stirring at room temperature for 12 hours, the reaction mixture was concentrated, to which 20 ml of diethyl ether was added, and the precipitate was filtered. The filtrate was concentrated, and the residue was subjected to silica gel chromatography, which afforded 0.29 g of 3,5-dichloro-4-(4-pyridylmethyloxy)-1-(3,3-dichloro-2-propenyloxy)benzene (51% yield), m.p. 74.0° C.

PRODUCTION EXAMPLE 4

Production of Compound (25) by Production Process E

A reaction vessel was charged with 0.20 g of 3,5-dichloro-4-(3-bromopropyloxy)-1-(3,3-dichloro-2-propenyloxy)benzene, 0.08 g of thiophene-2-carboxylic acid, 0.08 g of potassium carbonate and 10 ml of N,N-dimethylformamide. After stirring at room temperature for 12 hours, the reaction mixture was poured into water, and extracted twice with 30 ml of diethyl ether. The combined ether layer was washed with water, dried with anhydrous magnesium sulfate, and concentrated to obtain a crude product. The crude product was subjected to silica gel chromatography, which afforded 0.18 g of 3,5-dichloro-4-(3-(thiophene-2-carboxylate)propyloxy)-1-(3,3-dichloro-2-propenyloxy)-benzene (81% yield), $n_D^{24.0}$ 1.5814.

PRODUCTION EXAMPLE 5

Production of Compound (29) by Production Process E

To a mixture of 0.4 g of 2-[2-(4-chlorophenyl)-1,3-dioxolan-4-yl]ethanol, 0.46 g of triphenylphosphine and 6 ml of tetrahydrofuran was added dropwise 0.35 ml of diisopropyl azodicarboxylate, while stirring at room temperature. After further stirring for 15 minutes, a solution of 0.5 g of 4-(3,3-dichloro-2-propenyloxy)-2,6-dichlorophenol in 2 ml of tetrahydrofuran was added. After stirring continued at room temperature for 3 hours, the reaction mixture was concentrated, and the residue was subjected to silica gel chromatography, which afforded 0.3 g of 3,5-dichloro-1-(3,3-dichloro-2-propenyloxy)-4-[2-[2-(4-chlorophenyl)-1,3-dioxolan-4-yl]ethoxy]benzene (35% yield), m.p. 84.1° C.

PRODUCTION EXAMPLE 6

Production of Compound (45) by Production Process E

To a solution of 0.33 g of 2-(3-hydroxypropyloxy)-5-trifluoromethyl-pyridine, 0.40 g of 2-chloro-6-methyl-4-(3,3-dichloro-2-propenyloxy)phenol and 0.41 g of triphenylphosphine dissolved in 30 ml of dichloromethane was added dropwise a solution of 0.32 g of diisopropyl azodicarboxylate dissolved in 3 ml of dichloromethane, while stirring at room temperature. After stirring at room temperature for 24 hours, the reaction mixture was concentrated to obtain a residue. The residue was subjected to silica gel chromatography, which afforded 0.56 g of 3-chloro-5-methyl-4-[3-(5-trifluoromethyl-2-pyridyloxy)propyloxy]-1-(3,3-dichloro-2-propenyloxy)benzene (92% yield), $n_D^{23.6}$ 1.5294.

PRODUCTION EXAMPLE 7

Production of Compound (46) by Production Process E

To a solution of 0.26 g of 2-(4-hydroxybutyloxy)-5-trifluoromethylpyridine, 0.3 g of 2-chloro-6-methyl-4-(3,3-dichloro-2-propenyloxy)phenol and 0.31 g of triphenylphosphine dissolved in 30 ml of dichloromethane was added dropwise a solution of 0.24 g of diisopropyl azodicarboxylate dissolved in 5 ml of dichloromethane, while stirring at room temperature. After stirring at room temperature for 24 hours, the reaction mixture was concentrated to obtain a residue. The residue was subjected to silica gel chromatography, which afforded 0.50 g of 3-chloro-5-methyl-4-[4-(5-trifluoromethyl-2-pyridyloxy)butyloxy]-1-(3,3-dichloro-2-propenyloxy)benzene (89% yield), $n_D^{23.0}$ 1.5275.

PRODUCTION EXAMPLE 8

Production of Compound (47) by Production Process A

In 10 ml of N,N-dimethylformamide were dissolved 0.7 g of 3-ethyl-5-methyl-4-[3-(5-trifluoromethyl-2-pyridyloxy)propyloxy]phenol and 0.27 g of potassium carbonate, to which a solution of 0.34 g of 1,1,3-trichloropropene dissolved in 5 ml of N,N-dimethylformamide was added dropwise, while stirring at room temperature. After stirring at room temperature for 12 hours, the reaction mixture was poured into ice-water, and extracted twice with 100 ml of diethyl ether. The combined diethyl ether was washed with water, dried with anhydrous magnesium sulfate, and concentrated to obtain a crude product. The crude produce was subjected to silica gel chromatography, which afforded 0.6 g of 3-ethyl-5-methyl-4-[3-(5-trifluoromethyl-2-pyridyloxy)propyloxy]-1-(3,3-di-chloro-2-propenyloxy)benzene (65% yield), $n_D^{23.0}$ 1.5188.

PRODUCTION EXAMPLE 9

Production of Compound (48) by Production Process A

In 10 ml of N,N-dimethylformamide were dissolved 0.6 g of 3-ethyl-5-methyl-4-[4-(5-trifluoromethyl-2-pyridyloxy)butyloxy]phenol and 0.23 g of potassium carbonate, to which a solution of 0.28 g of 1,1,3-trichloropropene dissolved in 5 ml of N,N-dimethylformamide was added dropwise, while stirring at room temperature. After stirring at room temperature for 12 hours, the reaction mixture was poured into ice-water, and extracted twice with 100 ml of diethyl ether. The combined diethyl ether was washed with water, dried with anhydrous magnesium sulfate, and concentrated to obtain a crude product. The crude produce was subjected to silica gel chromatography, which afforded 0.50 g of 3-ethyl-5-methyl-4-[4-(5-trifluoromethyl-2-pyridyloxy)butyloxy]-1-(3,3-dichloro-2-propenyloxy)benzene (64% yield), $n_D^{23.0}$ 1.5170.

PRODUCTION EXAMPLE 10

Production of Compound (50) by Production Process A

In 10 ml of N,N-dimethylformamide were dissolved 0.45 g of 3,5-diethyl-4-[3-(5-trifluoromethyl-2-pyridyloxy)propyloxy]phenol and 0.17 g of potassium carbonate, to which a solution of 0.18 g of 1,1,3-trichloropropene dissolved in 5 ml of N,N-dimethylformamide was added dropwise, while stirring at room temperature. After stirring at room temperature for 12 hours, the reaction mixture was poured into ice-water, and extracted twice with 100 ml of diethyl ether. The combined diethyl ether was washed with water, dried with anhydrous magnesium sulfate, and concentrated to obtain a crude product. The crude produce was subjected to silica gel chromatography, which afforded 0.35 g of 3,5-diethyl-4-[3-(5-trifluoromethyl-2-pyridyloxy)propyloxy]-1-(3,3-dichloro-2-propenyloxy)benzene (60% yield), $n_D^{20.0}$ 1.5192.

PRODUCTION EXAMPLE 11

Production of Compound (49) by Production Process H

A mixture of 1.0 g of 1-(3-bromopropyloxy)-2,6-dichloro-4-(3,3-dichloro-2-propenyloxy)benzene and 4.0 g of 2-amino-5-(trifluoromethyl)pyridine was stirred at 90° C. for 3 hours. The reaction mixture was cooled to room temperature, and subjected to silica gel chromatography, which afforded 0.14 g of 3,5-dichloro-1-(3,3-dichloro-2-propenyloxy)-4-(3-(5-(trifluoromethyl)-2-pyridylamino)propyloxy)benzene (12% yield), $n_D^{25.0}$ 1.5525.

PRODUCTION EXAMPLE 12

Production of Compound (36) by Production Process A

A mixture of 0.5 g of 3,5-dichloro-4-[3-(5-trifluoromethylpyridin-2-yloxy)propyloxy]phenol, 0.25 g of 1,1,3-trichloropropene, 0.2 g of potassium carbonate and 3 ml of N,N-dimethylformamide was stirred at room temperature overnight. The reaction mixture was subjected to silica gel chromatography, which afforded 0.3 g of 3,5-di-chloro-1-(3,3-dichloro-2-propenyloxy)-4-[3-(5-trifluoromethylpyridin-2-yloxy)propyloxy]benzene (47% yield), $n_D^{20.5}$ 1.5377.

PRODUCTION EXAMPLE 13

Production of Compound (36) by Production Process F

First, 2-(3-methanesulfonyloxypropyloxy)-5-trifluoromethylpyridine was prepared as follows.

A mixture of 12.6 g of 1,3-propanediol and 100 ml of N,N-dimethylformamide was stirred under a nitrogen stream, to which 3.30 g of an oily mixture containing 60% sodium hydride was added in small portions at room temperature over 30 minutes. After further stirring continued at room temperature for 1 hour, 20 ml of a DMF solution of 10.0 g of 2-chloro-5-trifluoromethylpyridine was added dropwise over 40 minutes. After further stirring continued under a nitrogen stream at room temperature overnight, 100 ml of about 2 N diluted hydrochloric acid was added over 15 minutes to stop the reaction. The reaction mixture was extracted twice with toluene at a total volume of 500 ml. The combined toluene layer was successively washed with diluted hydrochloric acid and aqueous sodium bicarbonate solution, dried with magnesium sulfate, and concentrated to obtain an oily product. The oily product was dissolved in 300 ml of hexane by heating, followed by recrystallization, which afforded 5.3 g of 2-(3-hydroxypropyloxy)-5-trifluoromethylpyridine as almost pure crystals (44% yield), m.p. 46.6° C.

A mixture of 4.0 g of 2-(3-hydroxypropyloxy)-5-trifluoromethylpyridine, 3.4 ml of triethylamine and 25 ml of toluene was vigorously stirred under a nitrogen stream, while cooling in chilled water bath to 5° C. Then, 1.63 g of methanesulfonyl chloride was added dropwise to this mixture at such a rate that the reaction temperature did not exceed 10° C., and the chilled water bath was removed. After further stirring continued at room temperature for 1.5 hours, 250 ml of water was added thereto, and the mixture was vigorously stirred for further 30 minutes, followed by phase separation. The toluene layer was washed once with water, dried with magnesium sulfate, and concentrated, which afforded 5 g of 2-(3-methanesulfonyloxypropyloxy)-5-trifluoromethylpyridine as an oily product (92% yield).

$^1$H-NMR δ (ppm) [CDCl$_3$, TMS] 8.39 (1H, br, s), 7.75 (1H, dd), 6.80 (1H, d), 4.0–5.0 (4H), 3.00 (3H, s), 2.30 (2H, quint.)

A mixture of 5 g of 2-(3-methanesulfonyloxypropyloxy)-5-trifluoromethylpyridine, 5 g of 4(3,3-dichloro-2-propenyloxy)-2,6-dichlorophenol, 2.64 g of potassium carbonate and 300 ml of N,N-dimethylformamide was vigorously stirred at room temperature for 4 days. Then, 300 ml of 2 N hydrochloric acid was added to this mixture, and extracted twice with toluene at a total volume of 300 ml. The combined toluene layer was successively washed with 2 N hydrochloric acid and aqueous sodium bicarbonate solution, dried with magnesium sulfate, and concentrated to obtain about 8 g of an oily product. The oily product was subjected to silica gel chromatography, which afforded 6.0 g of 3,5-dichloro-1-(3,3-dichloro-2-propenyloxy)-4-[3-(5-trifluoromethylpyridin-2-yloxy)propyloxy]benzene (70% yield).

The following are specific examples of the present compound under the corresponding compound numbers with their physical properties, if measured.

(1) 3,5-Dichloro-4-(6-chloro-3-pyridylmethyloxy)-1-(3,3-dichloro-2-propenyloxy)benzene m.p. 93.3° C.

(2) 3,5-Dichloro-4-(2,6-dichloro-3-pyridylmethyloxy)-1-(3,3-dichloro-2-propenyloxy)benzene m.p. 73.3° C.

(3) 3,5-Dichloro-4-(2-(1-pyrazolynyl)ethoxy)-1-(3,3dichloro-2-propenyloxy)benzene m.p. 59.8° C.

(4) 3,5-Dichloro-4-(2-(1-pyrazolynyl)ethoxy)-1-(3,3-dibromo-2-propenyloxy)benzene m.p. 55.3° C.

(5) 3,5-Dichloro-4-(2-pyridylmethyloxy)-1-(3,3-dichloro-2-propenyloxy)benzene m.p. 48.2° C.

(6) 3,5-Dichloro-4-(2-thienylmethyloxy)-1-(3,3-dichloro-2-propenyloxy)benzene m.p. 44.6° C.

(7) 3,5-Dichloro-4-(2-furanylmethyloxy)-1-(3,3-dichloro-2-propenyloxy)benzene m.p. 46.0° C.

(8) 3,5-Dichloro-4-(3-pyridylmethyloxy)-1-(3,3-dichloro-2-propenyloxy)benzene m.p. 105.9° C.

(9) 3,5-Dichloro-4-(4-pyridylmethyloxy)-1-(3,3-dichloro-2-propenyloxy)benzene m.p. 74.0° C.

(10) 3,5-Dichloro-4-(2-(2-thienyl)ethoxy)-1-(3,3-dichloro-2-propenyloxy)benzene $n_D^{25.6}$ 1.5919

(11) 3,5-Dichloro-4-(2-(3-methylthiazol-2-yl)ethoxy)-1-(3,3-dichloro-2-propenyloxy)benzene m.p. 30.4° C.

(12) 3,5-Dichloro-4-(2,4,5-trichloroimidazolynylmethyloxy)-1-(3,3-dichloro-2-propenyloxy)benzene m.p. 67.5° C.
(13) 3,5-Dichloro-4-(3,5-dimethyl-4-isoxazolynylmethyloxy)-1-(3,3-dichloro-2-propenyloxy)benzene m.p. 127.4° C.
(14) 3,5-Dichloro-4-(2-(3-thienyl)ethoxy)-1-(3,3-dichloro-2-propenyloxy)benzene $n_D^{24.0}$ 1.5916
(15) 3,5-Dichloro-4-(3-(4-pyridyl)propyloxy)-1-(3,3-dichloro-2-propenyloxy)benzene $n_D^{24.1}$ 1.5566
(16) 3,5-Dichloro-4-((2-(1,4-benzodioxanyl))methoxy)-1-(3,3-dichloro-2-propenyloxy)benzene $n_D^{24.6}$ 1.5799
(17) 3,5-Dichloro-4-((2-(5-formyl)furanyl)methoxy)-1-(3,3-dichloro-2-propenyloxy)benzene m.p. 91.5° C.
(18) 3,5-Dichloro-4-((3-(6-methylpyridyl))methoxy)-1-(3,3-dichloro-2-propenyloxy)benzene m.p. 86.7° C.
(19) 3,5-Dichloro-4-(2-(4pyridylthio)ethoxy)-1-(3,3-dichloro-2-propenyloxy)benzene m.p. 74.7° C.
(20) 3,5-Dichloro-4-(3-(3-pyridyl)propyloxy)-1-(3,3-dichloro-2-propenyloxy)benzene m.p. 48.3° C.
(21) 3-(2,6-Dichloro-4-(3,3-dichloro-2-propenyloxy)phenoxy)propyl nicotinate $n_D^{22.5}$ 1.5674
(22) 3-(2,6-Dichloro-4-(3,3-dichloro-2-propenyloxy)phenoxy)propyl isonicotinate $n_D^{22.5}$ 1.5667
(23) 3-(2,6-Dichloro-4-(3,3-dichloro-2-propenyloxy)phenoxy)propyl quinolinate $n_D^{25.5}$ 1.6002
(24) 3-(2,6-Dichloro-4-(3,3-dichloro-2-propenyloxy)phenoxy)propyl 2-furanate $n_D^{24.0}$ 1.5589
(25) 3-(2,6-Dichloro-4-(3,3-dichloro-2-propenyloxy)phenoxy)propyl 2-thiophenate $n_D^{24.0}$ 1.5814
(26) 3-(2,6-Dichloro-4-(3,3-dichloro-2-propenyloxy)phenoxy)propyl 3-thiophenate $n_D^{24.0}$ 1.5788
(27) 3-(2,6-Dichloro-4-(3,3-dichloro-2-propenyloxy)phenoxy)propyl picolinate $n_D^{24.0}$ 1.5737
(28) 3-(2,6-Dichloro-4-(3,3-dichloro-2-propenyloxy)phenoxy)propyl 3-quinolinate m.p. 92.3° C.
(29) 3,5-Dichloro-4-(2-(2-((2-(4chlorophenyl)-1,3-dioxanyl)))ethoxy)-1-(3,3-dichloro-2-propenyloxy)benzene m.p. 84.1° C.
(30) 3,5-Dichloro-4-(3-(2-pyridylthio)propyloxy)-1-(3,3-dichloro-2-propenyloxy)benzene $n_D^{22.5}$ 1.5982
(31) 3,5-Dichloro-4-(2-(6-ethoxy-2-benzothiezolyl)ethoxy)-1-(3,3-dichloro-2-propenyloxy)benzene m.p. 80.6° C.
(32) 3,5-Dichloro-4-(2-(2-benzoxazolyl)ethoxy)-1-(3,3-dichloro-2-propenyloxy)benzene m.p. 61.2° C.
(33) 3,5-Dichloro-4-(2-methyl-2-(2-(6-chloro)pyridyloxy)propyloxy)-1-(3,3-dichloro-2-propenyloxy)benzene $n_D^{22.5}$ 1.5742
(34) 3,5-Dichloro-4-(2-(N-phthalimido)ethoxy)-1-(3,3-dichloro-2-propenyloxy)benzene m.p. 115.2° C.
(35) 3,5-Dichloro-4-(3-(N-phthalimido)propyloxy)-1-(3,3-dichloro-2-propenyloxy)benzene m.p. 78.4° C.
(36) 3,5-Dichloro-4-(3-(5-trifluoromethyl-2-pyridyloxy)propyloxy)-1-(3,3-dichloro-2-propenyloxy)benzene $n_D^{20.5}$ 1.5377
(37) 3,5-Dichloro-4-(3-(3-chloro-5-trifluoromethyl-2-pyridyloxy)propyloxy)-1-(3,3-dichloro-2-propenyloxy)benzene $n_D^{22.5}$ 1.5429
(38) 3,5-Dichloro-4-(3-(N-(1,2-dihydroxy-3-bromo-5-trifluoromethyl-2-oxo)pyridyl)propyloxy)-1-(3,3-dichloro-2-propenyloxy)benzene m.p. 119.5° C.
(39) 3,5-Dichloro-4-(3-(2-benzimidazolylthio)propyloxy)-1-(3,3-dichloro-2-propenyloxy)benzene m.p. 120.7° C.
(40) 3,5-Dichloro-4-(3-(2-benzothiazolylthio)propyloxy)-1-(3,3-dichloro-2-propenyloxy)benzene $n_D^{22.5}$ 1.6322
(41) 3,5-Dichloro-4-(3-(5-trifluoromethyl-2-pyridyloxy)ethoxy)-1-(3,3-dichloro-2-propenyloxy)benzene m.p. 67.0° C.
(42) 3,5-Dichloro-4-(4-(5-trifluoromethyl-2-pyridyloxy)butyloxy)-1-(3,3-dichloro-2-propenyloxy)benzene $n_D^{21.3}$ 1.5359
(43) 3,5-Dichloro-4-(5-(5-trifluoromethyl-2-pyridyloxy)pentyloxy)-1-(3,3-dichloro-2-propenyloxy)benzene $n_D^{21.3}$ 1.5307
(44) 3,5-Dichloro-4-(6-(5-trifluoromethyl-1-(3,3-dichloro-2-propenyloxy)benzene $n_D^{21.3}$ 1.5302
(45) 3-Chloro-5-methyl-4-(3-(5-trifluoromethyl-2-pyridyloxy)propyloxy)-1-(3,3-dichloro-2-propenyloxy)benzene $n_D^{23.6}$ 1.5294
(46) 3-Chloro-5-methyl-4-(4-(5-trifluoromethyl-2-pyridyloxy)butyloxy)-1-(3,3-dichloro-2-propenyloxy)benzene $n_D^{23.0}$ 1.5275
(47) 3-Ethyl-5-methyl-4-(3-(5-trifluoromethyl-2-pyridyloxy)propyloxy)-1-(3,3-dichloro-2-propenyloxy)benzene $n_D^{23.0}$ 1.5188
(48) 3-Ethyl-5-methyl-4-(4-(5-trifluoromethyl-2-pyridyloxy)butyloxy)-1-(3,3-dichloro-2-propenyloxy)benzene $n_D^{23.0}$ 1.5170
(49) 3,5-Dichloro-4-(3-(5-trifluoromethyl-2-pyridylamino)propyloxy)-1-(3,3-dichloro-2-propenyloxy)benzene $n_D^{25.0}$ 1.5525
(50) 3,5-Diethyl-4-(3-(5-trifluoromethyl-2-pyridylamino propyloxy)-1-(3,3-dichloro-2-propenyloxy)benzene $n_D^{20.0}$ 1.5192
(51) 3,5-Diethyl-4-(4-(5-trifluoromethyl-2-pyridyloxy)butyloxy)-1-(3,3-dichloro-2-propenyloxy)benzene
(52) 3,5-Dichloro-4-(4-(3-chloro-5-trifluoromethyl-2-pyridyloxy)butyloxy)-1-(3,3-dichloro-2-propenyloxy)benzene
(53) 3,5-Dichloro-4-(3-(3-bromo-5-trifluoromethyl-2-pyridyloxy)propyloxy)-1-(3,3-dichloro-2-propenyloxy)benzene
(54) 3,5-Dichloro-4-(4-(3-bromo-5-trifluoromethyl-2-pyridyloxy)butyloxy)-1-(3,3-dichloro-2-propenyloxy)benzene
(55) 3,5-Dichloro-4-(3-(3-fluoro-5-trifluoromethyl-2-pyridyloxy)propyloxy)-1-(3,3-dichloro-2-propenyloxy)benzene
(56) 3,5-Dichloro-4-(4-(3-fluoro-5-trifluoromethyl-2-pyridyloxy)butyloxy)-1-(3,3-dichloro-2-propenyloxy)benzene
(57) 3,5-Dichloro-4-(3-(3,5-bistrifluoromethyl-2-pyridyloxy)propyloxy)-1-(3,3-dichloro-2-propenyloxy)benzene
(58) 3,5-Dichloro-4-(4-(3,5-bistrifluoromethyl-2-pyridyloxy)butyloxy)-1-(3,3-dichloro-2-propenyloxy)benzene
(59) 3,5-Dibromo-4-(3-(5-trifluoromethyl-2-pyridyloxy)propyloxy)-1-(3,3-dichloro-2-propenyloxy)benzene
(60) 3,5-Dibromo-4-(4-(5-trifluoromethyl-2-pyridyloxy)butyloxy)-1-(3,3-dichloro-2-propenyloxy)benzene
(61) 3,5-Dichloro-4-(4-(5-trifluoromethyl-2-pyridylamino)butyloxy)-1-(3,3-dichloro-2-propenyloxy)benzene
(62) 3,5-Diethyl-4-(3-(5-trifluoromethyl-2-pyridylamino)propyloxy)-1-(3,3-dichloro-2-propenyloxy)benzene
(63) 3-Ethyl-5-methyl-4-(3-(5-trifluoromethyl-2-pyridylamino)propyloxy)-1-(3,3-dichloro-2-propenyloxy)benzene
(64) 3-Chloro-5-methyl-4-(3-(5-trifluoromethyl-2-pyridylamino)propyloxy)-1-(3,3-dichloro-2-propenyloxy)benzene
(65) 3,5-Diethyl-4-(4-(5-trifluoromethyl-2-pyridylamino)butyloxy)-1-(3,3-dichloro-2-propenyloxy)benzene
(66) 3-Ethyl-5-methyl-4-(4-(5-trifluoromethyl-2-pyridylamino)butyloxy)-1-(3,3-dichloro-2-propenyloxy)benzene

(67) 3-Chloro-5-methyl-4-(4-(5-trifluoromethyl-2-pyridylamino)butyloxy)-1-(3,3-dichloro-2-propenyloxy)benzene

(68) 3,5-Dichloro-4-(2-(2-((2-(4-chlorophenyl)-1,3-dioxanyl)))ethoxy)-1-(3,3-dichloro-2-propenyloxy)benzene

(69) 3,5-Dichloro-4-(2-(2-((2-(4-trifluoromethylphenyl)-1,3-dioxanyl)))-ethoxy)-1-(3,3-dichloro-2-propenyloxy)benzene

(70) 3,5-Dichloro-4-(2-(2-((2-(4-trifluoromethoxyphenyl)-1,3-dioxanyl)))-ethoxy)-1-(3,3-dichloro-2-propenyloxy)benzene

(71) 3,5-Dichloro-4-(3-(2-pyridyloxy)propylamino)-1-(3,3-dichloro-2-propenyloxy)benzene m.p. 76.2° C.

The following are production examples for the intermediate compounds of the general formula [II] or [III].

INTERMEDIATE PRODUCTION EXAMPLE 1

A reaction vessel was charged with 5.0 g of 4-(benzyloxy)phenol and 100 ml of carbon tetrachloride, to which a solution 5.43 g of t-butyl hypochlorite dissolved in 5 ml of carbon tetrachloride was slowly added dropwise, while stirring under ice cooling. After 24 hours, the reaction mixture was poured into water, followed by phase separation. The organic layer (i.e., carbon tetrachloride layer) was washed with water, dried with anhydrous magnesium sulfate, and concentrated to obtain a crude product. The crude product was subjected to silica gel chromatography, which afforded 4.24 g of 2,4-dichloro-4-(benzyloxy)phenol (63% yield).

A reaction vessel was charged with 5.10 g of 1,3-dibromopropane, 2.40 g of potassium carbonate and 50 ml of N,N-dimethylformamide, to which a solution of 4.24 g of 2,6-dichloro-4-(benzyloxy)phenol dissolved in 10 ml of N,N-dimethylformamide was slowly added dropwise. After stirring at room temperature for 24 hours, the reaction mixture was poured into water, and extracted twice with 150 ml of diethyl ether. The combined ether layer was washed with water, dried with anhydrous magnesium sulfate, and concentrated to obtain a crude product. The crude product was subjected to silica gel chromatography, which afforded 4.24 g of 3,5-dichloro-4-(3-bromopropyloxy)-1-(benzyloxy)benzene (68% yield).

A reaction vessel was charged with 4.24 g of 3,5-dichloro-4-(3-bromopropyl-oxy)-1-(benzyloxy)benzene, 1.33 g of benzoic acid, 1.65 g of potassium carbonate and 20 ml of N,N-dimethylformamide. After stirring at room temperature for 24 hours, the reaction mixture was poured into water, and extracted twice with 150 ml of diethyl ether. The combined ether layer was washed with water, dried with anhydrous magnesium sulfate, and concentrated to obtain a crude product. The crude product was subjected to silica gel chromatography, which afforded 3.75 g of 3,5-dichloro-4-(3-benzoyloxy-propyloxy)-1-(benzoyloxy)benzene (80% yield).

A reaction vessel was charged with 3.75 g of 3,5-dichloro-4-(3-benzoyl-oxypropyloxy)-1-(benzyloxy)benzene, 5.0 g of 10% aqueous potassium hydroxide solution and 50 ml of methanol. After stirring at room temperature for 24 hours, the reaction mixture was concentrated. The concentrate was poured into water, and extracted twice with 150 m of diethyl ether. The combined ether layer was washed with water, dried with anhydrous magnesium sulfate, and concentrated to obtain a crude product. The crude product was subjected to silica gel chromatography, which afforded 2.56 g of 3-(2,6-dichloro-4-(benzyloxy)phenoxy)-1-propyl alcohol (90% yield).

A mixture of 0.5 g of 3-(2,6-dichloro-4-(benzyloxy)phenoxy)-1-propyl alcohol thus obtained, 0.1 g of an oily mixture containing 60% sodium hydride, and 3 ml of N,N-dimethylformamide was stirred at room temperature for 1 hour. Then, 0.3 g of 2-chloro-5-trifluoromethylpyridine was added to this mixture, followed by heating to 100° C. After stirring continued for 1 hour, the mixture was poured into 50 m of ice-water, and extracted with toluene at a total volume of 50 ml. The combined toluene layer was successively washed with diluted hydrochloric acid and aqueous sodium bicarbonate solution, dried with magnesium sulfate, and concentrated. The residue was silica gel chromatography, which afforded 0.5 g of 1-benzyloxy-3,5-dichloro-4-[3-(5-trifluoromethylpyridin-2-yloxy)propyloxy]benzene (67% yield).

$^1$H-NMR δ (ppm) [CDCl$_3$, TMS] 8.44 (1H, br, s), 7.76 (1H, dd), 7.2–7.5 (5H), 6.90 (2H, s), 6.81 (1H, d), 5.00 (2H, s), 4.62 (2H, t), 4.11 (2H, t), 2.31 (2H, quint.).

A reaction vessel was charged with 0.5 g of 1-benzyloxy-3,5-dichloro-4-(3-(5-trifluoromethylpyridin-2-yloxy)propyloxy)benzene and 50 ml of ethyl acetate, and the air in the vessel was- replaced with nitrogen. Then, 0.3 g of 10% palladium carbon was added, and the nitrogen in the vessel was replaced with hydrogen, followed by stirring at room temperature for 24 hours. The hydrogen in the vessel was replaced with nitrogen, after which the reaction mixture was filtered through Celite, and the filtrate was concentrated, which afforded 0.36 g of 3,5-dichloro-4-(3-(5-trifluoromethylpyridin-2-yloxy)propyloxy)phenol (92% yield).

$^1$H-NMR δ (ppm) [CDCl$_3$, TMS] 8.45 (1H, br, s), 7.75 (1H, dd), 6.77 (2H, s), 6.75 (1H, d), 4.60 (2H, t), 4.15 (2H, t), 2.25 (2H, quint.)

The following are specific examples of the intermediate compound of the general formula [II] or [III] under the corresponding compound numbers.

1) 3,5-Dichloro-4-(6-chloro-3-pyridylmethyloxy)phenol
2) 3,5-Dichloro-4-(2,6-dichloro-3-pyridylmethyloxy)phenol
3) 3,5-Dichloro-4-(2-(1-pyrazolynyl)ethoxy)phenol
4) 3,5-Dichloro-4-(2-pyridylmethyloxy)phenol
5) 3,5-Dichloro-4-(2-thienylmethyloxy)phenyl
6) 3,5-Dichloro-4-(2-furanylmethyloxy)phenol
7) 3,5-Dichloro-4-(3-pyridylmethyloxy)phenol
8) 3,5-Dichloro-4-(4-pyridylmethyloxy)phenol
9) 3,5-Dichloro-4-(2-(2-thienyl)ethoxy)phenol
10) 3,5-Dichloro-4-(2-(3-methylthiazol-2-yl)ethoxyphenol
11) 3,5-Dichloro-4-(2,4,5-trichloroimidazolynylmethyloxy)phenol
12) 3,5-Dichloro-4-(3,5-dimethyl-4-yloxazolynylmethyloxy)phenol
13) 3,5-Dichloro-4-(2-(3-thienyl)ethoxy)phenol
14) 3,5-Dichloro-4-(3-(4-pyridyl)propyloxy)phenol
15) 3,5-Dichloro-4-((2-(1,4-benzodioxanyl))methoxy)phenol
16) 3,5-Dichloro-4-((2-(5-formyl)furanyl)methoxy)phenol
17) 3,5-Dichloro-4-((3-(6-methylpyridyl))methoxy)phenol
18) 3,5-Dichloro-4-(2-(4-pyridylthio)ethoxy)phenol
19) 3,5-Dichloro-4-(3-(3-pyridyl)propyloxy)phenol
20) 3-(2,6-Dichloro-4-hydroxyphenoxy)propyl nicotinate
21) 3-(2,6-Dichloro-4-hydroxyphenoxy)propyl isonicotinate
22) 3-(2,6-Dichloro-4-hydroxyphenoxy)propyl quinolinate
23) 3-(2,6-Dichloro-4-hydroxyphenoxy)propyl 2-furanate
24) 3-(2,6-Dichloro-4-hydroxyphenoxy)propyl 2-thiophenate
25) 3-(2,6-Dichloro-4-hydroxyphenoxy)propyl 3-thiophenate 26) 3-(2,6-Dichloro-4-hydroxyphenoxy)propyl picolinate
27) 3-(2,6-Dichloro-4-hydroxyphenoxy)propyl quinolinate
28) 3,5-Dichloro-4-(2-(2-((2-(4-chlorophenyl)-1,3-dioxanyl)))ethoxy)phenol
29) 3,5-Dichloro-4-(3-(2-pyridylthio)propyloxy)phenol
30) 3,5-Dichloro-4-(2-(6-ethoxy-2-benzothiazolyl)ethoxy)phenol
31) 3,5-Dichloro-4-(2-(2-benzoxazolyl)ethoxy)phenol
32) 3,5-Dichloro-4-(2-methyl-2-(2-(6-chloro)pyridyloxy)propyloxy)phenol,
33) 3,5-Dichloro-4-(2-(N-phthalimido)ethoxy)phenol
34) 3,5-Dichloro-4-(3-(N-phthalimido)propyloxy)phenol
35) 3,5-Dichloro-4-(3-(5-trifluoromethyl-2-pyridyloxy)propyloxy)phenol
36) 3,5-Dichloro-4-(3-(3-chloro-5-trifluoromethyl-2-pyridyloxy)propyloxy)phenol
37) 3,5-Dichloro-4-(3-(N-(1,2-dihydroxy-3-bromo-5-trifluoromethyl-2-oxo)pyridyl)propyloxy))phenol
38) 3,5-Dichloro-4-(3-(2-benzimidazolylthio)propyloxy)phenol
39) 3,5-Dichloro-4-(3-(2-benzothiazolylthio)propyloxy)phenol
40) 3,5-Dichloro-4-(2-(5-trifluoromethyl-2-pyridyloxy)ethoxy)phenol
41) 3,5-Dichloro-4-(4-(5-trifluoromethyl-2-pyridyloxy)butyloxy)phenol
42) 3,5-Dichloro-4-(5-(5-trifluoromethyl-2-pyridyloxy)pentyloxy)phenol
43) 3,5-Dichloro-4-(6-(5-trifluoromethyl-2-pyridyloxy)hexyloxy)phenol
44) 3-Chloro-5-methyl-(3-(5-trifluoromethyl-2-pyridyloxy)propyloxy)phenol
45) 3-Chloro-5-methyl-4-(4-(5-trifluoromethyl-2-pyridyloxy)butyloxy)phenol
46) 3-Ethyl-5-methyl-4-(3-(5-trifluoromethyl-2-pyridyloxy)propyloxy)phenol
47) 3-Ethyl-5-methyl-4-(4-(5-trifluoromethyl-2-pyridyloxy)butyloxy)phenol
48) 3,5-Dichloro-4-(3-(5-trifluoromethyl-2-pyridylamino)propyloxy)phenol
49) 3,5-Diethyl-4-(3-(5-trifluoromethyl-2-pyridyloxy)propyloxy)phenol
50) 3,5-Diethyl-4-(4-(5-trifluoromethyl-2-pyridyloxy)butyloxy)phenol
51) 3,5-Dichloro-5-trifluoromethyl-2-pyridyloxy)butyloxy)phenol
52) 3,5-Dichloro-4-(3-(3-bromo-5-trifluoromethyl-2-pyridyloxy)propyloxy)phenol
53) 3,5-Dichloro-4-(4-(3-bromo-5-trifluoromethyl-2-pyridyloxy)butyloxy)phenol
54) 3,5-Dichloro-4-(3-(3-fluoro-5-trifluoromethyl-2-pyridyloxy)propyloxy)phenol
55) 3,5-Dichloro-4-(4-(4-fluoro-5-trifluoromethyl-2-pyridyloxy)butyloxy)phenol
56) 3,5-Dichloro-4-(3-(3,5-bistrifluoromethyl-2-pyridyloxy)propyloxy)phenol
57) 3,5-Dichloro-4-(4-(3,5-bistrifluoromethyl-2-pyridyloxy)butyloxy)phenol
58) 3,5-Dibromo-4-(3-(5-trifluoromethyl-2-pyridyloxy)propyloxy)phenol
59) 3,5-Dibromo-4-(4-(5-trifluoromethyl-2-pyridyloxy)butyloxy)phenol
60) 3,5-Dichloro-4-(4-(5-trifluoromethyl-2-pyridylamino)butyloxy)phenol
61) 3,5-Diethyl-4-(3-(5-trifluoromethyl-2-pyridylamino)propyloxy)phenol
62) 3-Ethyl-5-methyl-4-(3-(5-trifluoromethyl-2-pyridylamino)propyloxy)phenol
63) 3-Chloro-5-methyl-4-(3-(5-trifluoromethyl-2-pyridylamino)propyloxy)phenol
64) 3,5-Diethyl-4-(4-(5-trifluoromethyl-2-pyridylamino)butyloxy)phenol
65) 3-Ethyl-5-methyl-4-(4-(5-trifluoromethyl-2-pyridylamino)butyloxy)phenol
66) 3-Chloro-5-methyl-4-(4-(5-trifluoromethyl-2-pyridylamino)butyloxy)phenol
67) 3,5-Dichloro-4-(2-(2-((2-(4-chlorophenyl)-1,3-dioxanyl)))ethoxy)phenol
68) 3,5-Dichloro-4-(2-(2-((2-(4-trifluoromethylphenyl)-1,3-dioxanyl)))ethoxy)phenol
69) 3,5-Dichloro-4-(2-(2-((2-(4-trifluoromethoxyphenyl)-1,3-dioxanyl)))ethoxy)phenol The following are production examples for the intermediate compounds of the general formula [VII].

REFERENCE PRODUCTION EXAMPLE 1

A reaction vessel was charged with 30.5 g of 4-hydroxyphenyl benzoate, 21.6 g of potassium carbonate, 20.8 g of 1,1,3-trichloropropene and 100 ml of N,N-dimethylformamide. After stirring at room temperature for 15 hours, the reaction mixture was poured into water, and extracted twice with 50 ml of diethyl ether. The combined ether layer was washed with water, dried with anhydrous magnesium sulfate, and concentrated to obtain a crude product. The crude product was subjected to silica gel chromatography, which afforded 44.1 g of 4-(3,3-dichloro-2-propenyloxy)phenyl benzoate (96% yield).

A reaction vessel was charged with 44.1 g of 4-(3,3-dichloro-2-propenyloxy)phenyl benzoate and 400 ml of methanol, to which 33 g of 30% potassium hydroxide solution was slowly added dropwise under ice cooling. After stirring for 1 hour, the reaction mixture was made weakly acidic by the addition of 10% hydrochloric acid, and extracted twice with 150 ml of diethyl ether under salting out. The combined ether layer was washed with water, dried with anhydrous magnesium sulfate, and concentrated to obtain a crude product. The crude product was subjected to silica gel chromatography, which afforded 26.0 g of 4-(3,3-dichloro-2-propenyloxy)phenol (87% yield).

A reaction vessel was charged with 26.0 g of 4-(3,3-dichloro-2-propenyloxy)phenol and 500 ml of carbon tetrachloride, to which a solution of 27.1 g of tert-butyl hypochlorite dissolved in 20 ml of carbon tetrachloride was slowly added dropwise, while stirring under ice cooling. After 24 hours, the reaction mixture was poured into water, followed by phase separation. The organic layer (i.e., carbon tetrachloride layer) was washed with water, dried with anhydrous magnesium sulfate, and concentrated to obtain a crude product. The crude product was subjected to silica gel chromatography, which afforded 11.0 g of 2,6-dichloro-4-(3,3-dichloro-2-propenyloxy)phenol (32% yield), $n_D^{22.5}$ 1.5895.

REFERENCE PRODUCTION EXAMPLE 2

A solution of 50 g of 4-bromo-6-chloro-2-methylphenol and 42.5 g of benzyl bromide dissolved in 200 ml of N,N-dimethylformamide was stirred at room temperature, to which 37.4 g of potassium carbonate was added, and the mixture was stirred for 12 hours. After completion of the reaction, the solvent was removed by distillation under reduced pressure, and the residue was added to 400 ml of diethyl ether, washed with water, dried with anhydrous magnesium sulfate, and concentrated to obtain a crude product. The crude product was subjected to silica gel chromatography, which afforded 63 g of 4-bromo-6-chloro-2-methyl-1-benzyloxybenzene (90% yield).

Then, 40 g of 4-bromo-6-chloro-2-methyl-1-benzyloxybenzene was dissolved in 400 ml of tetrahydrofuran, followed by stirring at −70° C., to which 76 ml of n-butyl lithium solution (in hexane, 1.69 mol/liter) was added dropwise, followed by further stirring at −70° C. for 2 hours. To this reaction mixture was added dropwise a solution of 13.3 g of trimethoxyborane dissolved in 50 ml of tetrahydrofuran. Then, the reaction mixture was stirred for 1 hours, while warming to room temperature, and 100 ml of 10% aqueous hydrochloric acid solution was added in small portions, followed by stirring for 20 minutes. The tetrahydrofuran layer was washed with water, dried with anhydrous magnesium sulfate, and concentrated. The residue was mixed with 200 ml of toluene, and heated at 70° C. under stirring, to which 36 ml of 30% aqueous hydrogen peroxide solution was added dropwise. After heating under reflux for 1 hour, the reaction mixture was washed once with water, twice with 10% ferrous sulfate and then ammonium water, and once with water, followed by phase separation. The toluene layer was dried with anhydrous magnesium sulfate, and concentrated to obtain a crude product. The crude product was subjected to silica gel chromatography, which afforded 29 g of 4-benzyloxy-3-chloro-5-methylphenol (91% yield).

To a solution of 27.3 g of 4-benzyloxy-3-chloro-5-methylphenol dissolved in 250 ml of chloroform and being stirred at 0° C. were added 15.4 g of benzoyl chloride and then 13.3 g of triethylamine. After stirring at room temperature for 2 hours, the chloroform layer was washed with water, dried with anhydrous magnesium sulfate, and concentrated. The residue was subjected to silica gel chromatography, which afforded 35 g of 4-benzyloxy-3-chloro-5-methyl-1-benzoyloxybenzene (90% yield).

A reaction vessel was charged with 35 g of 4-benzyloxy-3-chloro-5-methyl-1-benzoyloxybenzene and 200 ml of ethyl acetate, and the air in the vessel was replaced with nitrogen. Then, 2 g of 10% palladium carbon was added, and the nitrogen in the vessel was replaced with hydrogen, followed by vigorous stirring at room temperature for 10 hours. The hydrogen in the vessel was replaced with nitrogen, after which the reaction mixture was filtered, and the filtrate was concentrated. The residue was subjected to silica gel chromatography, which afforded 25 g of 4-benzoyloxy-2-chloro-6-methylphenol (96% yield).

Then, 25 g of 4-benzoyloxy-2-chloro-6-methylphenol was dissolved in 250 ml of chloroform, to which 12 g of chloromethyl methyl ether was added, while stirring at 0° C., and 21 g of N-ethyldiisopropylamine was added dropwise. After heating under reflux for 1 hour, the chloroform layer was washed with water, and concentrated. The residue was subjected to silica gel chromatography, which afforded 27.4 g of 3-chloro-4-methoxymethoxy-5-methyl-1-benzoyloxybenzene (96% yield).

Then, 26 g of 3-chloro-4-methoxymethoxy-5-methyl-1-benzoyloxybenzene was dissolved in 200 ml of methanol, and the solution was stirred at room temperature for 1 hour, while adding dropwise 60 ml of 10% aqueous potassium hydroxide solution. After completion of the reaction, the solvent was removed by distillation under reduced pressure. The residue was added to 150 ml of water, neutralized with 10% aqueous hydrochloric acid solution, and extracted with 200 ml of diethyl ether. The solvent was removed by distillation under reduced pressure, and the residue was subjected to silica gel chromatography, which afforded 17.4 g of 3-chloro-4-methoxymethoxy-5-methylphenol (96% yield).

To a mixture of 10 g of 3-chloro-4-methoxymethoxy-5-methylphenol, 7 g of potassium carbonate and 100 ml of N,N-dimethylformamide was added dropwise a solution of 8 g of 1,1,3-trichloro-1-propene dissolved in 30 ml of N,N-dimethylformamide, while stirring at room temperature. After stirring at room temperature for 12 hours, the reaction mixture was poured into ice-water, and extracted twice with 200 ml of diethyl ether. The combined ether layer was washed with water, dried with anhydrous magnesium sulfate, and concentrated. The residue was subjected to silica gel chromatography, which afforded 14.1 g of 3-chloro-4-methoxymethoxy-5-methyl-1-(3,3-dichloro-2-propenyloxy)benzene (91% yield).

Then, 14.1 g of 3-chloro-4-methoxymethoxy-5-methyl-1-(3,3-dichloro-2-propenyloxy)benzene was dissolved in 100 ml of 80% aqueous acetic acid solution, followed by heating under reflux with stirring for 1 hour. After completion of the reaction, the reaction mixture was mixed with 200 ml of water, and extracted twice with 200 ml of diethyl ether. The combined ether layer was washed with water, dried with anhydrous magnesium sulfate, and concentrated. The residue was subjected to silica gel chromatography, which afforded 11.3 g of 2-chloro-6-methyl-(3,3-dichloro-2-propenyloxy)phenol (93% yield), m.p. 70.0° C.

The following is a production example for the intermediate compounds of general formula [XIII].

REFERENCE PRODUCTION EXAMPLE 3

Production of 3,5-dichloro-4-(3-bromopropyloxy)-1-(3,3-dichloro-2-propenyloxy)benzene A reaction vessel was charged with 10.6 g of 1,3-dibromopropane, 5.53 g of potassium carbonate and 100 ml of N,N-dimethylformamide, to which a solution of 30.5 g of 2,6-dichloro-4-(3,3-dichloro-2-propenyloxy)phenol dissolved in 40 ml of N,N-dimethylformamide was slowly added dropwise. After stirring at room temperature for 24 hours, the reaction mixture was poured into water, and extracted twice with 150 ml of diethyl ether. The combined ether layer was washed with water, dried with anhydrous magnesium sulfate, and concentrated to obtain a crude product. The crude product was subjected to silica gel chromatography, which afforded 11.1 g of 3,5-dichloro-4-(3-bromopropyloxy)-1-(3,3-dichloro-2-propenyloxy)benzene (77% yield), $n_D^{24.0}$ 1.5693.

The following are formulation examples in which "parts" are by weight and the present compounds are designated by the corresponding compound numbers as described above.

FORMULATION EXAMPLE 1

Emulsifiable Concentrates

Ten parts of each of the present compounds (1) to (70) are dissolved in 35 parts of xylene and 35 parts of N,N-dimethylformamide, to which 14 parts of polyoxyethylene styrylphenyl ether and 6 parts of calcium dodecylbenzenesulfonate are added, and the mixture is well stirred to give a 10% emulsifiable concentrate of each compound.

FORMULATION EXAMPLE 2

Wettable Powders

Twenty parts of each of the present compounds (1) to (70) are added to a mixture of 4 parts of sodium lauryl sulfate, 2 parts of calcium lignin sulfonate, 20 parts of synthetic hydrated silicon oxide fine powder and 54 parts of diatomaceous earth, and the mixture is stirred with a mixer to give a 20% wettable powder of each compound.

FORMULATION EXAMPLE 3

Granules

Five parts of each of the present compounds (1) to (70), 5 parts of synthetic hydrated silicon oxide fine powder, 5 parts of sodium dodecylbenzenesulfonate, 30 parts of bentonite and 55 parts of clay are mixed, and the mixture is well stirred. Then, a suitable amount of water is added to the mixture, which is further stirred, granulated with a granulator and then air-dried to give a 5% granule of each compound.

FORMULATION EXAMPLE 4

Dusts

One part of each of the present compounds (1) to (70) is dissolved in a suitable amount of acetone, to which 5 parts of synthetic hydrated silicon oxide fine powder, 0.3 part of PAP and 93.7 parts of clay are added, and the mixture is stirred with a mixer. The removal of acetone by evaporation gives a 1% dust of each compound.

FORMULATION EXAMPLE 5

Flowables

Twenty parts of each of the present compounds (1) to (70) are mixed with 1.5 parts of sorbitan trioleate and 28.5 parts of an aqueous solution containing 2 parts of polyvinyl alcohol, and the mixture is pulverized into fine particles having a particle size of not more than 3 $\mu$m with a sand grinder, to which 40 parts of an aqueous solution containing 0.05 part of xanthan gum and 0.1 part of aluminum magnesium silicate are added and then 10 parts of propylene glycol are added. The mixture is stirred to give a 20% water-based suspension of each compound.

FORMULATION EXAMPLE 6

Oil Solutions

First, 0.1 part of each of the present compounds (1) to (70) is dissolved in 5 parts of xylene and 5 parts of trichloroethane. Then, the solution was mixed with 89.9 parts of deodorized kerosine to give a 0.1% oil solution of each compound.

FORMULATION EXAMPLE 7

Oil-based Aerosols

First, 0.1 part of each of the present compounds (1) to (70), 0.2 part of tetramethrin, 0.1 part of d-phenothrin, and 10 parts of trichloroethane are dissolved in 59.6 parts of deodorized kerosine, and the solution is put in an aerozol vessel. Then, the vessel is equipped with a valve, through which 30 parts of a propellant (liquefied petroleum gas) are charged under increased pressure to give an oil-based aerosol of each compound.

FORMULATION EXAMPLE 8

Water-based Aerosols

An aerosol vessel is filled with 50 parts of pure water and a mixture of 0.2 part of each of the present compounds (1) to (70), 0.2 part of d-allethrin, 0.2 part of d-phenothrin, 5 parts of xylene, 3.4 parts of deodorized kerosine and 1 part of an emulsifier [ATMOS 300 (registered trade name by Atlas Chemical Co.)]. Then, the vessel is equipped with a valve, through which 40 parts of a propellant (liquefied petroleum gas) are charged under pressure to give a water-based aerosol of each compound.

FORMULATION EXAMPLE 9

Mosquito-coils

First, 0.3 g of each of the present compounds (1) to (70) is mixed with 0.3 g of d-allethrin, and the mixture is dissolved in 20 ml of acetone. The solution is uniformly mixed with 99.4 g of a carrier for mosquito-coils (prepared by mixing Tabu powder, pyrethrum marc powder and wood flour in the ratio of 4:3:3) under stirring. The mixture is well kneaded with 120 ml of water, molded and dried to give a mosquito-coil of each compound.

FORMULATION EXAMPLE 10

Electric Mosquito-mats

First, 0.4 g of each of the present compounds (1) to (70), 0.4 parts of d-allethrin and 0.4 g of pipenyl butoxide are dissolved in acetone to have a total volume of 10 ml. Then, 0.5 ml of the solution is uniformly absorbed in a substrate for electric mosquito-mats having a size of 2.5 cm×1.5 cm×0.3 cm (prepared by forming a fibrillated mixture of cotton linter and pulp into a sheet) to give an electric mosquito-mat of each compound.

FORMULATION EXAMPLE 11

Heating Smoke Formulations

First, 100 mg of each of the present compounds (1) to (70) is dissolved in a suitable amount of acetone. Then, the solution is absorbed in a porous ceramic plate having a size of 4.0 cm×4.0 cm×1.2 cm to give a heating smoke formulation of each compound.

FORMULATION EXAMPLE 12

Poison Baits

First, 10 mg of each of the present compounds (1) to (70) is dissolved in 0.5 ml of acetone, and the solution is uniformly mixed with 5 g of solid bait powder for animals (Breeding Solid Feed Powder CE-2, trade name by Japan Clea Co., Ltd.). Then, the removal of acetone by air drying gives a 0.5% poison bait of each compound.

The following test examples demonstrate that the present compounds are useful as an active ingredient of insecticidal/acaricidal agents. In these test examples, the present compounds are designated by the corresponding compound numbers as described above and the compounds used for comparison are designated by the corresponding compound symbols as shown in Table 47.

TABLE 47

| Compound | Chemical structure | Remarks |
| --- | --- | --- |
| (A) | 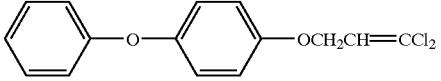 | Compound disclosed in JP-A 48-86835/1973, page 23 |
| (B) | 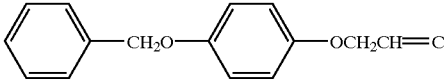 | Compound disclosed in JP-A 49-1526/1974, page 22 |

TEST EXAMPLE 1

Insecticidal Test Against *Spodoptera litura*

A 200-fold dilution containing an active ingredient at 500 ppm, which had been prepared by diluting with water an emulsifiable concentrate of the test compound obtained according to Formulation Example 1, was absorbed at a volume of 2 ml in 13 g of an artificial diet for *Spodoptera litura*, which had been prepared in a polyethylene cup having a diameter of 11 cm. Ten fourth-instar larvae of *Spodoptera litura* were set free in the cup. After 6 days, the survival of larvae was examined to determine the mortality. The test was conducted in duplicate.

As a result, it was found that the present compounds (1), (2), (5)–(7), (9)–(11), (14), (16)–(18), (20)–(26), (28)–(37) and (39)–(50) exhibited the mortality of 80% or more. In contrast, both compounds (A) and (B) for comparison exhibited the mortality of 0%.

TEST EXAMPLE 2

Test Against *Tetranychus urticae* Koch

Ten female adults of *Tetranychus urticae* Koch per one leaf were allowed to parasitize to a potting bean at the primary leaf stage harvested for 7 days after seeding, and these pots were placed in a thermostated room at 25° C. After 6 days, a chemical solution containing an active ingredient at 500 ppm, which had been prepared by diluting with water an emulsifiable concentrate of the test compound obtained according to Formulation Example 1, was sprayed at a volume of 15 ml over each pot on a turntable. At the same time, 2 ml of the same solution was drenched in the soil. After 8 days, the degree of damage on the respective plants caused by *Tetranychus urticae* Koch was examined. The effects were determined according to the following criteria:

−: Damage is scarcely observed.
+: Damage is slightly observed.
++: Damage is observed at the same level as in the non-treated field.

As a result, it was found that the present compounds (1), (7), (10), (15), (30), (32) and (33) were evaluated as "−" or "+". In the contrast, both compounds A and B for comparison were evaluated as "++".

TEST EXAMPLE 3

Insecticidal Test Against *Heliothis virescens*

A dilution containing an active ingredient at 100 ppm, which had been prepared by diluting with water an emulsifiable concentrate of the test compound obtained according to Formulation Example 1, was incorporated at a volume of 0.2 ml in an artificial diet. A second-instar larva of *H. virescens* was given the diet and bred in a plastic vessel. Ten insects were used by each treatment. After 6 days, the mortality was determined.

As a result, it was found that the present compounds (36), (42) and (43) exhibited the mortality of 80% or more. In contrast, both compounds (A) and (B) for comparison exhibited the mortality of 0%.

TEST EXAMPLE 4

Insecticidal Test Against *Plutella xylostella*

A chemical solution containing an active ingredient at 50 ppm, which had been prepared by diluting an emulsifiable concentrate of the test compound obtained according to Formulation Example 1 with water containing spreading agent RINOU (Nihon Nouyaku K.K.) to a degree such that the spreading agent had been 1000-fold diluted, was sprayed at a volume 25 ml over each pot of a potting cabbage at the five leaf stage. The treated plants were air dried, on which ten third-instar larvae of *Plutella xylostella* were set free. After 4 days, the mortality was determined.

As a result, it was found that the present compounds (36), (37), (42) and (45)–(48) exhibited the mortality of 80% or more. In contrast, both compounds (A) and (B) for comparison exhibited the mortality of 0%.

INDUSTRIAL APPLICABILITY

The present compounds have excellent insecticidal/acaricidal activity, so that they are satisfactorily effective for the control of noxious insects, mites and ticks.

What is claimed is:
1. A dihalopropene compound of the general formula:

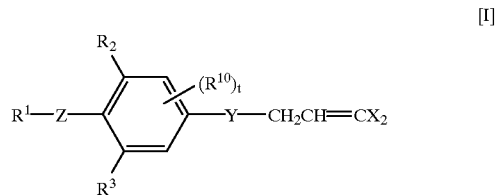

[I]

wherein Z is oxygen, sulfur or $NR^4$ (wherein $R^4$ is hydrogen or $C_1$–$C_3$ alkyl); Y is oxygen, sulfur or NH; X's are independently chlorine or bromine; $R^2$, $R^3$ and $R^{10}$ are independently halogen, $C_1$–$C_3$ haloalkyl or $C_1$–$C_3$ alkyl; t is an integer of 0 to 2; and $R^1$ is $Q_1$, $Q_2$, $Q_3$, $Q_4$, $Q_5$, $Q_6$ or $Q_7$ of the general formula:

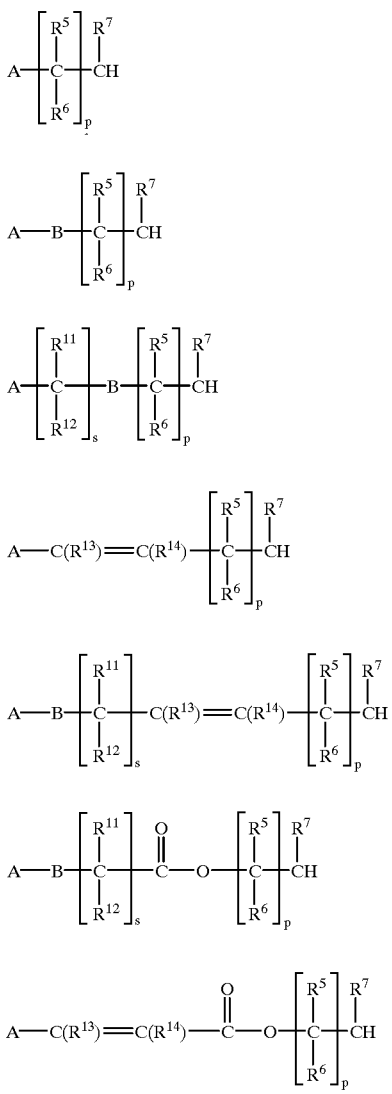

wherein A is an optionally substituted 6-membered ring with 2 or more nitrogen atoms that is optionally fused to a benzene ring; B is oxygen, $S(O)_q$, $NR^9$, $C(=G^1)G^2$ or $G^1C(=G^2)$; q is an integer of 0 to 2; $R^9$ is hydrogen, acetyl or $C_1$–$C_3$ alkyl; $G^1$ and $G^2$ are independently oxygen or sulfur; $R^5$, $R^6$, $R^7$, $R^{11}$ and $R^{12}$ are independently hydrogen, $C_1$–$C_3$ alkyl or trifluoromethyl; $R^{13}$ and $R^{14}$ are independently hydrogen $C_1$–$C_3$ alkyl, trifluoromethyl or halogen; p is an integer of 0 to 6; and s is an integer of 1 to 6.

2. The dihalopropene compound according to claim 1, wherein A is a 6-membered ring with 2 or more nitrogen atoms optionally substituted with $(R^8)_r$, wherein $R^8$ is halogen, nitro, cyano, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, ($C_1$–$C_2$ alkyl)aminocarbonyl or [di($C_1$–$C_2$ alkyl)amino]carbonyl, or $R^8$ is phenyl, benzyl, phenoxy, benzyloxy or pyridyloxy, each of which is optionally substituted with halogen, $C_1$–$C_4$ alkyl, $C_1$–$C_3$ haloalkyl, $C_1$–$C_4$ alkoxy or $C_1$–$C_3$ haloalkoxy; and r is an integer of 0 to 7.

3. The dihalopropene compound according to claim 1, wherein $R^2$ and $R^3$ are independently halogen or $C_1$–$C_3$ alkyl; and t is 0.

4. The dihalopropene compound according to claim 1, wherein $R^2$ and $R^3$ are independently chlorine, bromine, methyl, ethyl or isopropyl; and t is 0.

5. The dihalopropene compound according to claim 1, wherein $R^2$ and $R^3$ are both chlorine; and t is 0.

6. The dihalopropene compound according to claim 1, wherein $R^2$ is chlorine; $R^3$ is methyl; and t is 0.

7. The dihalopropene compound according to claim 1, wherein $R^2$ is ethyl; $R^3$ is methyl; and t is 0.

8. The dihalopropene compound according to claim 1, wherein $R^2$ and $R^3$ are both bromine; and t is 0.

9. The dihalopropene compound according to claim 1, wherein $R^2$ and $R^3$ are both ethyl; and t is 0.

10. The dihalopropene compound according to claim 1, wherein $R^2$ and $R^3$ are independently halogen or $C_1$–$C_3$ alkyl; t is 1 or 2; and $R^{10}$ is halogen or $C_1$–$C_3$ alkyl.

11. The dihalopropene compound according to claim 1, wherein $R^2$ and $R^3$ are independently halogen or $C_1$–$C_3$ alkyl; t is 1 or 2; and $R^{10}$ is halogen.

12. The dihalopropene compound according to claim 1, wherein Y and Z are both oxygen.

13. The dihalopropene compound according to claim 3, wherein Y and Z are both oxygen.

14. The dihalopropene compound according to claim 1, wherein $R^1$ is $Q_1$.

15. The dihalopropene compound according to claim 1, wherein $R^1$ is $Q_1$; p is 0 to 6; and A is pyridazinyl, pyrimidinyl or pyrazinyl, each of which is optionally substituted with $(R^8)_r$, wherein $R^8$ is halogen, nitro, cyano, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, ($C_1$–$C_2$ alkyl)aminocarbonyl or [di($C_1$–$C_2$ alkyl)amino]carbonyl, or $R^8$ is phenyl, benzyl, phenoxy, benzyloxy or pyridyloxy, each of which is optionally substituted with halogen, $C_1$–$C_4$ alkyl, $C_1$–$C_3$ haloalkyl, $C_1$–$C_4$ alkoxy or $C_1$–$C_3$ haloalkoxy; and r is an integer of 0 to 2.

16. The dihalopropene compound according to claim 1, wherein $R^1$ is $Q_2$.

17. The dihalopropene compound according to claim 1, wherein $R^1$ is $Q_2$; and A is pyrimidinyl, pyrazinyl, 1,2,4-triazinyl or 1,3,5-triazinyl, each of which is optionally substituted with $(R^8)_r$, wherein $R^8$ is halogen, nitro, cyano, $C_1$–$C_4$ alkyl, $C_1$–$C_3$ haloalkyl, $C_1$–$C_4$ alkoxy, $C_1$–$C_3$ haloalkoxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_2$–$C_4$ alkenyl, $C_2$–$C_4$ haloalkenyl, $C_2$–$C_4$ alkynyl, $C_2$–$C_4$ haloalkynyl, amino, dimethylamino, acetamido, acetyl, haloacetyl, formyl, carboxyl, methoxycarbonyl, $C_3$–$C_6$ cycloalkyl, ($C_1$–$C_2$ alkyl)aminocarbonyl or [di($C_1$–$C_2$ alkyl)amino]carbonyl, or $R^8$ is phenyl, benzyl, phenoxy, benzyloxy or pyridyloxy, each of which is optionally substituted with halogen, $C_1$–$C_4$ alkyl, $C_1$–$C_3$ haloalkyl, $C_1$–$C_4$ alkoxy or $C_1$–$C_3$ haloalkoxy; and r is an integer of 0 to 2.

18. An insecticidal/acaricidal agent comprising the dihalopropene compound according to claim 1 as an active ingredient.

* * * * *